United States Patent
Shabram

(10) Patent No.: US 10,126,219 B2
(45) Date of Patent: Nov. 13, 2018

(54) METHOD AND SYSTEM FOR REAL TIME CHARACTERIZATION OF SOFT MATERIALS AND BIOLOGICAL TISSUES BASED ON NONLINEAR PROPERTIES

(76) Inventor: Ali Shabram, Montreal (CA)

(*) Notice: Subject to any disclaimer, the term of this patent is extended or adjusted under 35 U.S.C. 154(b) by 1472 days.

(21) Appl. No.: 12/388,878

(22) Filed: Feb. 19, 2009

(65) Prior Publication Data

US 2010/0210971 A1    Aug. 19, 2010

(51) Int. Cl.
| | |
|---|---|
| A61B 5/103 | (2006.01) |
| G01N 3/08 | (2006.01) |
| A61B 5/00 | (2006.01) |
| A61B 90/00 | (2016.01) |

(52) U.S. Cl.
CPC .............. *G01N 3/08* (2013.01); *A61B 5/441* (2013.01); *A61B 2090/064* (2016.02); *G01N 2203/0094* (2013.01)

(58) Field of Classification Search
CPC .. G01N 3/08; G01N 3/10; G01N 3/12; G01N 3/16; G01N 2203/0092; G01N 2203/0094
USPC ........................................................ 600/587
See application file for complete search history.

(56) References Cited

U.S. PATENT DOCUMENTS

| | | | | |
|---|---|---|---|---|
| 7,937,249 | B2* | 5/2011 | Osborn, III et al. | |
| | | | | A61B 5/1076 |
| | | | | 600/300 |
| 2004/0138862 | A1* | 7/2004 | Hu ........................ | G01V 1/28 |
| | | | | 703/2 |
| 2004/0153292 | A1* | 8/2004 | Hay ....................... | G01N 3/068 |
| | | | | 702/189 |
| 2004/0236455 | A1* | 11/2004 | Woltman ............... | A61F 13/15 |
| | | | | 700/132 |
| 2005/0032029 | A1* | 2/2005 | Trunk .................... | G09B 23/06 |
| | | | | 434/300 |
| 2005/0256686 | A1* | 11/2005 | Stabelfeldt .......... | G06F 17/5018 |
| | | | | 703/6 |
| 2005/0267695 | A1* | 12/2005 | German ................ | G01N 3/30 |
| | | | | 702/41 |
| 2007/0015994 | A1* | 1/2007 | Hong .................... | A61B 5/035 |
| | | | | 600/407 |
| 2008/0173104 | A1* | 7/2008 | German ................ | G01N 3/30 |
| | | | | 73/862.381 |
| 2009/0210158 | A1* | 8/2009 | German ................ | G01N 3/30 |
| | | | | 702/2 |

OTHER PUBLICATIONS

Young et al. "Material properties of the human calcaneal fat pad in compression: experiment and theory" Jounal of Biomechanics 35 (2002) 1523-1531.*
Tie Hu et al. Direct and Inverse Problem Models for Large Soft-Tissue Deformation: Application to Haptic Feedback in Surgical Simulation, 2005 IEEE presented at Advanced Robotics, 2005/ICAR '05. Proceedings., 12th International Conference on Jul. 18-20, 2005.*

(Continued)

*Primary Examiner* — Michael C Stout

(57) ABSTRACT

Method and system for real time characterization of soft materials and biological tissues based on nonlinear properties with application in biological tissues diagnostics, robotic assisted surgery, tele-surgery, robotics and minimally invasive surgery is provided.

8 Claims, 48 Drawing Sheets

(56) References Cited

OTHER PUBLICATIONS

Kim et al. "Characterization of Viscoelastic Soft Tissue Properties from in vivo Animal Experiments and Inverse FE Parameter Estimation" J. Duncan and G. Gerig (Eds.): MICCAI 2005 pp. 599-606.*

Samur et al. "A robotic indenter for minimally invaasive measurement and characterization of soft tissue response" Medical image analysis 11 (2007) 361-373.*

Sun et al. "Computation models for mechanical deformation of soft tissues", Feb. 2002. Teaches hyperelastic nonlinear viscoelastic model.*

Medical Simulation, which contains Liu et al. "A Nonlinear Finite Element Model of Soft Tissue Indentation" ISMS 2004, LNCS 3078, pp. 67-76, 2004.*

"A nonlinear approach for characterization of viscoelastic materials with application in tactile sensing for robotics and minimally invasive surgery", a thesis of MASc in Department of Mechanical and Industrial Engineering of Concordia University, Montreal, Canada, Aug. 2008).

*Lecture Notes in Computer Science,* vol. 2878/2003, pp. 238-245.

Bonet, Wood (1997); "Nonlinear Continuum Mechanics for Finite element Analysis", Cambridge University Press.

\* cited by examiner

| Object | Property | Deformation speed (mm/s) | | |
|---|---|---|---|---|
| | | 1 | 2 | 5 |
| DMS-T43 | Total Energy (J*e-3) | 12.55 | 23 | 45 |
| | Dissipation (J/s*e-3) | 1.26 | 4.6 | 22.5 |
| DMS-T41-2 | Total Energy (J*e-3) | 6.85 | 16.15 | 36.49 |
| | Dissipation (J/s*e-3) | 0.69 | 3.23 | 7.3 |
| DMS-T41 | Total Energy (J*e-3) | 15.44 | 31.15 | 71.2 |
| | Dissipation (J/s*e-3) | 1.54 | 6.23 | 35.6 |
| DMS-T35 | Total Energy (J*e-3) | 3.8 | 5.9 | 14.1 |
| | Dissipation (J/s*e-3) | 0.38 | 1.18 | 7.05 |
| DMS-T31 | Total Energy (J*e-3) | 23.3 | 26.4 | 29.9 |
| | Dissipation (J/s*e-3) | 2.33 | 5.28 | 14.95 |

Fig 32

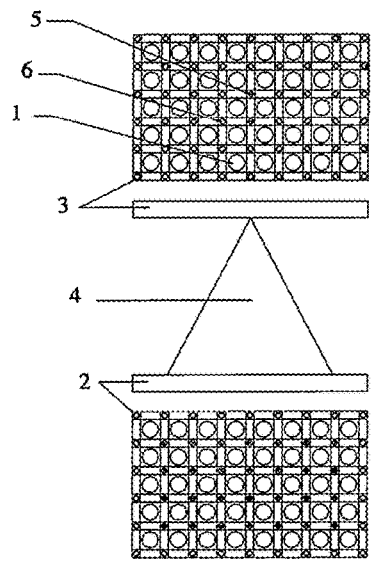
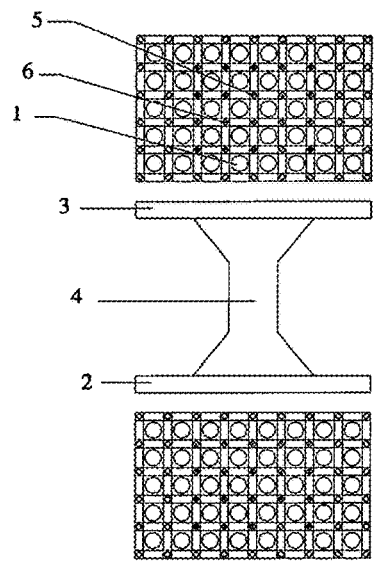
Fig. 41A                Fig.41B
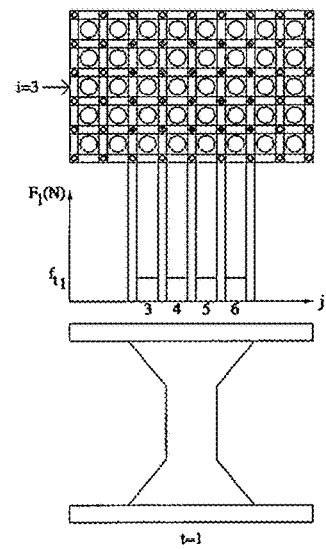
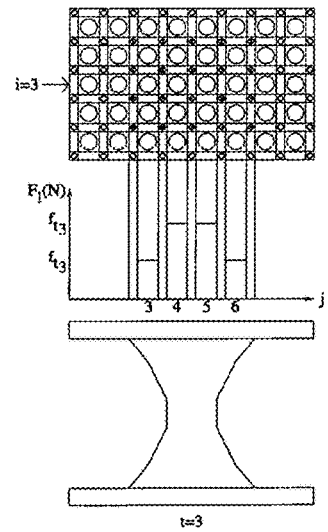
Fig. 41C                Fig. 41D

METHOD AND SYSTEM FOR REAL TIME CHARACTERIZATION OF SOFT MATERIALS AND BIOLOGICAL TISSUES BASED ON NONLINEAR PROPERTIES

CROSS-REFERENCE TO RELATED APPLICATION

Not Applicable

STATEMENT REGARDING FEDERALLY SPONSORED RESEARCH OR DEVELOPMENT

Not Applicable

THE NAME OF THE PARTIES TO A JOINT RESEARCH AGREEMENT

Not Applicable

BACKGROUND OF THE INVENTION

Field of the Invention

The characterization of soft materials, including biological tissues, has become first priority of researchers in field of materials, biomedical, biomechanics, robotics, etc, because of the behavior complications of these materials due to nonlinearities and time dependency. Moreover, the increasing demand of interaction between these materials and non human manipulators has required efficient systems to characterize materials in the same manner of human touch. The necessity of tactile feedback in minimally invasive surgery, robotic assisted surgery and tele-surgery has been reported frequently in literatures. Robotics researchers also requested tactile sensing systems with high versatility to characterize soft objects by end effecter manipulators in order to improve the functionality of robots to interact with environment of human. In addition, diagnostic of diseases based on physical properties of tissues has been tried and failed due to lack of an efficient characterization system. Detecting lumps, tumor and studying any other disorders which effect mechanical properties of tissues require a robust system for providing possibility of their studies. To this end, the desired system not only should have the capability of touch sense of human but should be more accurate and versatile to prepare the information that human touch is incapable to provide.

Description of the Related Art Including Information Disclosed Under 37 CFR 1.97 and 37 CFR 1.98

Brown et al. (*Lecture Notes in Computer Science*, Volume 2878/2003, pp. 238-245) reported the nonlinear behavior of porcine abdominal organs in-vivo, in-situ, and ex-corpus by performing measurements while deforming the tissue by a motorized endoscopic grasper. In the absence of an efficient nonlinear viscoelasticity, analyzing time dependency of the tissue was performed through relaxation tests showing inaccurate results. To provide real behavior analyses of nonlinearities and time dependency associated with biological tissues, Shabram ("A nonlinear approach for characterization of viscoelastic materials with application in tactile sensing for robotics and minimally invasive surgery", a thesis of MASc in Department of Mechanical and Industrial Engineering of Concordia University, Montreal, Canada, August, 2008) developed nonlinear hyperelasticity and nonlinear viscoelasticity analyses based on incremental nonlinear approach. The analytical and finite element simulations successfully confirmed the consistency of the model and method of analyses. The experimental as well confirmed the proposed model of time dependency of the material based on combination of two interactive elements within the structure of viscoelastic materials. The conclusion confirmed that the proposed model can be used for analyzing elastic/hyperelastic materials as time independent and viscoelastic/plastic materials as time dependent materials.

Based on the mentioned nonlinear approach, the method and system for characterization soft materials and biological tissues were developed in order to interact with any soft object disregarding geometry, accessibility condition and non-uniformity of behavior, and report nonlinear mechanical properties.

BRIEF SUMMARY OF THE INVENTION

The presented invention, applies the method for characterization soft materials and biological tissues by means of a system, whereas called system, which includes three main subsystems: analyzer, mechanisms and controller. The analyzer applies the method on the measurements which are taken place by mechanisms and controller enables the mechanisms to perform the deformations and measurements required in order to characterize the object by analyzer according to the method.

The system deals with soft materials/objects in general term and with biological tissues as in-vivo objects. These materials include elastic/hyperelastic and/or viscoelastic/plastic materials, which can be classified in two categories as time-independent and time-dependent materials, respectively. Therefore, nonlinear hyperelasticity and viscoelasticity analyses are applied by the analyzer for characterizing the object and monitoring the results as mechanical properties: nonlinear elastic modulus and dissipation function of energy.

Each object regarding the accessibility condition and geometry is deformed and its behavior is measured by appropriate mechanism. Consequently, the method of analyzing is applied by analyzer according to the specific strategy developed for each mechanism.

The behavior of materials is measured by performing deformations by compressive force applied by a mechanism. The results of measurements are generally the force and displacement with respect to time. Each mechanism obtains necessary information of geometry of the object to provide the analyzer with data of nonlinearities of geometry occurred during deformation.

The mechanisms are driven by a DC servo motor which is controlled by the controller to maintain the deformation rate constant. In the presence of an appropriate control device to regulate the deformation speed, some mechanisms can be driven manually as well.

In addition to regulating the torque and speed of the motor shaft of mechanism with respect to behavior of target object, the controller prevents the object to be damaged due to deformation more than preset range and possible impact of the mechanism. Furthermore, it performs self tests and provides the user with appropriate interfaces to interact with the mechanism.

BRIEF DESCRIPTION OF THE DRAWINGS

Having thus generally described the nature of the invention, references will now be made to the accompanying drawings, showing the way of illustration, preferred embodiments thereof, and in which:

FIG. 32 illustrates the summery of analyses of three deformation speeds for viscosity energy and dissipation.

FIG. 41 illustrates two objects with sharp edges and sensor arrays of the clamping faces of Robust clamp mechanism at time zero (41A and 41B) and force distribution of deformation of one of the objects with concentrated stress at time $t=1$ (41C) and $t=3$ (41D).

DETAILED DESCRIPTION OF THE PREFERRED EMBODIMENT

Figure 1:
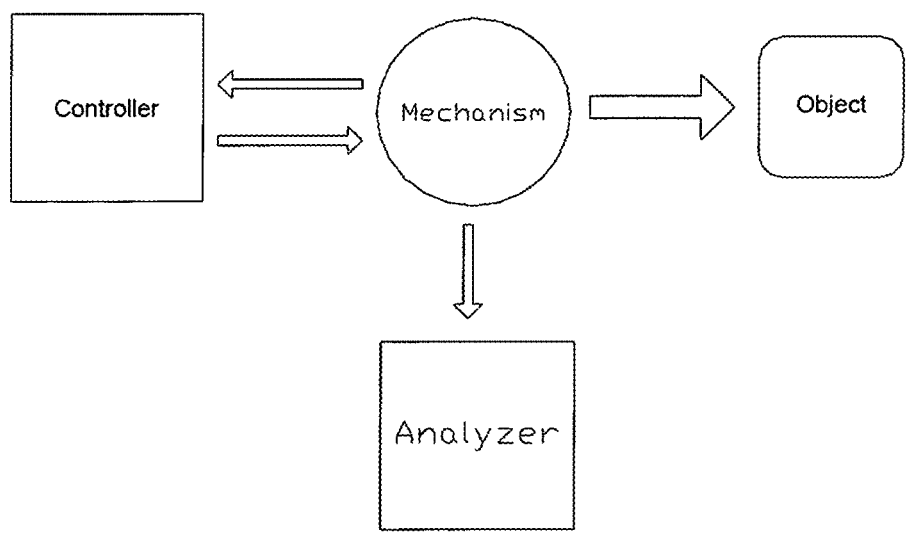
FIG. 1 illustrates the interrelations between subsystems of the system.

The presented invention, applies the method for characterization soft materials and biological tissues by means of a characterization system, whereas called system, which includes three main subsystems: analyzer, mechanisms and controller. The interrelations between the subsystems are shown in FIG. 1. The analyzer applies the method on the measurements which are taken place by mechanisms and controller, enables the mechanisms to perform the deformations and measurements required in order to characterize the object by analyzer according to the method. Each subsystem is described separately, and, where applicable, an example of characterizing an artificial object is performed in order to present functionality of the system in practice. First the analyzer and the method are explained, then mechanisms are introduced and finally controller will follow.

Analyzer

The characterization system deals with soft materials/objects in general term and with biological tissues as in-vivo objects. These materials include elastic/hyperelastic and viscoelastic/plastic materials, which can be classified in two categories as time-independent and time-dependent materials, respectively. The difference between viscoelastic and plastic material is the effectiveness of the hyperelastic element embedded in the material/object. In a viscoelastic material, the hyperelastic element drive the object to its initial stable status after deformation but in plastic material due to inefficient hyperelasticity, object remains at the deformed status. Nonlinear hyperelasticity and viscoelasticity analyses including analytical, finite element analyses and experimental based on incremental nonlinear approach were presented by Shabram ("A nonlinear approach for characterization of viscoelastic materials with application in tactile sensing for robotics and minimally invasive surgery", a thesis of MASc in Department of Mechanical and Industrial Engineering of Concordia University, Montreal, Canada, August, 2008). For describing the method the important parts of abovementioned reference is presented. The analytical and finite element analyses, nonlinear hyperelasticity and viscoelasticity wherever mentioned in this disclosure are referred to above mentioned incorporated reference.

Characterization of Viscoelastic Materials: Analytical Presented in the Referred Thesis In literature, various analyses of Maxwell and Kelvin-Voigt models are presented. All of these analyses use linear approach. In linear approach, superposition was the principal solution to establish material properties of unknown stiffness and damping coefficient (see next section). Though the elements in the abovementioned models show nonlinear behavior but for simplicity, nonlinear parts of their constitutive equations are omitted. Therefore, linear approach was used to solve the problem as linear viscoelasticity.

Simplification of the problems to linear approach saves costs and time. On the other hand, nonlinear approach, cost exponentially higher than linear ones due to their complexity. Some industries such as aerospace justify advantages of nonlinear approaches in order to obtain more precision, accuracy and safety.

The research presented mainly an analysis scheme for characterization of hyperelastic and viscoelastic materials based on nonlinear approach. This approach could be used in tactile sensing for characterization of tissues.

In this chapter, the incremental nonlinear solution is explained, nonlinear solution for hyperelastic material is presented and, a model of viscoelastic material and its solution are introduced. Finally, the proposed model is justified by using creep and relaxation behavior of viscoelastic materials.

Incremental Nonlinear Solution

Figure 2:
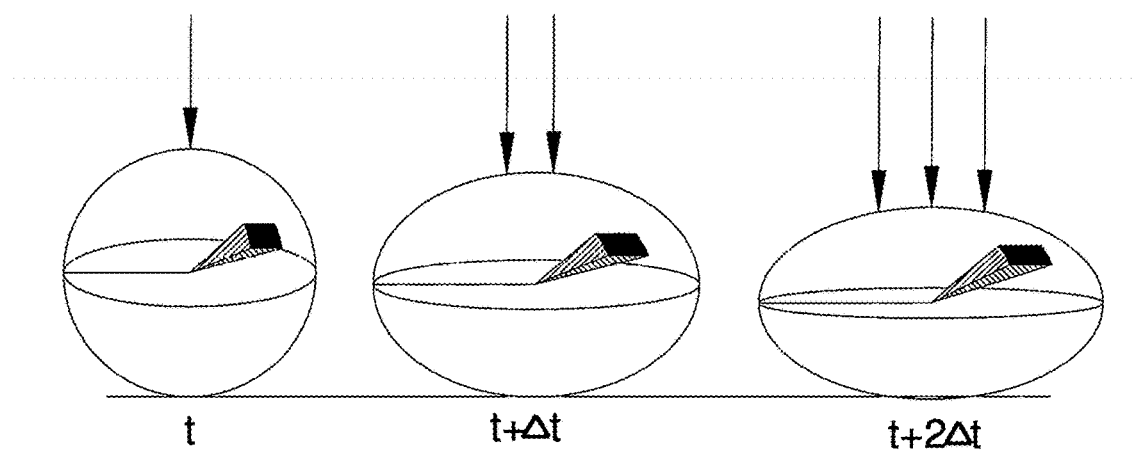
FIG. 2 illustrates incremental nonlinear approach

In nonlinear solution, first of all, constitutive equations are not simplified to linear terms. In another word, when independent variables in an equation are power of two or higher, their effects are taken into consideration, even though the result may not differ greatly from linear approach. Secondly, the effect of changes of geometry, boundary condition and properties are taken into account to update the configuration in time intervals. For example, any change in geometry of structure of a material changes its stiffness coefficient. Consequently, deformation under external force reorganizes the material molecular arrangement resulting change of material properties. In addition, deformation of the object under external force causes change of force orientation or direction. Based on the above mentioned concepts, two methods are common in nonlinear approach to take into account the changes of the configuration of the material. The first method compares the deformed configuration with the undeformed initial configuration that is called Total Lagrangian. In the second method, the new configuration is compared to the last updated one that is known as Updated Lagrangian. A very simple representation of a nonlinear approach is demonstrated in FIG. 2. As it is shown, the geometry of the object changes while the force is increasing and as a result, the stiffness of the object which is a function of geometry changes within the force. By comparing a small element on the object with respect to the deformation rate, the shape of the element shows considerable changes.

Hyperelastic and Viscoelastic Materials Analyses

Figure 3A:
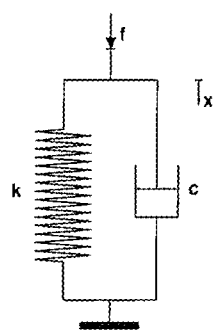
FIG. 3 illustrates Kelvin-Voigt Model (3A) and Maxwell Model (3B)

The simplest model for viscoelastic materials is Kelvin-Voigt model which consists of a spring and a dashpot. These two elements are shown in FIG. 3A.

Figure 3B:
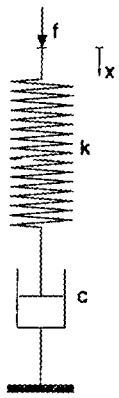

The behavior of the system is dependent on the stiffness of the spring and damping coefficient of the dashpot. Another simple model presented by Maxwell is shown in FIG. 3B.

Figure 4A:
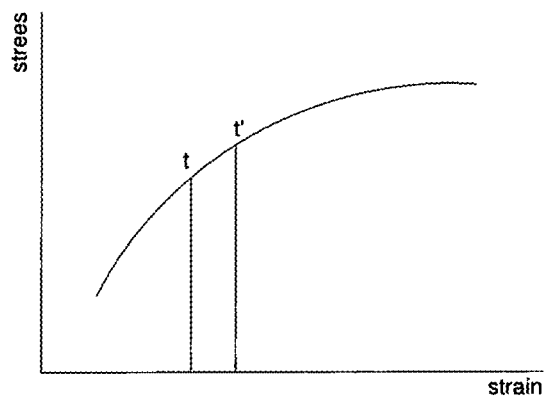
FIG. 4 illustrates stepwise stress-strain curve (4A) and One dimensional analytical results (4B)

In linear viscoelasticity, the characteristic of the material is interpreted by creep and relaxation behaviors. Each of the abovementioned models complies with one of the behaviors. Kelvin-Voigt model demonstrates creep and fails to show relaxation behavior while Maxwell model demonstrates relaxation and fails to show creep behavior. The combined models were also suggested to overcome this deficiency. To analyze nonlinearly viscoelacticity, Kelvin-Voigt model is used to explain the approach because it corresponds to both materials: hyperelastic (when damper coefficient is zero) and viscoelastic materials when both stiffness and damper coefficient are greater than zero. On the other hand, as it is shown in FIG. 4, Maxwell model can only behave like a hyperelastic material when damper coefficient approaches to infinity which is physically unaffordable. Therefore, the best mathematical model for starting the analysis is Kelvin-Voigt. For the model it can be written:

$$kx + c\dot{x} = f \quad (1)$$

Where k, c are spring constant and dashpot coefficient, respectively. For convenience with mechanical definition of stress, it can be written in the following form:

$$E\varepsilon + \mu\dot{\varepsilon} = \tau \quad (2)$$

where E, $\mu$ are elastic modulus and dynamic viscosity coefficient. $\varepsilon$, $\dot{\varepsilon}$ are strain and strain rate with respect to time, and $\tau$ is external stress.

One Dimensional Hyperelasticity

For analyzing hyperelastic material, it is considered that $\mu=0$, from equation (2) it results in:

$$E\varepsilon=\tau \quad (3)$$

From Energy Conservation Law, the one dimensional constitutive equation (neglecting body force for stationary condition) can be written:

$$\int \sigma \delta \varepsilon A dl = W_{external} \quad (4)$$

while $\sigma$, $\varepsilon$ are Cauchy stress and Green-Lagrange (GL) strain, respectively. A is area of section and dl is length of integral element. The GL strain is with respect to the deformed configuration. W is total external work given to system. At the arbitrary time step t=t' GL strain is:

$$\varepsilon = \frac{l^2 - l_0^2}{2l^2} \quad (5)$$

where $l_0$ is primary length and l is actual length. By considering the time step small enough, the area of the curve (FIG. 4A) with inconsiderable error and dividing W by A, area of the section, the equation (4) becomes:

$$\sigma \delta \varepsilon = \delta W_{external} \quad (6)$$

If the decrease in length of the material in the first step is considered as x the strain becomes:

$$\varepsilon = \frac{(l_0 - x)^2 - l_0^2}{2l^2} \quad (7)$$

Or:

$$\varepsilon = \frac{x^2 - 2xl_0}{2l^2} \quad (8)$$

Regarding small increment of the strain, E is assumed to be constant during time intervals, so equation (6) can be written as:

$$E\varepsilon^2 = \delta W_{external} \quad (9)$$

By introducing the strain of the step n and for simplification, assuming that deformation of every step is the same value, i.e. x, it results in:

$$\varepsilon_n = \frac{(l_0 - nx)^2 - (l_0 - (n-1)x)^2}{2(l_0 - nx)^2} \quad (10)$$

Consequently equation (9) can be written as:

$$E_n \varepsilon_n^2 = \delta W_n \quad (11)$$

where $\delta W_n$ is the nth step change of work. By calculating the external work and measuring deformation in every step $E_n$ can be determined.

From equation (11), $E_n$ is obtained in one dimensional problem. Since the real object is three dimensional, 3D model analysis of hyperelastic material is presented in the following section.

Figure 4B:
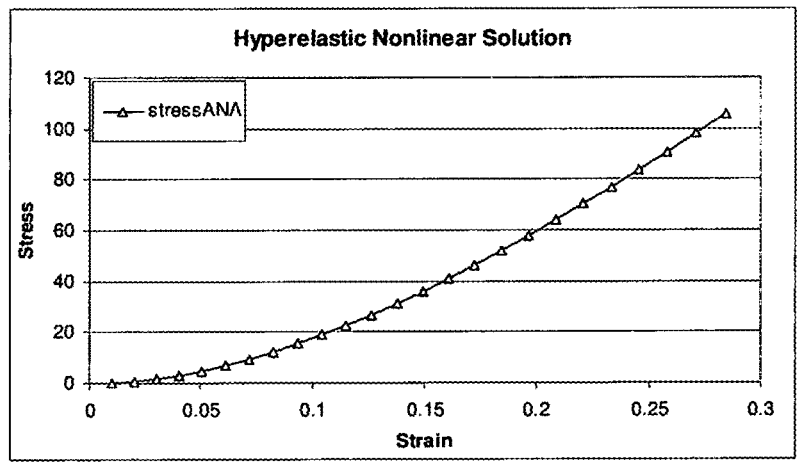

For simplification, the length of the analytical model was considered to be one and the final displacement is assumed 25% of the initial length. This assumption is also valid in tactile sensing as namely material does not deform more than 25% of its original length during grasping. FIG. 4B shows the stress-strain curve with a compressive ramp force. Therefore, any hyperelastic materials can be identified simply by measuring the force and deformation and analyzing the result of measurement through the nonlinear algorithm.

Three Dimensional Hyperelasticity

In the previous section, the method was described for a one dimensional model. In tactile sensing application, materials are deformed in three dimension, hence a three dimensional model is required.

Figure 5A:
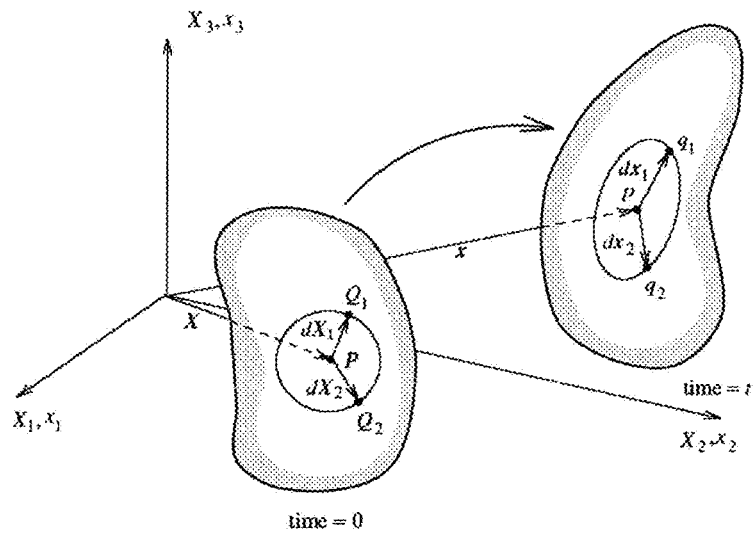
FIG. 5 illustrates deformation vectors (5A) and 3D element before and after deformation (5B)

Based on continuum mechanics FIG. 5A (Bonet, Wood (1997); "Nonlinear Continuum Mechanics For Finite element Analysis", Cambridge University Press) the deformation gradient is defines as:

$$F = \frac{\partial x}{\partial X} \quad (12)$$

Where $x=x(X,t)$ consequently Right Cauchy-Green Deformation Tensor becomes:

$$C = F^T F \quad (13)$$

The Green-Lagrangian strain tensor based on Right Cauchy-Green Deformation Tensor is:

$$E = \frac{1}{2}(C - I) \quad (14)$$

where C is Right Cauchy-Green Deformation Tensor and I identity matrix. Accordingly material derivative with respect to time lead us to velocity gradient:

$$l = \frac{\partial v(x, t)}{\partial x} = \nabla v \quad (15)$$

which results in deformation gradient rate:

$$\dot{F} = \frac{\partial v}{\partial X} = lF \quad (16)$$

Symmetric velocity gradient is calculated based on asymmetric tensor of l:

$$d = \frac{1}{2}(l + l^T) \quad (17)$$

Tensor derivation of equation 14:

$$\dot{E} = \frac{1}{2}\dot{C} = \frac{1}{2}(\dot{F}^T F + F^T \dot{F}) \quad (18)$$

Similarly, the rate of strain with respect to deformed configuration becomes:

$$\dot{\varepsilon} = \frac{1}{2}(I - b) \quad (19)$$

where b is Left Cauchy-Green Deformation Tensor. The Energy Conservation equation, by neglecting body force corresponding deformed volume v is:

$$\int_v (\sigma : d) dv_{volume} = \delta W_{external} \quad (20)$$

For very small time step $\sigma$ is considered to be constant in duration of time step, hence the integration is approximately equal to:

$$(\sigma : d) v_{volume} = \delta W_{external} \quad (21)$$

The equation (21) can be written for stationary condition as well. It means the object is at the static equilibrium:

$$(\sigma : \delta \varepsilon) v_{volume} = \delta W_{external} \quad (22)$$

Analysis of Nonlinear Viscoelasticity

In the present section, nonlinear approach is introduced to analyze a viscoelastic material. Since the material should be subjected to large deformation to show their time dependent behavior, a hyperelastic material have to be included in its model in addition to a viscous media which could be a fluid or a semi solid material. In another word, a viscoelastic material consists of a hyperealstic element, which is time independent and absorbs the energy to deform and releases it by removing the force, and a dissipating media, which absorbs energy by internal friction and wastes it through heat loss or increase of internal energy.

Considering two elements which are combined and assumed as a homogenous material, the relation of stresses in a viscoelastic material becomes:

$$\sigma_e + \sigma_v = \sigma_t \tag{23}$$

Where $\sigma_e$, $\sigma_v$ are elastic and viscous stresses and at is total stress. As elastic stress (compressive stress) is the same for solid and fluid, emphasis is put on viscosity stress.

Viscous Fluid

First of all, material time derivative of a field variable (any field variable) is the key point for establishing a proper relation between properties of a fluid and its status which is:

$$\frac{D(\ )}{Dt} = \frac{\partial(\ )}{\partial t} + V \cdot \nabla(\ ) \tag{24}$$

Where V is velocity field vector. From Newton Second Law momentum equation for a field flow can be written as:

$$\frac{DV}{Dt} = \frac{\partial V}{\partial t} + (V \cdot \nabla)V = F_f/\rho \tag{25}$$

where $\rho$ is the density of fluid. Since the force $F_f$ is:

$$F_f = -\nabla P + \nu \nabla^2 V \tag{26}$$

By substituting in the equation (22) It results in:

$$\frac{\partial V}{\partial t} + (V \cdot \nabla)V = \frac{-1}{\rho}\nabla P + \frac{\nu}{\rho}\nabla^2 V - g e_z \tag{27}$$

where $e_z$, $\upsilon$ are the elevation from reference level (zero level) and kinematics viscosity, respectively. The momentum equation can be written as well;

$$\rho \frac{\partial V}{\partial t} = -\nabla P + \nabla T' + \rho f \tag{28}$$

where f is gravity or body force which is neglected in this study. Fluid stress T' can be defined as:

$$T' = \lambda(\nabla \cdot V)I + \mu(\nabla V + \nabla V^T) \tag{29}$$

where $\mu$, $\lambda$ are first and second viscosity coefficients. As it is implied by equation (29) the viscosity stress is a function of partial derivatives of velocity or simply a function of spatial material status and time while elastic stress is function of only spatial material status. In another word, viscosity stress depends on changes of material spatial status regarding the rate of changes but elastic stress is simply dependent on material changes disregarding its rate.

In the same manner, from Energy Conservation or First law of Thermodynamics it can be written:

$$\frac{dE}{dt} = \text{Workrate} + \text{Heatsource} \tag{30}$$

And in an extensive manner, it can be written as:

$$\rho \frac{de}{dt} = -p\nabla \cdot V + \phi - \nabla q \tag{31}$$

Where e, $\phi$, q are total energy per unit mass, dissipation energy and heat transfer, respectively. Since there is no heat source and body force is neglected, last two terms of the above equation can be omitted. Viscous energy dissipation function can accordingly be written as:

$$\phi = T:(\nabla V)^T = tr(T(\nabla V)^T) \tag{32}$$

By considering stretch tensor and deviatoric stretch tensor as:

$$D = \frac{1}{2}(\nabla V + (\nabla V)^T) = D^T \tag{33}$$

$$D' = D - tr(D) \cdot I/3 \tag{34}$$

Where I is unit matrix, dissipation function becomes:

$$\phi = \frac{1}{2}(\mu_0(tr(D))^2 + \mu(tr(D'))^2) \tag{35}$$

Where $$\mu_0 = \lambda + \frac{2}{3}\mu.$$

Since it is assumed that the viscous fluid is incompressible or the compressibility is negligible, the dissipation function for volume-preserving fluid results in:

$$tr(D) = \nabla \cdot V \tag{36}$$

$$tr(D') = 0 \tag{37}$$

Combined Hyperelastic Solid and Viscous Fluid

Having studied hyperelastic solids and viscous fluids, it can be proceed to viscoelastic material as a combination of these elements.

Since the derivative of both terms with respect to time exist, from equation (23), the rate of change of their sum during deformation results in:

$$\frac{d}{dt}(\sigma_e + \sigma_v) = \frac{d}{dt}\sigma_t \tag{38}$$

For simplification, mathematical model of Kelvin-Voigt, which is expressed in equation (2), is considered as a combination of a simple hyperelastic (spring) and a viscous (dashpot) element while it should be taken into account that E, $\mu$, contrary to linear viscoelasticity, are not constant. The derivation of equation (2) with respect to time becomes:

$$\frac{d}{dt}(E\varepsilon) + \frac{d}{dt}(\mu\dot{\varepsilon}) = \dot{t} \tag{39}$$

As it was mentioned before, in nonlinear approach the properties of the material are not assumed constant, consequently they are considered as an independent variable. Based on this consideration, it can be written:

$$\frac{dE}{dt}\varepsilon + \frac{d\varepsilon}{dt}E + \frac{d\mu}{dt}\dot{\varepsilon} + \frac{d\dot{\varepsilon}}{dt}\mu = \tau \quad (40)$$

Using incremental nonlinear approach, small time interval for updating the configuration of the material is taken. For small time interval E, μ are considered to be constant during deformation time steps. Therefore, the first and third terms are omitted from the left side of equation (40), hence:

$$E\dot{\varepsilon} + \mu\ddot{\varepsilon} = \tau \quad (41)$$

From the equation above, it can be concluded that the rate change of external force induces strain rate. The rate change of strain is dependent on material properties. In endoscope tactile sensing, where tissue is grasped by an endoscopic tool, properties of the grasped tissue can be determined by analyzing the data of measurement of applied force and of resulting displacement with respect to time. By measuring force and displacement (deformation) of the material with respect to time, all parameters in equation (2) and (41) are known except two unknown material properties E, μ, which are target results of the solution of tactile sensing problem.

Modeling of the Grasped Tissue During Endoscopic Surgery and Robotics

Figure 5B:
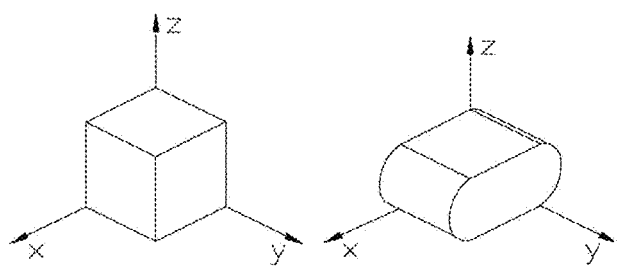

Despite the simplicity of the proposed approach, in general, the implementation is much more complicated when 3D model should have to be dealt with. Therefore, for simplicity it is assumed that a force could be applied only in one direction (z axis) and strains in other two orthogonal directions, i.e. x and y, are zero. Hence, elastic strain is considered only in z direction while velocity of viscous fluid could be also considered only in x direction. The schematic of 3D model before and after deformation is illustrated in FIG. 5B. Naturally, there is a one dimensional elastic problem (z direction) and a two-dimensional fluid problem (x-z plan) to solve.

Figure 6A:
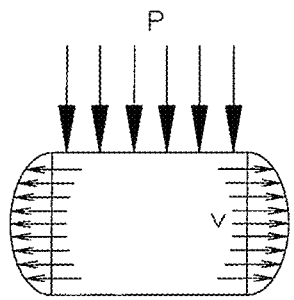
FIG. 6 illustrates velocity gradient of viscous fluid (6A) and elastic wall behavior due to deflection, a) membrane b) fixed-fixed plate (6B) and results of one dimensional analytical solution (6C)

Velocity gradient of viscous fluid under pressure of external force is depicted in FIG. 6A.

Figure 6B:
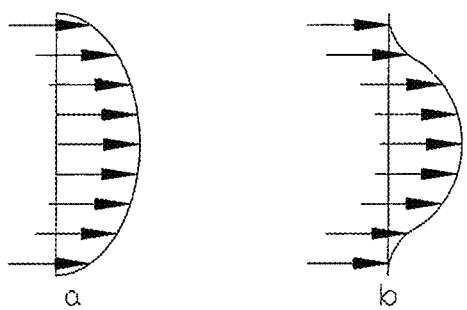

To calculate velocity gradient, the nature of the boundary of the object is requires to be determined. This is done by assuming two sides of elastic wall as a membrane. It will result in a slightly different profile if it is assumed as fixed-fixed plate. This assumption introduces a slightly different profile based on the size of the wall. On the other hand, since the fluid is considered incompressible, the volume after deformation is the same as initial configuration, i.e. the volume is preserved. In compression deformation, the profile might be the same as what is shown in FIG. 6B(a), and FIG. 6B(b) or combination of them, depending on the structure of the object. Evidently, more precise determination could be made by tests or further study of material structure to minimize produced error. It should also be taken into account that when internal pressure increases the deflection of the wall might show nonlinear behavior. For a low pressure limit it is likely to behave as a fixed-fixed plate and for higher pressure it behaves likely as a membrane due to deflection. In any case, either of these models might be used.

The next challenge that has to be confronted in 3D model is the direction of elastic and viscous stress. As it was mentioned in the present section, external stress is applying in z direction. Consequently, there is no elastic stress in x and y direction while viscous stress is in opposite direction of fluid flow in x direction. In 3D model, it is required to normalize the stresses to build up the required results and obtain applicable equations. As it was previously mentioned, in one dimensional mathematical model, the entire force could be interpreted as total stress while in 3D model total stress will change with respect to time (considering the behavior of the material). Hence, normalization of the entire stresses by energy conservation method is required. It leads to separate total given energy, to energy absorbed by viscous media and potential energy stored in elastic element:

$$W_e + W_v = W_{total} \quad (42)$$

$W_e$ is elastic energy, $W_v$ is viscous dissipated energy and $W_{total}$ total energy given to system. As it was mentioned before, the work done on the viscous media depends on the rate of velocity of viscous media. Consequently, it depends on the rate of change of external force. It can be concluded that it is a function of the slope of force-time curve while the potential elastic work is only dependent on strain. In another word, elastic stress depends on the magnitude of the external force and it is not therefore dependent upon the rate of change with respect to time. Since the velocity profile have to be determined by using pressure distribution of the fluid on the elastic wall and with assumption of volume preserving fluid, velocity of the media, as a field vector, can be obtained by considering measured displacement with respect to time. Hence, viscous absorbed energy rate of incompressible fluid can be obtained by:

$$\frac{DW_v}{Dt} = \phi = tr(\sigma_v(\nabla v)^T) \quad (43)$$

where $\phi$, $\sigma_v$ and $W_v$ are dissipation function, viscosity stress and energy absorbed by viscous media, respectively. The elastic potential energy is thus the result of subtraction of two time dependent, energy producing and energy consuming sources as follow:

$$W_e = W_{total} - \int_{t_1}^{t_2} \phi dt \quad (44)$$

As elastic potential energy is obtained, elastic modulus can be calculated. The procedure was discussed in hyperelastic solution.

The model can be applied not only for a simplified 3D model but generally for all real models while the assumptions should be taken into account that the viscous media is isochoric and elastic element is isotropic material.

Figure 6C:
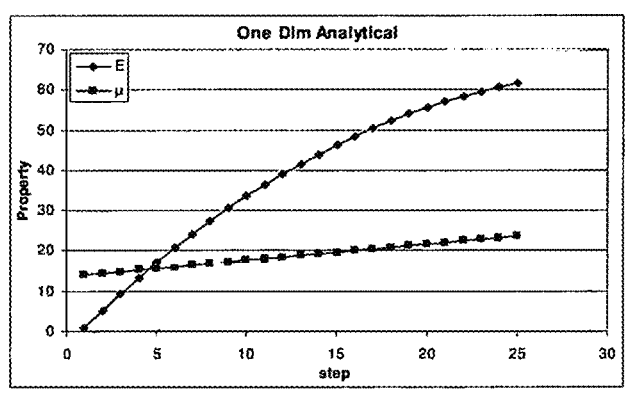

By applying an external ramp force to the one dimensional model and by considering the displacement 25% of initial length and all dimensions one, the analytical (mathematical) solution was obtained which is shown in FIG. 6C. The procedure is explained in previous section. The difference of magnitude of properties is shown to emphasis on the solution based on energy conservation method. In one dimensional analytical model, the integration of the energy is done on the length.

In the present analysis, the time of steps was fixed while assuming that the displacement is a constant function of time. In another word, it was assumed that the material shows a constant rate of deformation in the z direction. Evidently, the viscosity coefficient is increasing according to the increase of force. It means that by increasing the force rate, the object resists more to keep the velocity constant, as it is the same behavior of a dashpot.

Justification of the Proposed Viscoelastic Analysis for Creep and Relaxation

In the present section, the creep and relaxation behaviors, as two major characteristics in linear viscoelasticity analyses, are discussed, and justified by proposed model and approach. Furthermore, the proposed approach provides the explanation for the nature of creep and relaxation behaviors.

Creep

Creep means that the strain of material increases with time when external stress remains constant after having applied the force and a resulting deformation. Meanwhile, the behavior of the material up to that stage is ignored. In linear viscoelasticity, it is costumed to neglect the time of applying force and considering it as a sudden force (step force) at time zero. In linear viscoelasticity, Volterra equation is used to separate stress and strain. For simplicity, analytical model of equation (2) is chosen to explain the creep. It is considered that viscosity stress is function of $\varepsilon$ while in reality $\varepsilon$ is not equal to $\partial v_i/\partial x_j$. Keeping the external stress constant at the final step, rate of stress change of equation (2) by derivation with respect to time results in:

$$E\dot{\varepsilon} + \mu\ddot{\varepsilon} = 0 \quad (45)$$

By solving ordinary second order differential equation (45) for $\varepsilon, \dot{\varepsilon}$ it results:

$$\dot{\varepsilon} = \dot{\varepsilon}_1 e^{-\frac{\mu}{E}t}, \varepsilon = -\frac{E}{\mu}\dot{\varepsilon}_1 e^{-\frac{\mu}{E}t} + \frac{E}{\mu}\varepsilon_1 \quad (46), (47)$$

Figure 7A:
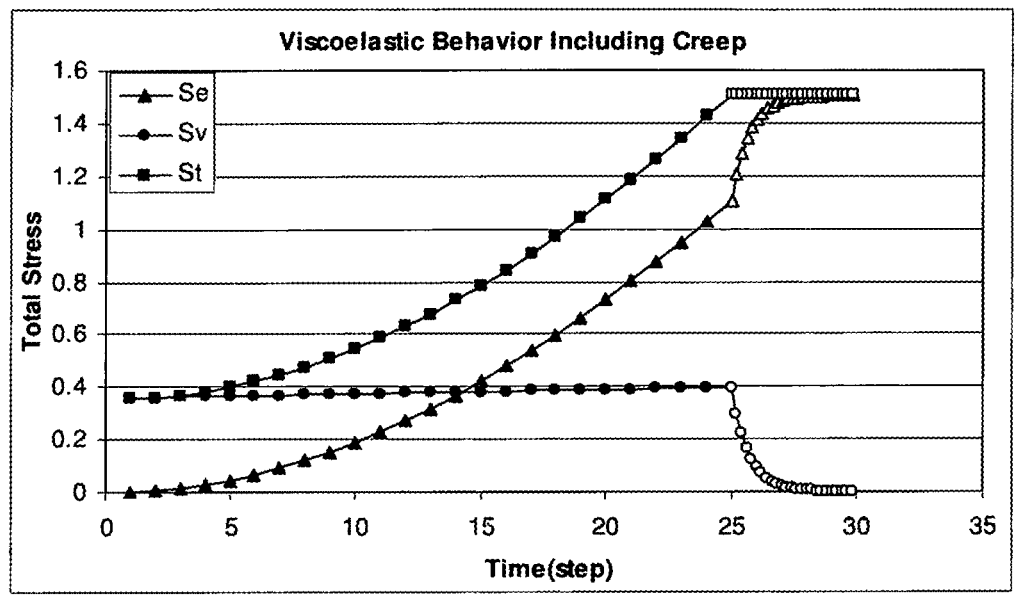
FIG. 7A illustrates viscoelastic material solution including creep (7A) and membrane equilibrium with viscous fluid a) before, b) during and c) after relaxation (7B)

Therefore, the total internal stress of the material in the absence of external stress can be obtained by sum of elastic and viscous stresses as:

$$E\left(\varepsilon_1 + \frac{E}{\mu}\varepsilon_1 - \frac{E}{\mu}\dot{\varepsilon}_1 e^{-\frac{\mu}{E}t}\right) + \mu\dot{\varepsilon}_1 e^{-\frac{\mu}{E}t} = \tau_{total\ internal} \quad (48)$$

where $\varepsilon_1, \dot{\varepsilon}_1$ are strain and its rate at the time that external stress changes to constant. FIG. 7A shows total, viscous and elastic stress including the creep behavior. As it is shown, the $S_e$, $S_v$ and $S_t$ with indicator solid are elastic, viscous and total stresses (which will be discussed in next chapter) before creep, and the same with blank indicators are the stresses during creep.

Relaxation

Relaxation is defined as the decrease of stress in a viscoelastic material when strain is maintained constant after reaching to a certain level. Explanation of relaxation behavior requires that the nature of viscoelastic material model be studied with respect to the interaction between hyperelastic part and viscous media. The model is shown in FIG. 3A. Though in linear viscoelasticity, the relaxation is explained on the Maxwell model which is shown in FIG. 3B, the Kelvin-Voigt model is used to explain it. As it is shown in FIG. 3A, neither elastic spring, nor viscous damper shows relaxation behavior individually. In addition, they do not show relaxation behavior together because in the model they do not have any direct contact contrary to what happens in viscoelastic materials. In dashpot, the viscous stress immediately disappears when its generating force is cancelled (neglecting inertia of the piston respect to the viscous force. This is especially valid when the strain is constrained that prevents the piston from moving). Therefore, the relaxation in two-dimensional model, which is shown in FIG. 6A, can be studied by considering the simplicity of one directional strain and one directional flow. Considering equation (23) and implementing the simplification results in:

$$E\varepsilon + \mu\frac{\partial v_x}{\partial y} = \tau \quad (49)$$

where $\partial v_x/\partial y$, $\tau$ are velocity gradient and external stress, respectively. According to the definition of relaxation, at the stop point, the strain is maintained constant. Therefore, the external stress consists of the elastic stress which is constant and the viscous stress. Consequently, the equation (49) can be written as:

$$E\varepsilon + \mu\frac{\partial v_x}{\partial y} = E\varepsilon + \sigma_v \quad (50)$$

The elastic stress can be omitted from both sides of the equation, so the change rate of viscous flow can be obtained by derivation of both sides with respect to time.

$$\frac{d}{dt}\left(\mu\frac{\partial v_x}{\partial y}\right) = \dot{\sigma}_v \quad (51)$$

Figure 7B:
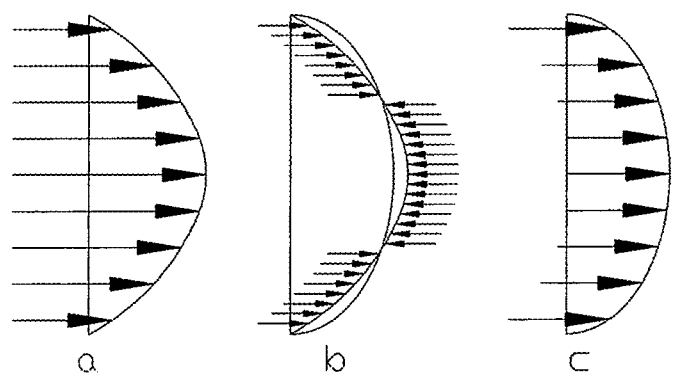

Considering elastic part of viscoelastic material model, there are two elastic elements which are hyperelastic: one acts in the direction of the applied force and the other is the resistant of the elastic membrane against the viscous flow. It should be mentioned that the compressibility of viscous fluid was neglected. However, it was considered that viscous fluid is incompressible (which is negligible comparing to hyperelasticity) for solving the problem only for first viscosity coefficient, it can be taken into account for further study. At the stop point of external force to maintain strain constant, the second term of fluid pressure becomes zero (FIG. 7B(a)) and the reaction force of elastic membrane F(x, y) becomes unbalance with static pressure (FIG. 7B(c)) that constitute external force to move the viscous fluid to form new stable balance configuration (FIG. 7B(b)).

$$P_0 + \mu\frac{\partial v_x}{\partial y} \quad \frac{d}{dt}\left(\mu\frac{\partial v'_x}{\partial y} + \frac{\partial v'_y}{\partial x}\right) \quad P_0$$

By assuming that at the new equilibrium configuration, membrane force is P(x, y) and neglecting body force, the partial differential equation could be written:

$$F(x, y) - P(x, y) - \mu\left(\frac{\partial v'_x}{\partial y} + \frac{\partial v'_y}{\partial x}\right) = 0 \quad (52)$$

Figure 8:
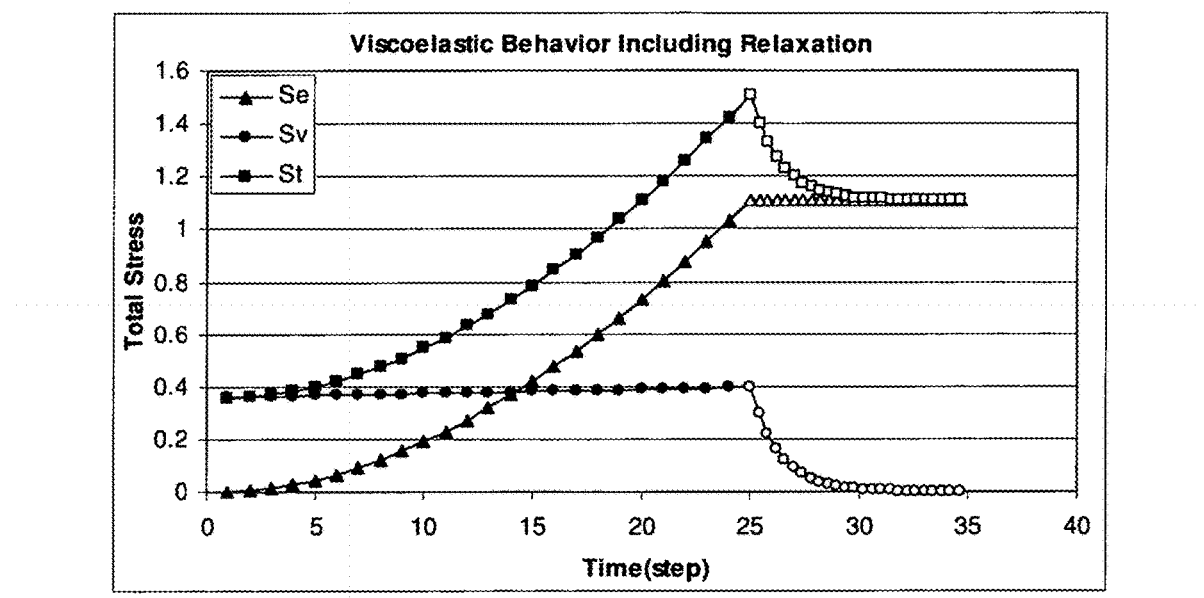
FIG. 8 illustrates viscoelastic material solution including relaxation

$v'_x$, $v'_y$ are velocities of viscous media. The partial equation with known boundary conditions may have a solution by numerical method which is not the present case. Therefore, it is possible to guess a solution globally for viscous stress that satisfies the boundary condition. The solution could be in the form of:

$$\sigma'_v = -F(x,y)e^{-\lambda t} + P(x,y) \quad (53)$$

where $\lambda$ depends on viscosity coefficient and elastic membrane stress. FIG. 8 shows the elastic, viscous and total stresses of the model with 0.1 mm/sec. deformation rate. It shows how the total stress reaches to elastic stress during relaxation time. It presents total, viscous and elastic stresses including the relaxation behavior. $S_e$, $S_v$ and $S_t$ with solid indicator are elastic, viscous and total stresses (which will be discussed in next chapter) before relaxation and the same with blank indicators are the stresses of relaxation.

Summary of Analytical

As a summary, the incremental nonlinear solution was introduced and used to develop one and three dimensional hyperelasticity solutions. In addition, viscoelastic material model was introduced by combining hyperelastic and viscoelastic elements. Finally the behavior of viscoelastic material was justified by the proposed model.

Finite Element Analysis of Viscoelastic Materials

In this section, the criteria for selecting appropriate element are discussed. The finite element solutions for solid and fluid element are also presented. Finally the results are discussed.

Finite Element Formulation and Modeling

Although the present approach seems simple, its implementation is much more complicated especially when a 3D model is used for viscoelastic material. Therefore, as it was mentioned in the previous chapter, the simplifications are required to be taken place. For simplicity it is assumed that the compressive force is applied only in z direction and strain in both x and y directions is zero. Hence, elastic strain is considered only in z direction while velocity of viscous fluid is also considered only in x direction. The proposed simplifications are based on the nature of the force applied and deformation produced in tactile sensing applications. The 3D model of viscoelastic material before and after deformation is depicted in FIG. 5B. Therefore, the 3D model is converted to 2D model by assuming that the deformation is zero in the y direction.

Having concluded that the required element should be two dimensional, the appropriate element should be selected regarding the principal criteria in finite element method.

In finite element method approximation of displacement is done on the element region via variation of the variable by:

$$u = \sum_{i=1}^{n} u_i \psi_i \quad (51)$$

Where u is displacement and $\psi_i$ is interpolation function regarding node ith. For two dimensional problems we have:

$$\psi_i(x_j, y_j) = \delta_{ij} \quad (52)$$

where $\delta_{ij}$ is zero everywhere except node ith. The interpolation (shape) function is determined based on the polynomial approximation which is dependent of the element shape and number of nodes. In this regard, element shape is the first priority to be determined. The shape of element depends on the model, geometry, boundary condition and the precision of the results. The most common elements for 2D are triangular and rectangular elements. The other factor to determine the appropriate element is the number of nodes on the element region. The behavior of the element is dependent on the number and layout of the nodes.

Three node triangular element leads to a bilinear function with respect to x and y which is linear with respect to both. It means the function behave linearly with respect to variables of x and y.

In the same manner, interpolation functions for a four node rectangular element can be found. In this regard, the degree of polynomial approximation is determined by Pascal's triangle and rectangular array.

By comparing interpolation functions of both elements, it can be concluded that the approximation of a triangle is linear with respect to x and y while rectangular approximation function has a bilinear term of x and y. The approximation functions are used to analyze the variation of strain and consequently stress within the element. By assuming that both elements are subjected to displacement along x axis, the displacement function becomes:

$$u_x(x, y) = \sum_{i=1}^{n} u_{xi} \psi_i(x, y) \quad (67)$$

Since the strain is the derivation with respect to x, it results in:

$$\varepsilon_x = \frac{\partial}{\partial x} u_x(x, y) = \frac{\partial}{\partial x} \sum_{i=1}^{n} u_{xi} \psi_i(x, y) \quad (68)$$

and according to the derivative property of sum above, it results in:

$$\varepsilon_x = \sum_{i=1}^{n} \frac{\partial}{\partial x} u_{xi} \psi_i(x, y) \quad (69)$$

Since the displacements of the nodes are constant, they are excluded from differentiation:

$$\varepsilon_x = \sum_{i=1}^{n} u_{xi} \frac{\partial}{\partial x} \psi_i(x, y) \quad (70)$$

For triangle element, it can be written:

$$\varepsilon_x = \sum_{i=1}^{n} u_{xi} \frac{\partial}{\partial x} \left[ \frac{1}{2A_e} (\alpha_i + \beta_i x + \gamma_i y) \right] \quad (71)$$

which results in:

$$\varepsilon_x = \sum_{i=1}^{n} u_{xi} \beta_i = const. \quad (72)$$

while the same procedure for four node rectangular element leads to:

$$\varepsilon_x = \sum_{i=1}^{n} -u_1\left(1 - \frac{y}{b}\right) + u_2\left(1 - \frac{y}{b}\right) + u_3 \frac{y}{b} - u_4 \frac{y}{b} \quad (73)$$

and:

$$\varepsilon_x = f(y) \quad (74)$$

which means that the strain in x direction is not constant in y direction. The procedure of derivation of interpolation functions of triangular and rectangular elements with different number of nodes is presented in related text books. Therefore, the element shape selection affects the result consistency of finite element solution. In this regard, it is required to increase the precision by using h method, i.e. higher order element. Consequently, one node is added to the nodes of side lines in the middle. By adding three nodes to triangular element, three more terms are introduced which creates the polynomial with one degree higher that means the strain degree increases one degree too. In the same manner, by introducing one node in the middle of rectangular side, four terms will be added to the interpolation function, and by adding one node in the center of the rectangular, the fifth term will be added. Consequently, the interpolation function is in the degree of four with respect to both variables of x and y.

Therefore, it can be concluded that for having an element to show nonlinear strain along element axes, at least, quadratic element is required. In addition, element shape is required to be chosen between triangular and rectangular. In this regard attention has to be paid to the application of the element.

For tactile sensing application, the objects are manipulated by touch. More precisely, they are manipulated with applying force in compressive manner or contact force in sliding manner. The latter one is namely considered for texture/roughness detection. For softness analysis, vertical compressive load need to be applied. Therefore, the attention is concentrated on compressive force. The force boundary condition in the manner of compressive force requires distributed force or pressure on the surface of the object. To apply a compressive force or pressure, two parallel surfaces are required: one the supporting surface and the other for applying the pressure. A Compressive force is naturally applied to an object via a probe or similar apparatus which should have a limited contact area with the material. The contact surface is always considered flat that means there is no irregularity within the shape of model. Consequently, triangular element is not required to deal with shape of the object. On the other hand rectangular element provides the flat contact surface naturally. Regarding what was mentioned for the consideration of strain and manner of applying force, the model should consist of rectangular quadratic element(s).

Figure 9A:
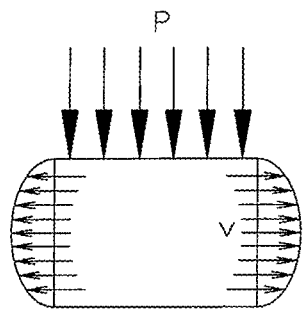
FIG. 9 illustrates viscous flow acting on the membrane (9A) and viscous flow gradient on a quadratic element (9B) and Serendipity cubic element (9C)

There is one more consideration that is required to be taken into account and that is the order of the element. The model of viscoelastic material consists of a viscous media as well as a hyperelastic material. The element of the model should comply with fluid properties. Regarding to deformation of the model, the viscous media flows through the model under the pressure of external applied force (FIG. 9A).

Figure 9B:
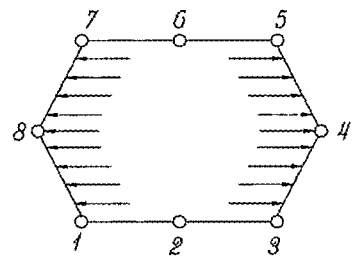

Since the compressive force is applied in z direction, the flow of the media takes place in x and y directions. In this regard, it is required to establish velocity gradient based on the deformation profile. Therefore, enough nodes are needed on the sides to interpolate the velocity profile. As it is shown in FIG. 9B, the three nodes side wall of the element results in a linear triangular velocity profile. Therefore, minimum of 4 nodes at every side of the element have to be selected to deal with velocity profile and gradient. Consequently, the simplest element for the model becomes a 13 node element.

Since the center (internal) node does not contribute to the element continuity and also in tactile sensing problem, the displacements of internal nodes are not measured during the deformation, it can be eliminated from the element. The displacement of internal nodes cannot be measured because they are not accessible by any means in order to be measured. This kind of Lagrange family without internal nodes are called serendipity element.

For numerical computation purpose, it is more appropriate to use the following transformation for x and y in rectangular element functions:

$$\xi = \frac{2(x-x_i)-a}{a}, \eta = \frac{2(y-y_i)-b}{b} \tag{81}$$

Therefore, the first interpolation functions based on isoparametric cubic element becomes:

$$\psi_1 = \frac{1}{4}(1-\xi)(1-\eta)\xi\eta \tag{82}$$

Figure 9C:
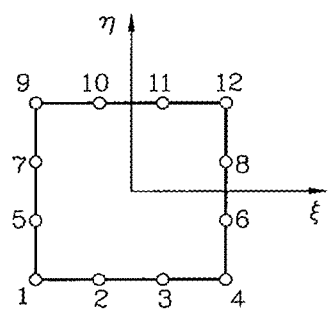

The 12 node serendipity element is shown in FIG. 9C. The interpolation functions of this cubic element are derived in the same manner as it was mentioned for quadratic element. The detail procedure of derivation of interpolation functions is explained in text books.

Figure 10A:
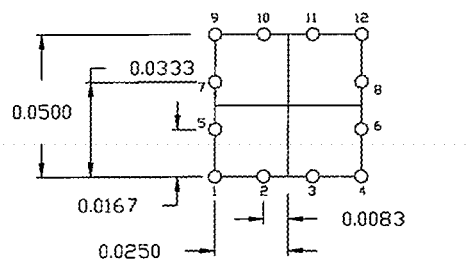
FIG. 10 illustrates model geometry (10A) and model geometry after deformation (10B)

As it is shown, the origin of the transformation coordinates is placed in the center point of the element. Therefore, the coordinates can be used for mapping the element to master element. The transformation allows that the numerical integration take place. The interpolation functions of cubic rectangular element are presented in text books Having selected the element, the necessity of meshing the model should be investigated. In finite element method, meshing the model is performed due to irregularity of geometry, lack of uniformity in boundary condition such as constraints, concentrated force, and precision required for critical region of model, simplification of the analysis, etc. The simplification of the model has obviated the criteria for meshing. On the other hand, the model for tissue is considered to be small dimensions. Therefore, to make the finite element less complicated the model consisting of only one element is considered. The model for which the solution is applied is shown in FIG. 10A. All dimensions are in meter and as it was mentioned before, it is assumed that the dimension perpendicular to the plane is completely undeformed. It should be mentioned that the dimensions of the model are determined according the experimental model which can be tested by test machine.

Figure 10B:
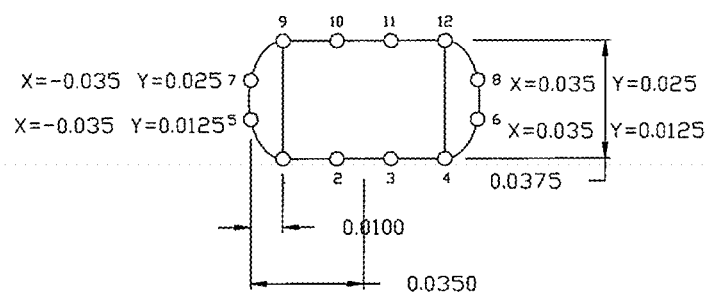

After deformation under external force and internal flow of viscous media, the model deforms as shown in FIG. 10B. In both models the origin is placed on the middle of bottom side, between node 2 and 3.

Regarding the shape functions, the coordinates of every node is calculated by:

$$x = \sum_{i=1}^{n} x_i \psi_i(x, y), y = \sum_{i=1}^{n} y_i \psi_i(x, y) \tag{87}$$

Eventually the coordinate of the respective node on the master element is obtained by the following equations:

$$x = \sum_{i=1}^{n} x_i \psi_i(\xi, \eta), y = \sum_{i=1}^{n} y_i \psi_i(\xi, \eta) \tag{88}$$

Consequently, by using the chain rule, the relation between transformed functions of x and y to functions of $\xi$ and $\eta$ is obtained as:

$$dx = \frac{\partial x}{\partial \xi} d\xi + \frac{\partial x}{\partial \eta} d\eta, dy = \frac{\partial y}{\partial \xi} d\xi + \frac{\partial y}{\partial \eta} d\eta \tag{89}$$

By arranging it into matrix form it results in:

$$\left\{\begin{array}{c} dx \\ dy \end{array}\right\} = \begin{bmatrix} \frac{\partial x}{\partial \xi} & \frac{\partial x}{\partial \eta} \\ \frac{\partial y}{\partial \xi} & \frac{\partial y}{\partial \eta} \end{bmatrix} \left\{\begin{array}{c} d\xi \\ d\eta \end{array}\right\} = [J]^T \left\{\begin{array}{c} d\xi \\ d\eta \end{array}\right\} \quad (90)$$

where [J] is the jacobian matrix which relates the elemental area of the transformation by:

$$dA = dx \cdot dy = J d\xi \cdot d\eta \quad (91)$$

where J=det[J]. Having transformed the elements before and after deformation to master element and using quadrature formulae and Gauss points, the integration over element area changes to algebraic operations:

$$\int_{\Omega_R} F(\xi, \eta) d\xi \cdot d\eta = \sum_{i=1}^{m} \sum_{j=1}^{n} F(\xi_i, \eta_j) W_i W_j \quad (92)$$

In the same manner, the derivation of any function with respect to variables of elements transformation can be calculated by using chain rule and jacobian as:

$$\left\{\begin{array}{c} \frac{\partial \psi_i}{\partial x} \\ \frac{\partial \psi_i}{\partial y} \end{array}\right\} = [J]^{-1} \left\{\begin{array}{c} \frac{\partial \psi_i}{\partial \xi} \\ \frac{\partial \psi_i}{\partial \eta} \end{array}\right\} \quad (93)$$

The model of FE can be applied by taking into account the consideration that the FEM for solid and fluid have some differences. Next sections will deal with the differences involved in analysis of FEM for solid and fluid.

Finite Element Method for Solid

In solid problems stress and strain are required to be calculated. Therefore, displacement is the independent variable which is used to calculate the strain. Finally the stress will be determined using strain and material property. In regular finite element, for determining displacement, all dependent variables, which are strain and stress, are substituted by functions of displacement. When the problem is solved for displacement, the strain and consequently, stress is calculated by mean of their function of displacement. The same procedure is used in the current problem except that the displacement is calculated by measuring the deformation. The deformation of the element is determined by geometry of the nodes before and after deformation. It is considered that the element is subjected to an external force resulting deformation with initial coordinates of nodes $X_0 = x_i^0 \psi_i(x, y)$ and deformed element with nodes coordinates $X = x_i \psi_i(x, y)$. By considering the deformation $u_{xi}$ in x direction and $u_{yi}$ in y direction, it results in:

$$u_{xi} = x_{xi} - x_{xi}^0, u_{yi} = y_{xi} - y_{xi}^0 \quad (94)$$

The equation can be written as:

$$X = X_0 + U \quad (95)$$

Consequently, the deformation gradient can be calculated by:

$$F = \frac{\partial X}{\partial X_0} = \frac{\partial}{\partial X_0}(X_0 + U) = 1 + \frac{\partial U}{\partial X_0} \quad (96)$$

Since both initial and deformed elements are transformed to master element, it is required to calculate the deformation gradient with respect the variable of master element. Therefore, by using chain rule, it results in:

$$\frac{\partial x}{\partial \xi} = \frac{\partial x}{\partial x^0} \frac{\partial x^0}{\partial \xi} + \frac{\partial x}{\partial y^0} \frac{\partial y^0}{\partial \xi} \quad (97)$$

$$\frac{\partial x}{\partial \eta} = \frac{\partial x}{\partial x^0} \frac{\partial x^0}{\partial \eta} + \frac{\partial x}{\partial y^0} \frac{\partial y^0}{\partial \eta} \quad (98)$$

By arranging them into matrices:

$$\left\{\begin{array}{c} \frac{\partial x}{\partial \xi} \\ \frac{\partial x}{\partial \eta} \end{array}\right\} = \begin{bmatrix} \frac{\partial x^0}{\partial \xi} & \frac{\partial y^0}{\partial \xi} \\ \frac{\partial x^0}{\partial \eta} & \frac{\partial y^0}{\partial \eta} \end{bmatrix} \left\{\begin{array}{c} \frac{\partial x}{\partial x^0} \\ \frac{\partial y}{\partial y^0} \end{array}\right\} \quad (93)$$

By repeating this procedure for y the deformation gradient for 2D becomes:

$$F = [J^0]^{-1}[J] \quad (93)$$

where:

$$[J^0] = \begin{bmatrix} \frac{\partial x^0}{\partial \xi} & \frac{\partial x^0}{\partial \eta} \\ \frac{\partial y^0}{\partial \xi} & \frac{\partial y^0}{\partial \eta} \end{bmatrix}, [J] = \begin{bmatrix} \frac{\partial x}{\partial \xi} & \frac{\partial x}{\partial \eta} \\ \frac{\partial y}{\partial \xi} & \frac{\partial y}{\partial \eta} \end{bmatrix} \quad (94)$$

Therefore, in every step, the strain with respect to the last updated configuration can be calculated by:

$$\varepsilon = \tfrac{1}{2}(I - b) \quad (95)$$

Finite Element Method for Fluid

Figure 11A:
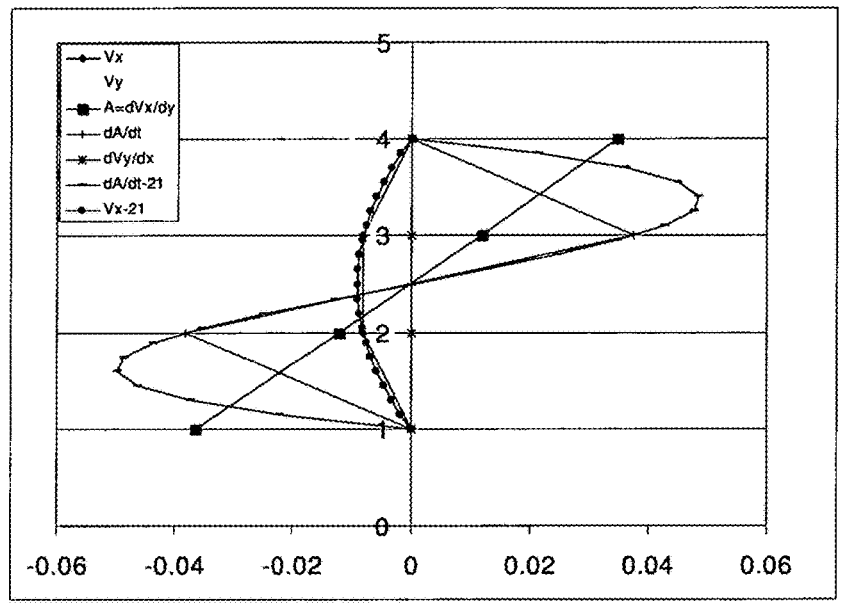
FIG. 11 illustrates fluid properties during deformation (11A) and step stresses by rate of one step per one Sec. (11B)

Regarding to what was mentioned for solid in the previous section; the same procedure is used for fluid with the difference that in fluid, velocity, which is a field vector, is the independent variable. Therefore, rate of deformation is used with respect to time as:

$$v_{xi} = \frac{x_{xi} - x_{xi}^0}{t}, v_{yi} = \frac{y_{xi} - y_{xi}^0}{t} \quad (96)$$

where t is time period of every step. In the same manner, velocity gradient is calculated which is the key equation to calculate viscosity stress and dissipation function. FIG. 11A shows the properties of fluid field at the nodes 1, 5, 7 and 9 of the element which are shown in the figure as the number 1, 2, 3 and 4. The figure presents the quadratic velocity profile at the left side of the elastic membrane. $v_x$, $v_y$ are fluid velocity in x and y direction, A and $$\frac{dA}{dt}$$

are gradient of $v_x$ with respect to y and its derivative with respect to time, and $$\frac{dv_y}{dx}$$

is gradient of $v_y$ in x direction. The curves of $v_x$ and dA/dt are plotted with two precisions: $v_x$ and $$\frac{dA}{dt}$$

(which is $$\frac{d}{dt}\frac{dv_x}{dy})$$

are drawn using data of the points at the nodes and, $v_{x21}$ and $$\left(\frac{dA}{dt}\right)_{21}$$

curves are plotted using 21 point on the left side of the membrane.

Solution Strategy

The solution strategy is simple because finite element method in this study is not a solution of the problem but it is a tool to apply the solution for the problem when numerical method is required. The solution strategy of finite element analysis is the same strategy of the analytical solution. The analytical solution was presented for one dimensional problem, however this solution is not applicable for two-dimensional problem. This is because the integration of the functions on the area of the element required a numerical method. Therefore, FEM is used to take advantage of element discritization and numerical solution. The procedure of solving the problem by FEM is as follows:

Measuring the deformation or displacement of the element/object.

Measuring the compressive force.

Setting the time step.

Calculation of strain and strain rate for the first step with respect to time.

Calculation of first step transverse deformation of fluid.

Calculation of $$\frac{dv_x}{dy}$$

and $$\frac{d}{dt}\frac{dv_x}{dy}$$

for the element during time step.

Solving two equations (23) and (38) for E modulus.

Calculation of elastic energy stored in the element during the step.

Calculation of viscous dissipation energy by subtracting the elastic energy from total work given to the element during the step time by equation (42).

Calculation of viscosity coefficient by equation (44).

Measuring the deformation and force of the next step.

Repeating the procedure from step 4-10 for the next time step.

Results

The finite element geometry is the same as the one shown in FIG. 10A. In addition, it was required to know what type of hyperelastic material and viscous media should be used to build a viscoelastic mechanism. In this regard, the model for which the details are shown in FIG. 5B and FIG. 10A is used. A maximum ramp load of maximum 1 N, which is a reasonable range force on a biological tissue, was applied. Since it was required to simulate the material behavior, it was assumed that the force is deforming the model under constant velocity. This means the displacement is assumed to be a ramp function. It is important again to note that the geometry of the model and viscoelastic mechanism is conformed to the experimental test machine (see next section). The maximum possible displacement of test machine is 13 mm. Therefore, the maximum compressive deformation obtained was 12.5 mm that means the compression of 25%. In such a way, it was possible to adjust the energy absorbed by viscous media to estimate its viscosity. Since, nonlinear iteration loop was chosen 25 steps, consequently, total time would be equal to the time step of deformation multiplied by 25.

Using the abovementioned data, the FEM was conducted in several time steps.

Figure 11B:
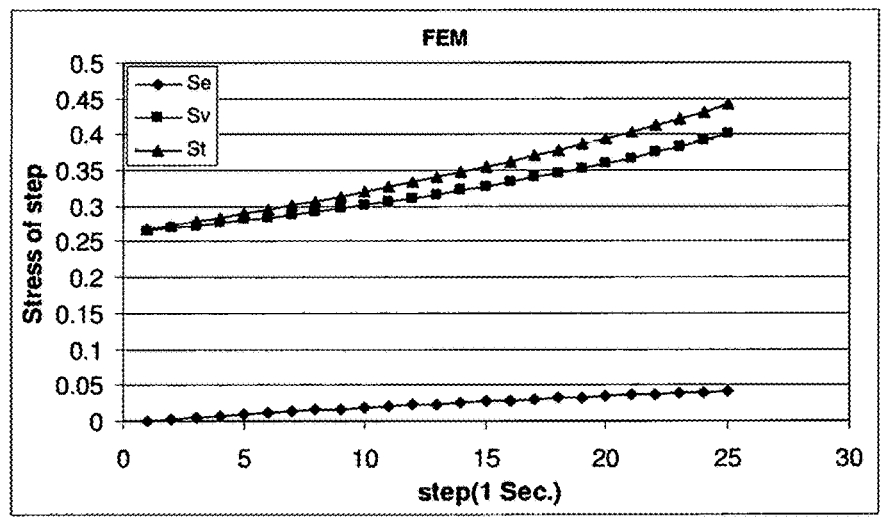
Figure 12A:
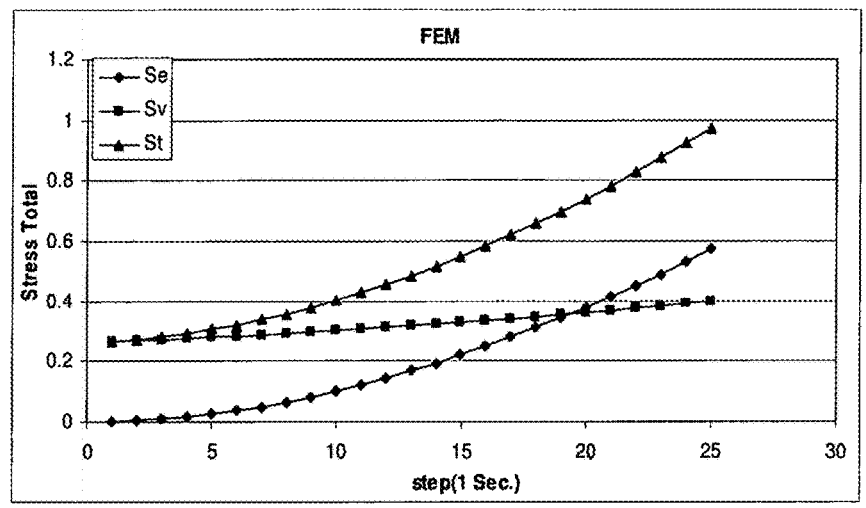
FIG. 12 illustrates total stresses by rate of one step per one Sec. (12A) and material properties by rate of one step per one Sec. (12B)

FIG. 11B shows the stresses: stress totals, elastic stress $s_e$ and viscous stress $s_v$ of every step with displacement speed 0.5 mm/Sec.; evidently the total stress is the sum of elastic and viscous stresses. In FIG. 12A, the stresses are shown with respect to initial configuration. This indicates the increase elastic stress and almost constant viscous stress.

Figure 12B:
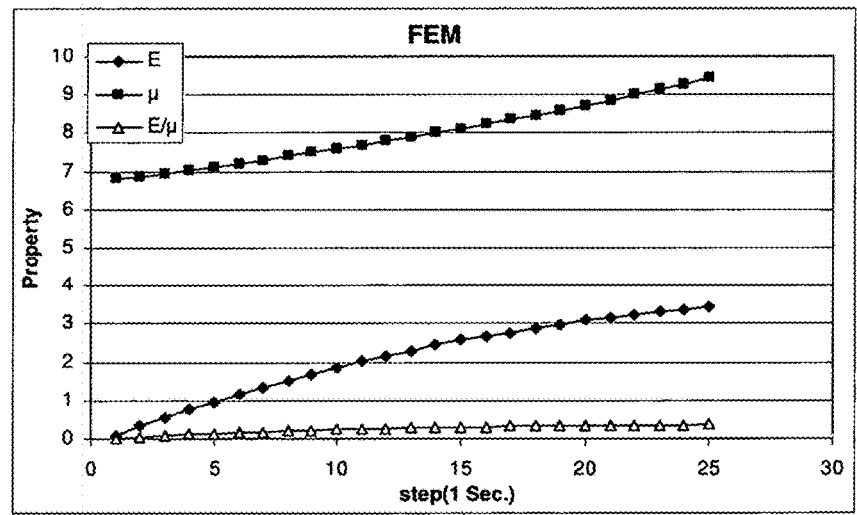

In FIG. 12B, the properties of material are shown with respect to the last updated configuration.

Figure 13A:
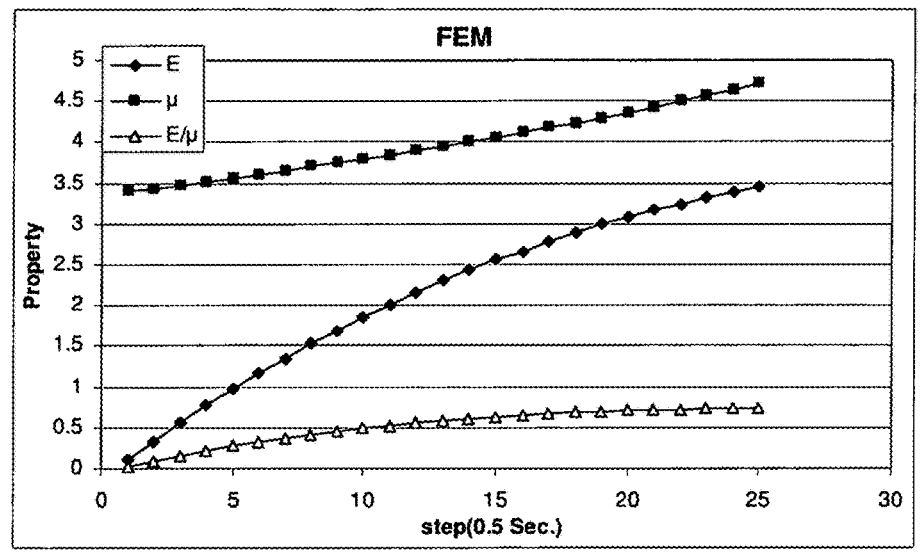
FIG. 13 illustrates material properties by rate of one step per 0.5 Sec. (13A) and material properties in different deformation speed (13B)

The properties of the same model by considering time step of 0.5 second are shown in FIG. 13A.

By comparing FIG. 12B and FIG. 13A, it can be concluded that the result of faster deformation is the consequence of low viscosity. Note that the elastic modulus remains unchanged during the deformation.

Figure 13B:
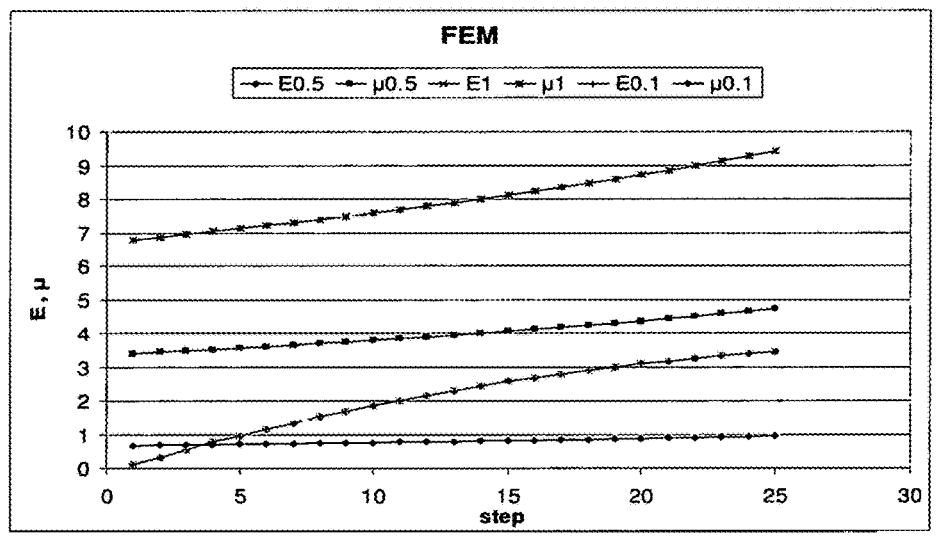

FIG. 13B shows the properties of the model with time step of 0.1, 0.5 and 1 second when the deformation rate remains constant. It demonstrates that faster deformation is due to low viscosity of the fluid.

Figure 14:
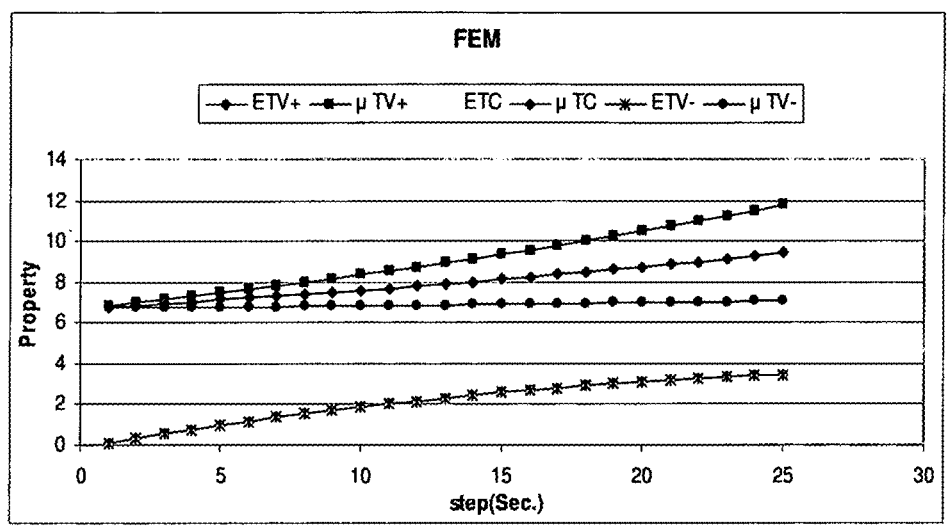
FIG. 14 illustrates material properties at one step per 1 Sec while decreasing and increasing

In FIG. 14, the properties of the model under three different velocity of deformation are presented: ETC and μTC are the properties of time step 1 second which remains constant during the deformation; ETV+ and μTV+ are the properties of time step 1 second which decreases during the deformation and finally ETV—and μTV—are the properties of time step 1 second which increases during the deformation. Therefore, the present approach not only can be used for constant deformation speed but also it can be used for varying deformation speed.

SUMMARY

In the present section, the modeling, strategy of FE solution and the result of FEA of viscoelastic material were explained in detail. In addition, variation of the viscoelastic material behavior with respect to time was presented and the results were discussed in detail. It was shown that the results justified the consistency of the proposed viscoelastic model and analyses.

Experimental Set-Up and Tests

The objective of the experimental is to validate the proposed model of viscoelastic material which is a combination of a hyperelastic material and a viscous media. In the present chapter, the design, fabrication and testing of viscoelastic mechanism are presented. In addition, the test machine and experimental set-up are explained and the results are discussed. Finally, the validation, repeatability and errors of the experimental work are will explained.

Design and Fabrication of Viscoelastic Mechanism

The viscoelastic mechanism of the experiment is designed based on the concepts of analytical approach which was discussed in analytical sections. To this end, the viscoelastic material is combined with a hyperelastic material, for which a compressive spring was chosen, and a viscous media from synthetic materials with base of polydimethylsiloxane. The mechanism is designed by taking into account the test machine (ElectroForce®3200 of BOSE®), available in our laboratory, which applies the force only in vertical direction. To prevent the force axis from deviating during the deformation, a guide mechanism was designed. The guides allow the machine to compress the mechanism while maintaining the alignment. In this regard, four male-female guides were used to ensure that the upper plate to move vertically according the lower plate. A compressive spring was placed in the center point of the plates and was centered by two small guides fixed on the two plates for preventing any possible buckling during deformation. An elastic balloon was used as the membrane of the viscoelastic material.

Figure 15A:
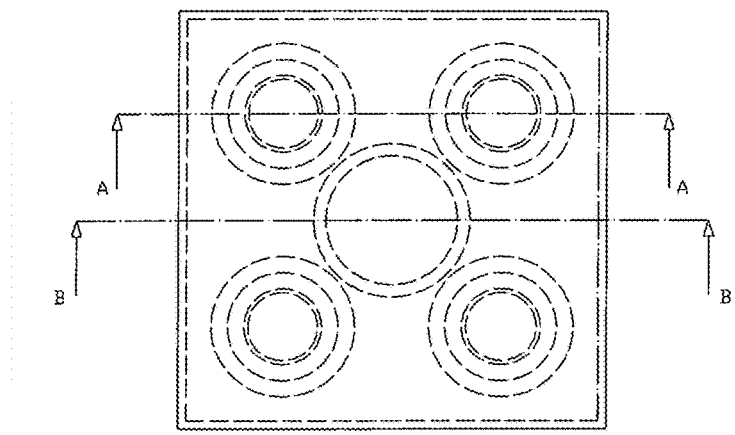
FIG. 15 illustrates the top view (15A) and two sections of viscoelastic mechanism (15B and 15C).
Figure 15B:
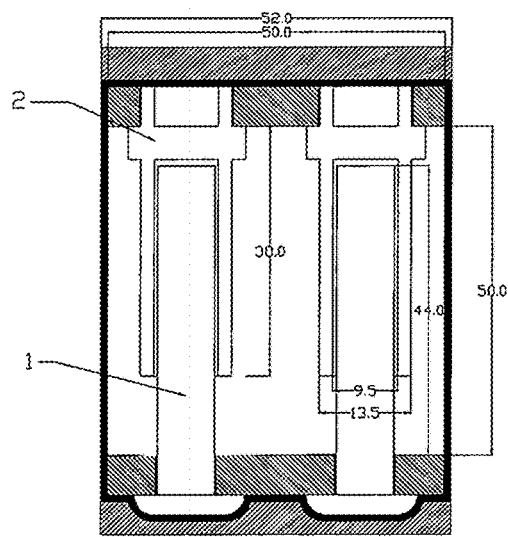
Figure 15C:
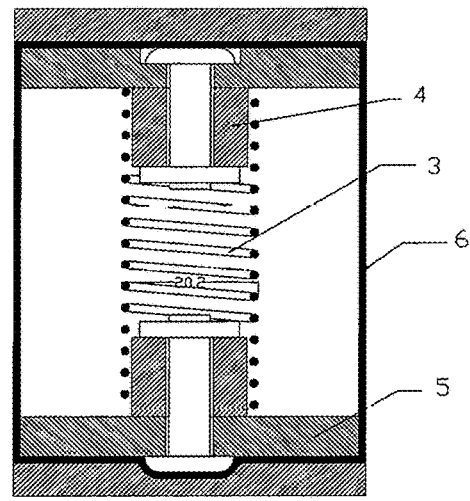
Figure 16A:
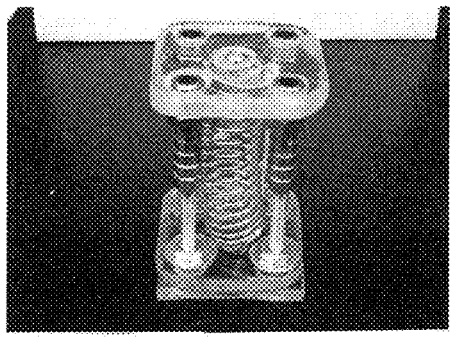
FIG. 16 illustrates viscoelastic mechanism without viscous media (16A, 16B and 16C) and mechanism assembly on the test machine (16D) and viscoelastic mechanism with viscous media before deformation (16E) and after deformation (16F)
Figure 16B:
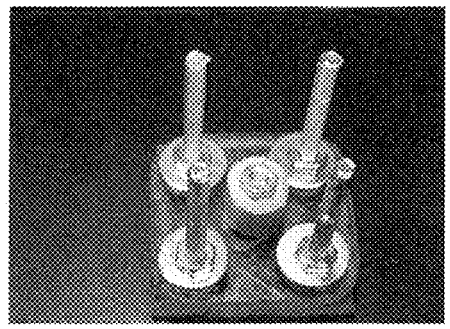
Figure 16C:
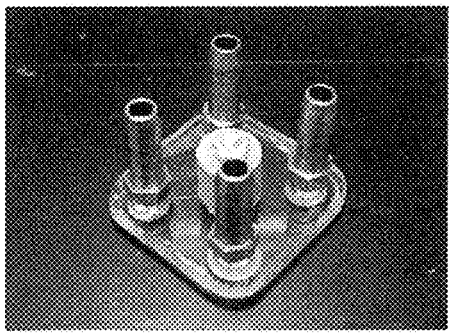
Figure 16D:
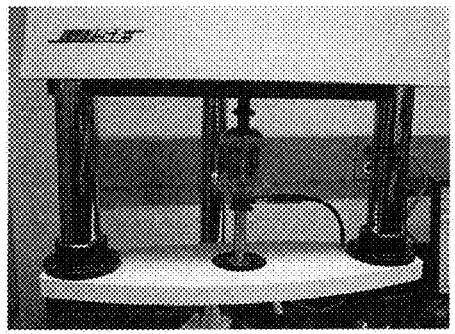
Figure 16E:
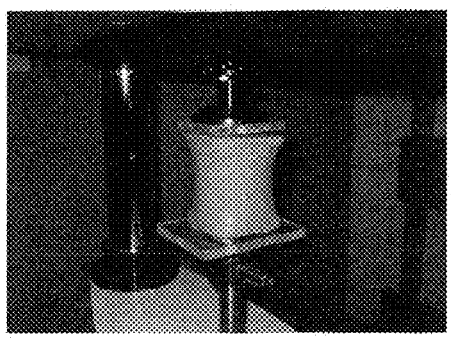
Figure 16F:
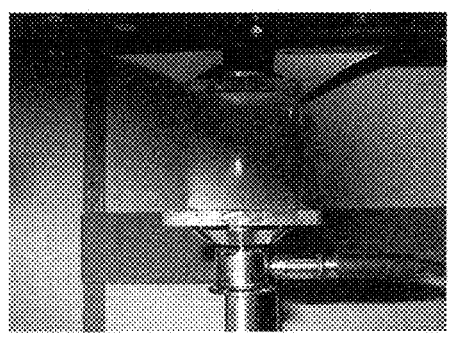

The females guides were made from bronze and the male from steel which was covered by an appropriate layer of Teflon to minimize the friction. The two plates were drilled together to guarantee the centerline alignment. The female guides had a through hole, so the male could pass through the female and the upper plate. The plates were made of Plexiglas with the thickness of 6 mm. The thickness of the upper plate was sufficient to be threaded to the female guides of which the outer side had the same threads. In order to prevent the membrane to expand in two directions, a fixture consisting of two Plexiglas plate were bolted together. The fixture makes two solid walls which allow the membrane expand only in one direction. The complete design and fabrication of the mechanism are done by the author. The mechanism drawings are presented in FIG. 15A, FIG. 15B, FIG. 15C. All dimensions are in millimeter with the tolerance of ±0.5 (if applicable). The detailed photographs of the mechanism are presented in FIG. 16A, FIG. 16B, FIG. 16C, FIG. 16D, FIG. 16E and FIG. 16F.

Finally, the mechanism is sealed in an elastic balloon which is filled with polydimethylsiloxane. The specifications of the five different range of polydimethylsiloxane used; which are DMS-T31, DMS-T35, DMS-T41, DMS-T41-2, DMS-T43, are as follow:

| Item: | Dynamic Viscosity (cP) | Kienamtic Viscosity (cStock) |
|---|---|---|
| DMS-T31 | 971 | 1000 |
| DMS-T35 | 4865 | 5000 |
| DMS-T41 | 9740 | 10000 |
| DMS-T41-2 | 12175 | 12500 |
| DMS-T43 | 29280 | 30000 |

More detailed specifications are presented in manufacturer data sheets.

Test Machine and Set-Up

The machine used for the experimental is Electro-Force®3200 of BOSE® which is placed in tactile sensing and robotics surgery laboratory.

Figure 17:
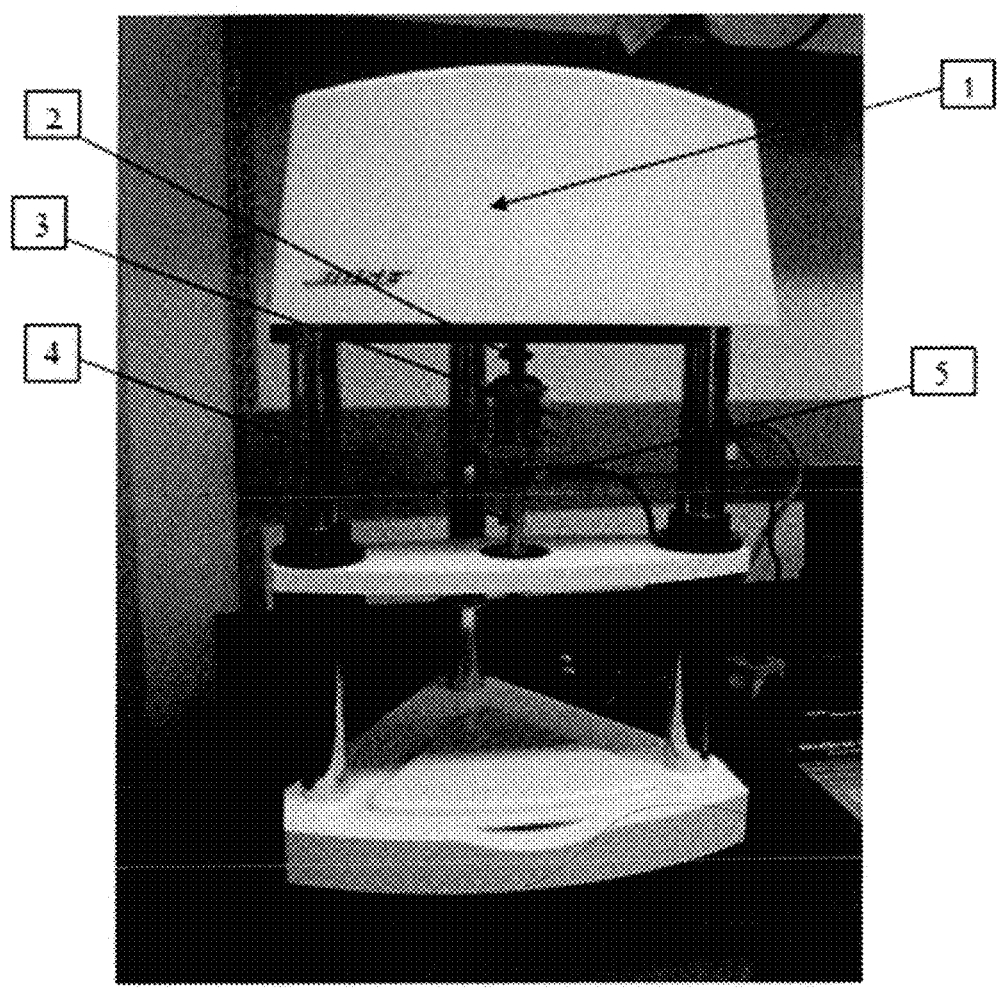
FIG. 17 illustrates Electroforce 3200 Bose

The machine is designed for testing materials including biological tissues. For this purpose, it is equipped, as an accessory, with hot/cold chamber to maintain the temperature and a saline bath to keep the biological materials in natural condition. The photograph of the machine is shown in FIG. 17.

The most important features of the machine are as follows:

Peak force capacity: ±225 N (50 lb)
Static (or RMS Continuous) force: ±160 N (35 lb)
Range of displacement: 12.5 mm (0.5 in)
Maximum frequency: 200 Hz
Vertical test space: 0-450 mm (0-18 in)
Load cell space to back column: 305 mm (12 in)

The machine motor is a linear electromagnetic one equipped with linear encoder of which the shaft is attached to the upper lever. On the lower shaft, a load cell is installed with gain factor of 1.06 which depends on the 2.5 mV/V sensor sensitivity and, 10V excitation voltage.

Figure 18:
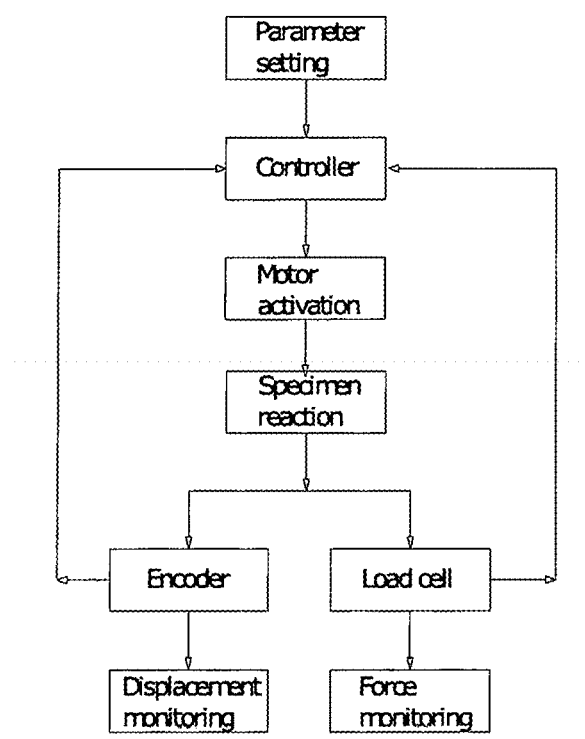
FIG. 18 illustrates schematic of Electroforce 3200 Bose®

The schematic of Electroforce 3200 Bose® is presented in the FIG. 18. The controller parameters are set by the user and then the motor activation occurs due to these parameters. When the motor shaft compresses the specimen, the reaction of the specimen slows down the shaft movement. The feedback from load cell and encoder are used by the controller to regulate the motor shaft movement for complying with the these parameters.

Tests on the Spring and Guides Friction of the Viscoelastic Mechanism

Figure 19A:
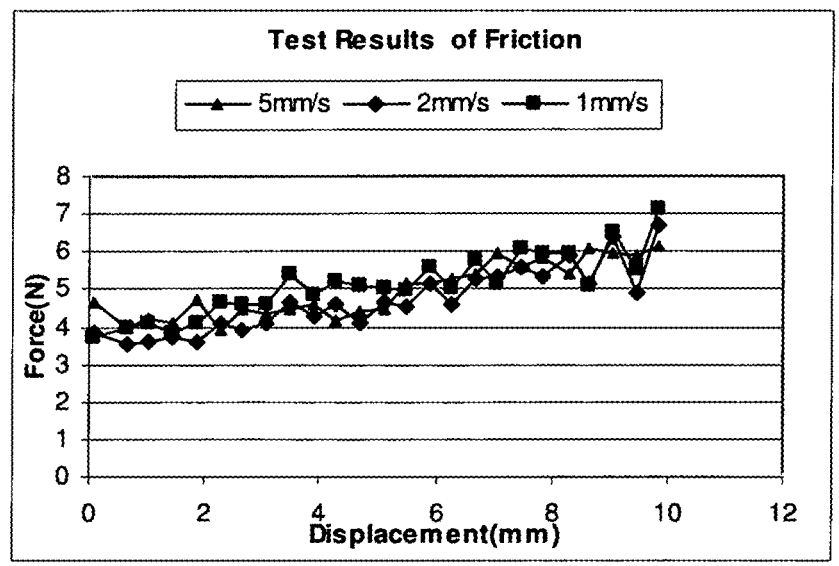
FIG. 19 illustrates test result of friction (19A) and test result of spring (19B)

The tests procedure is as follows:

The viscoelastic mechanism is assembled without spring and elastic membrane for measuring the friction of the guides. The results are presented in FIG. 19A which shows the force and displacement with three ranges of speed: 1 mm/s, 2 mm/s and 5 mm/s.

Figure 19B:
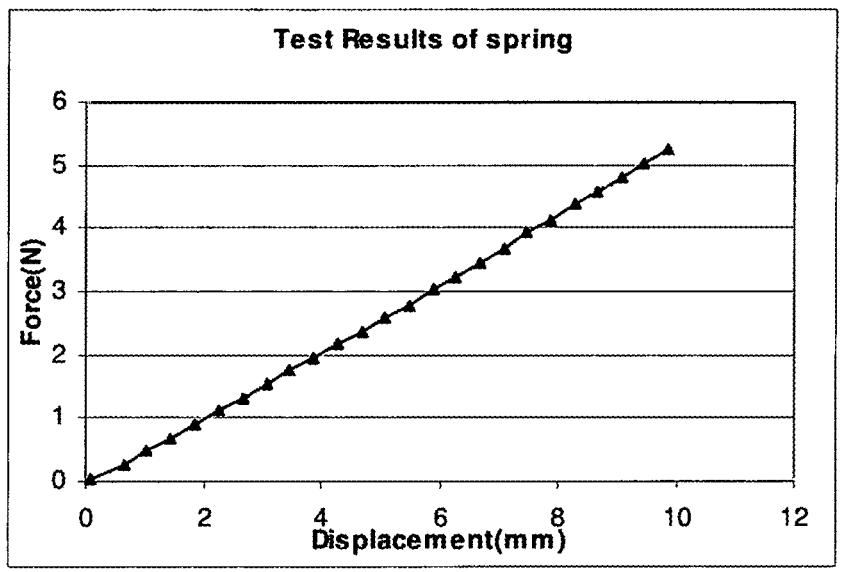

Following the above, the spring is tested without the guides. Therefore, the force and displacement are related to the spring alone. The results are shown in FIG. 19B. It is shown that the spring has a linear behavior with stiffness of 0.52 kN/m.

The guides, the elastic membrane and spring are then assembled.

The viscoelastic mechanism is filled with polydimethylsiloxane, and for every speed of deformation, the test is repeated three times. The same liquid with higher viscosity is replaced and tested again. The kinematic viscosities of the liquids are in ascending manner: 1000, 5000, 10000, 12500 and 30000 cStock.

Test Procedures and Results

Figure 20A:
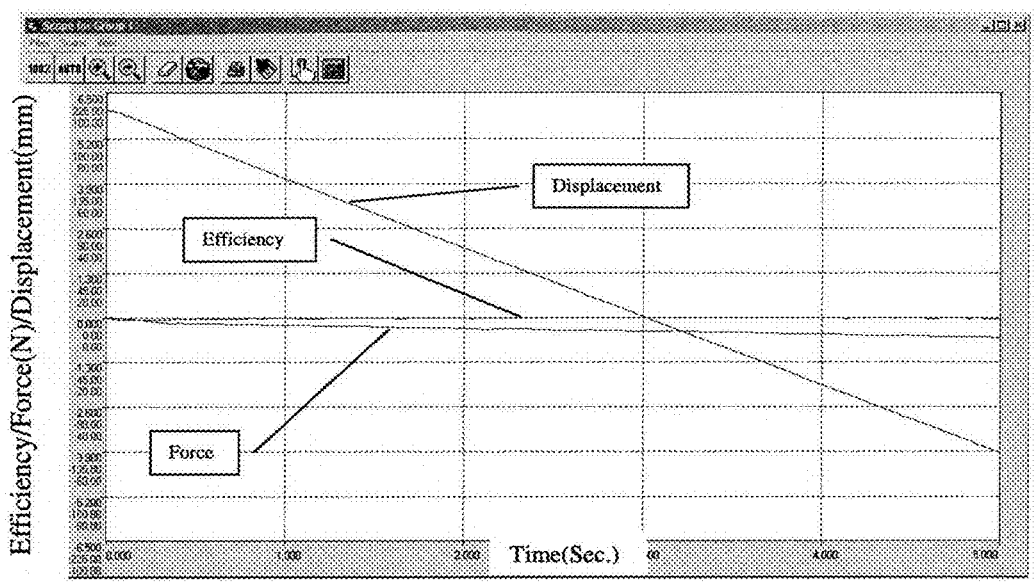
FIG. 20 illustrates test curves for DMS-T31 with deformation speed: 2 mm/Sec (20A) and force-displacement curves for DMS-T31 (20B)

The test began with Polydimethylsiloxane DMS-T31. The motor speed was set at 0.1 mm/Sec. and maximum displacement rate to 10 mm. The data of load and displacement with respect to time were obtained. Afterward, the experiment with speed of 0.2, 0.4, 1, 2 and 5 mm/Sec. were achieved. The FIG. 20A shows the experiment with speed of 2 mm/Sec. The vertical axis corresponds to axial efficiency, force and displacement, respectively, in ascending order, and horizontal axis correspond to time.

Figure 20B:
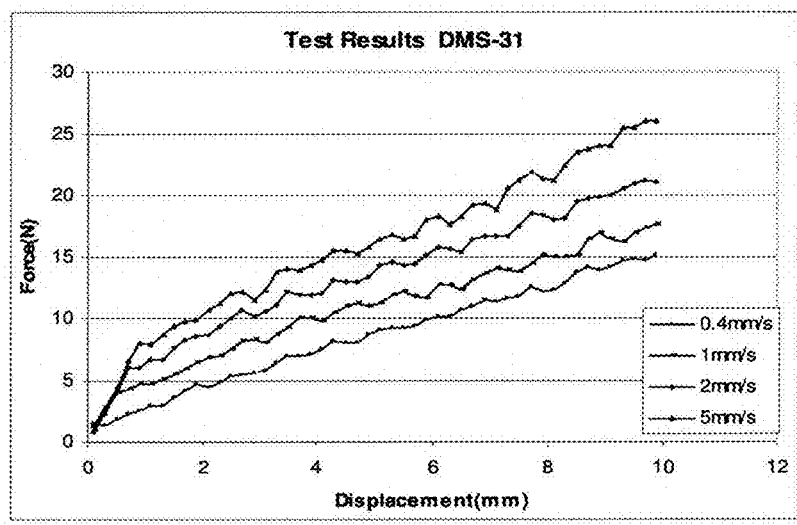

The tests with higher speeds were performed and the results are presented in FIG. 20B. As it is shown, the loads increase with respect to speeds of deformation. The oscillating of loads is due to several factors including test machine performance, wave shock of the fluid and membrane oscillation.

Figure 21A:
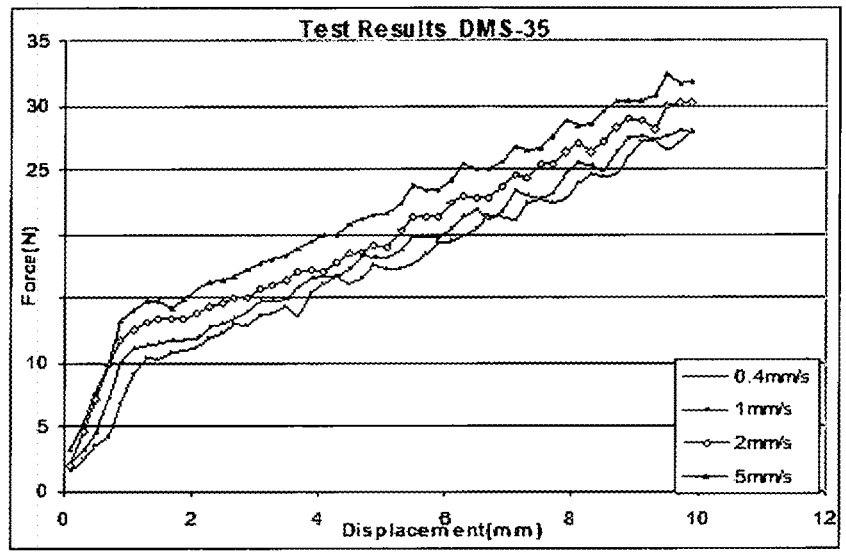
FIG. 21 illustrates force-displacement curves for DMS-T35 (21A) and force-displacement curves for DMS-T41 (21B)

The tests with DMS-T35 were performed and the results are presented in FIG. 21A. As it is shown, the loads are increasing with respect to the speeds of deformation. The same behavior of oscillation is again observed.

Figure 21B:
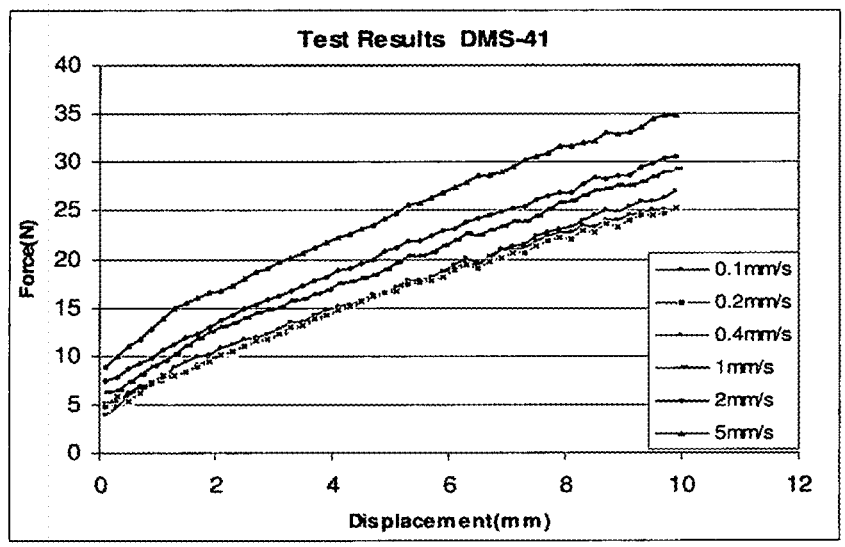

The tests with DMS-T41 were achieved and the results are presented in FIG. 21B. As it is shown, the loads are increasing with respect to the speeds of deformation which is the behavior of viscoelastic materials. It can be observed that the oscillation behavior is considerably decreased. This means that higher viscosity decreases the oscillation behavior.

Figure 22A:
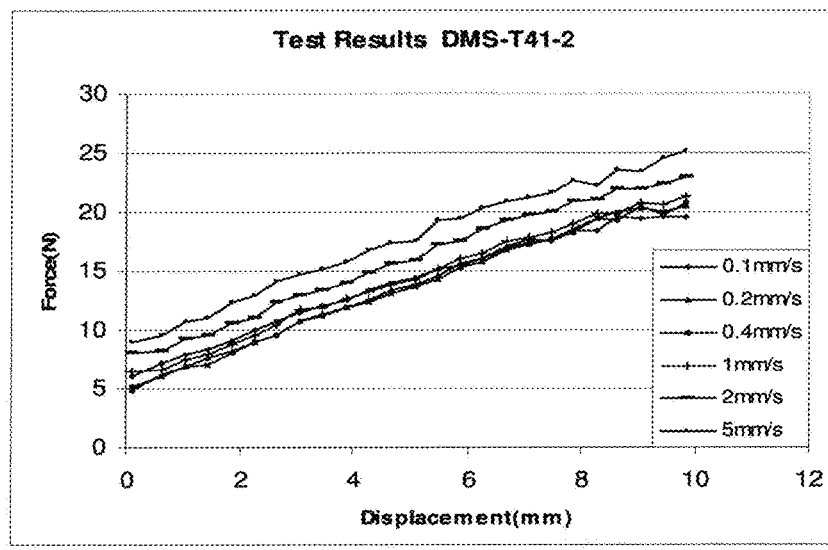
FIG. 22 illustrates force-displacement curves for DMS-T41-2 (22A) and test curves including relaxation for DMS-T41-2 with speed of 5 mm/Sec. (22B)

The tests with DMS-T41-2 were performed and the results are presented in FIG. 22A. As it is shown, the loads are increasing with respect to the speeds of deformation. Note that the oscillation behavior is considerably decreased. It also shows that with lower the speed of deformation, the gap between the forces become close.

Figure 22B:
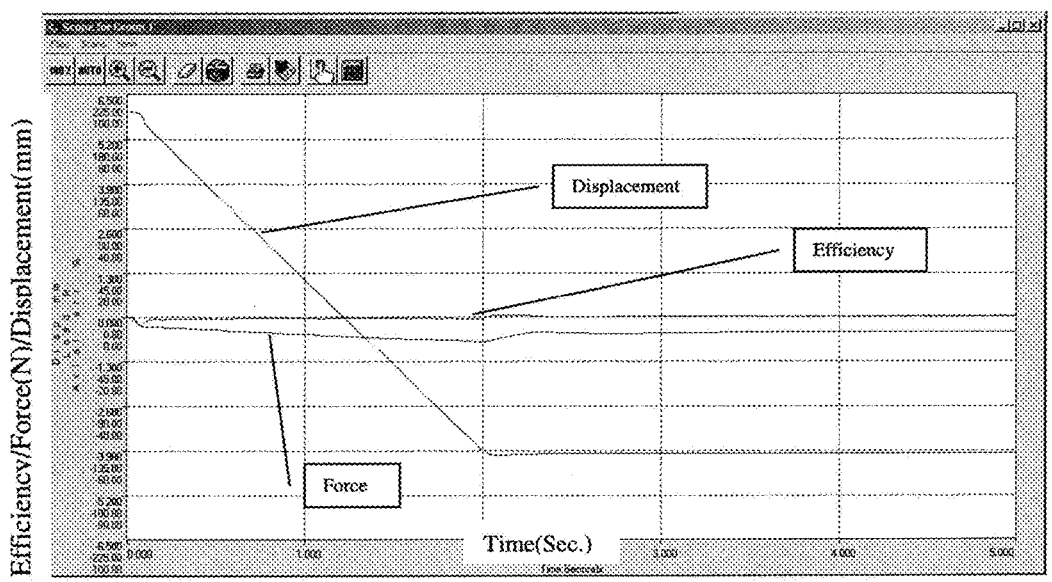

Since the behavior of the last test was smoother than the others, the relaxation test was achieved with speed of 5 mm/Sec. that is shown in FIG. 22B. It can also be observed that the efficiency of the machine during the 0.1 second of the start point was deteriorated from the set point. This happens when the delay of respond of the control system is greater than the response of the material. In another word, the system has a certain delay to adjust the load for maintaining the preset velocity of deformation.

Figure 23A:
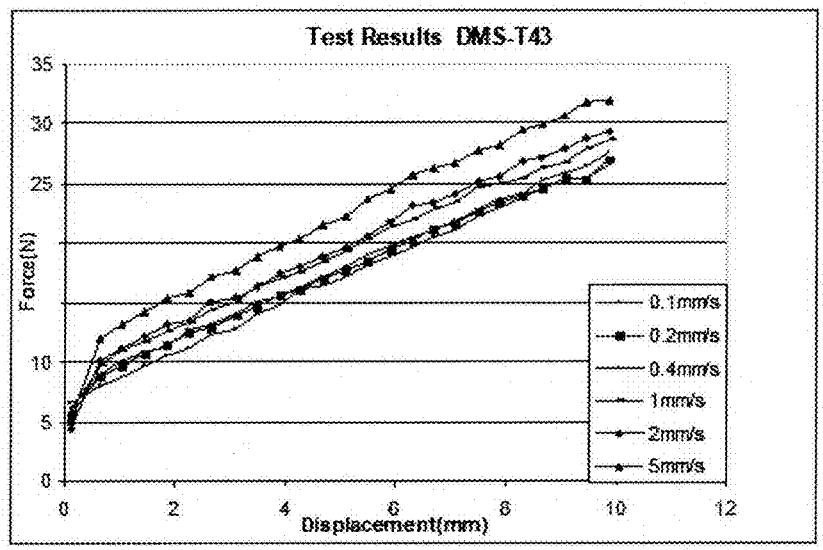
FIG. 23 illustrates force-displacement curves for DMS-T43 (23A) and test curves for DMS-T43 with deformation speed: 5 mm/Sec. (23B)

The tests with DMS-T43 were achieved and the results are presented in FIG. 23A. As it is shown, the loads are increasing with respect to the speeds of deformation. It can be observed that the oscillation behavior is considerably decreased. It also shows that even with low speed the differences between the forces are so apparent.

Figure 23B:
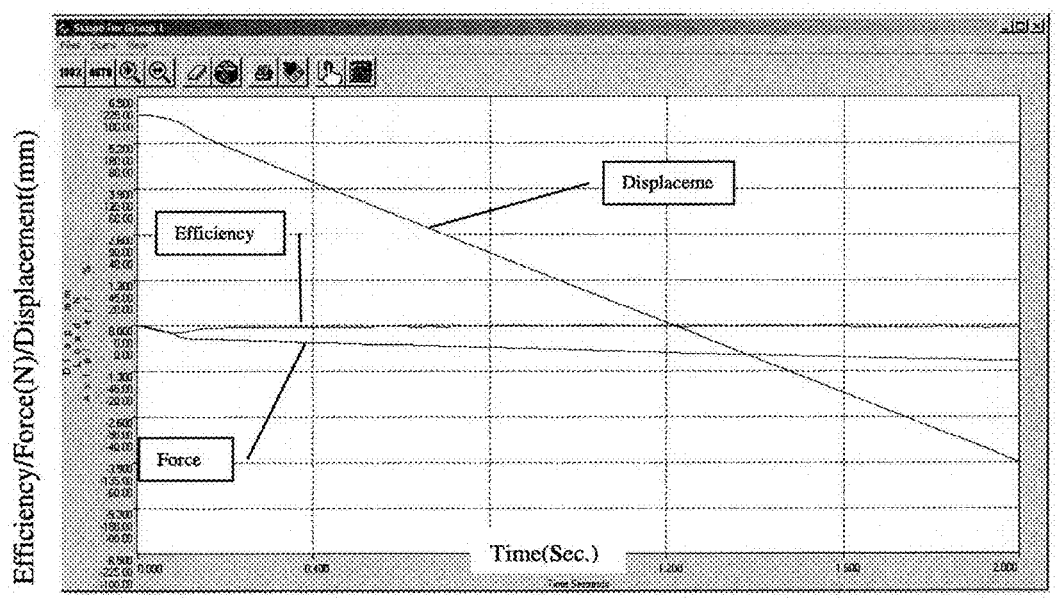

The test results with speed of 5 mm/Sec. are shown in FIG. 23B. Again it can be seen that the efficiency in the 0.3 second of the test time is considerably deteriorated.

Repeatability, Errors and Validation

The experiments were implemented with five different ranges of viscous media, and for each fluid, several speeds of deformation were used. In addition, as it was mentioned in the previous section, the test for every fluid with every speed of deformation was repeated three times. Since the mechanism is fixed between the shafts of the test machine. The set-up is secured against any changes that could affect the tests. The only factor which may cause a problem for repeatability of the tests is the quality of the balloon. The fluid may leak from the balloon under high speed of deformation. Therefore, the experimental are completely repeatable as far as the set-up is not changed during the tests. The repeatability of the experiments was justified by the data of more than ninety tests which were performed with different fluids and different speeds of deformation. All the tests showed the consistency of the experimental results with real behavior of viscoelastic materials.

The errors of the experimental are usually determined by the comparison of the results with the available data of similar cases. Another way to determine the errors of experimental is the comparison of the results with analytical results. In the case of the presented tests, none of the abovementioned methods is achievable. The reason is the uniqueness of the present approach and related experiments. On the other hand, the results of the experiments, which justified the validation of the proposed model for viscoelastic materials, can be compared with the behavior of viscoelastic materials. Since any viscoelastic material shows the time dependency behavior according to its properties, the comparison of two different materials can be different with respect to different speeds of the deformation. Therefore, the behavior of two materials cannot be compared quantitatively, but their behaviors can be compared qualitatively. In another word, it can be concluded which material is more viscoelastic or which is more hyperelasric. Furthermore, the behaviors of viscoelastic materials are nonlinear that means even if two materials are equally visoelastic or hyperelastic, the curves of their behaviors do not fit in all ranges.

According to what was mentioned, the errors, or more precisely, the differences between analytical and experimental results, are investigated to determine the main factors which affect the behavior of the mechanism.

Membrane of the viscoelastic mechanism is one of the factors which cause different behaviors of the mechanism. By comparing the curves of speed 5 mm/Sec. in FIG. 21B and FIG. 22A, it can be seen that the highest force for DMS-T41 is 35 N while for DMS-T41-2 is 25 N. It can be concluded that the force of elastic membrane is the considerable portion of the stress generating in the set-up. It means that the harder membrane causes higher stress.

The test machine, on which the viscoelastic mechanism is tested, uses the proportional-integral-derivative (PID) control system for maintaining its functionality according to material behavior. It means that when the velocity of deformation is deteriorated from preset one, the controller uses one or combined method of feedback manipulation to compensate the deformation velocity. Consequently, there is a delay time of response, which is due to software and hardware performances, for regulating the motor torque and compensating the error of deformation velocity. The time of delay produces a considerable inefficiency in a short period of the test when displacement speed is not compatible with the preset parameters of the system. The tests with DMS-T31, DMS-T35, DMS-T43 shows that the system parameters are less or more than necessary to comply with the behavior of the material. On the other hand, the tests of DMS-T41 and DMS-T41-2 showed that these materials are within the range of the machine parameters.

In analytical, it was assumed that the fluid is incompressible while the viscous media is compressible about 9% with respect to the pressure according to manufacturer's data sheet. The compressibility of the fluid verses pressure requires precise data in order to be taken into consideration. Obtaining these data requires a very precise experiment which is out of the scope of the present study.

The guides, which are installed inside the membrane compartment, have a very small clearance (gap) between the male and female guide. This gap is filled when the membrane compartment is filled with viscous flow. Therefore, the mechanism forms four dashpots that each has 35 mm length. Consequently, the viscous stress in the mechanism consists of two velocity gradients of flow: 1) the flow in the traverse direction with respect to displacement and 2) the flow in the guides in the direction of the displacement. The latter flow produces viscous stress as well as the first flow. The error due to the effect of these dashpots for DMS-T41-2 was calculated to be about 3.5% of the force measured in the test.

Another difference of the viscoelastic mechanism with theoretical model is the flow of viscous media. In the experimental work, the viscous media flowed in 3D directions while in the analytical model the flow was assumed in 2D dimensions.

In brief, most of the abovementioned errors are not the errors of the experimental but the structural differences between the experimental viscoelastic mechanism and ideal model of analytical. In another word, they constitute the characteristics of the experimental model that does not affect the validity of the behavior of the viscoelastic mechanism.

The validation of the experimental can be verified by comparison of the behavior of the viscoelastic mechanism with the behavior of viscoelastic material reviewed in literature. The results of experimental presented in FIG. 20B, FIG. 21A, FIG. 21B, FIG. 22A and FIG. 23A confirms that all five viscoelastic mechanisms comply with time dependency of viscoelastic materials. In addition the result of relaxation test presented in FIG. 22B shows that the mechanism successfully complies with relaxation behavior of viscoelastic materials.

Summary

In this section, the design and fabrication of the viscoelastic mechanism was explained. In addition, the set-up including test machine was described. Furthermore, the results of the tests of the viscoelastic mechanism with different range of viscous media were presented. Finally, the repeatability, errors and validation of the experimental were verified.

Discussion and Conclusion

In the present section, the deficiencies and errors involved in the proposed approach is discussed. In addition, the differences of the models of experimental and FEA are compared. Finally conclusions, contributions, and future works are presented.

Discussion

Finite Element Method, as it implies to be a method to solve the problems, has some draw backs, which should be taken into account. In FEM the entire model is discritisized to elements and nodes. The discritization of the model overcomes the difficulties of solving the problems due to high order of strong form of constitutive equation. Furthermore, it provides the solution with robustness to deal with irregularity of geometry, complicated boundary conditions, nonlinearities, time dependency, etc. On the other hand, any FEM may introduce certain errors which are in some cases negligible. As an example; the FEM solution of one dimensional hyperelstic problem, which was explained in previous section and of which the results were illustrated in FIG. 4B, shows 1.5% error from analytical solution. In addition numerical integration introduces 0.57% in the unit area of the model. Therefore, by using FEM, if the errors are added up, there would be 2% error which is quite acceptable. By assuming that the same amount of error would be occurred in viscous fluid part, we should predict about 4% error due to FEM solution.

One of the errors involved in the experiment is due to compressibility of the fluid. The polydimethylsiloxane, according to the manufacturer's data sheet, is compressible about 9%. The assumption of incompressibility of the viscous media produces a certain error in the modeling. The compressibility of the fluid verses pressure requires precise data in order to be taken into consideration. In order to include effect of compressibility into the experimental analysis, further experiment required that is out of the scope of this study.

In the experimental work, a balloon was used as the membrane for the viscoelastic mechanism. Every assembly of viscoelastic mechanism was performed with one of the viscous fluid and one balloon. After completion of the tests with one assembled mechanism, it was disassembled. Therefore, the balloon became unsuitable to be reused. In another word, every mechanism had different viscous media and different membrane. Consequently the data of one mechanism could not be compared with others because the resistances of the membranes were different. On the other hand, analyzing the reaction force of the elastic membrane against flow of a viscous fluid requires an extensive study. Eventually, the effect of the elastic membrane could not be measured in the experimental. In another word, the resistive force of the membrane remained undetermined and was added to viscous stress that increases the error of the calculated viscosity coefficient considerably.

The test machine, Electroforce 3200 Bose®, uses the proportional-integral-derivative (PID) control system. The PID control system regulates the functionality of the machine according to material behavior. It means that the machine controls the applied force and the velocity of displacement with respect to preset parameter to overcome the resistance of the material. In this regard, the controller uses one or combined method of manipulating the feedback signal to control the deformation velocity. Consequently, a delay time of response, which is due to software and hardware performances, occurs to compensate the error of deformation velocity. This delay time of response produces considerable errors in data of the tests within few moments of the starting time. The duration that machine requires to regulate the deformation speed depends on the material and preset speed of displacement. Consequently, the data collected from the machine at the first steps of the tests are not reliable because the displacement speed was not synchronized with right displacement speed as it was preset.

Tests were assumed to be taken place in such a manner that the viscous fluid flows only in one direction, so the flow could be modeled as a 2D velocity gradient. For this purpose, a fixture was provided to be used for the experimental but regarding the friction between the moving elastic membrane and the fixture (see FIG. 16A, FIG. 16B and FIG. 16C), the data were not valid. Therefore, the tests were performed by free membranes. Consequently, the velocity gradient changed to 3D dimensional. Modeling three dimensional viscous flows in a closed elastic membrane is a certain challenge which was so far from the scope of this study. The consequent change of the model increases the error of the results of FEA and of experimental quantitatively.

In addition, the four male-female guides of the mechanism were filled with viscous media. The four assemblies of cylinder and piston with a small gap which is filled with viscous fluid constituted four dashpots. The four dashpots of 35 mm length produced resistance force. Consequently, the viscous stress in the mechanism consists of two flow velocity gradient: 1) the flow in traverse direction with respect to displacement and 2) the flow in the guides in direction of the displacement. The error due to these dashpots for DMS-T41-2 was calculated to be about 3.5% of force measured in the test.

Regarding the tests results presented in FIG. 19A, FIG. 19B, FIG. 20A, FIG. 20B and FIG. 21B, it can be concluded that the data of tests with DMS-T31 and DMS-T35 shows oscillation behavior. This could be due to the friction of the guides and set-up assembly or the shock wave of the moving fluid. Therefore, the data of DMS-T41, DMS-T41-2, DMS-T43 which have, dynamic viscosity of 9.75, 12.18 and 29.28 Pa·s respectively are used to analyze the behavior of the mechanism.

It can be seen that higher displacement speed produces higher force that complies with viscous stress concept. In fact, higher speed means higher velocity gradient and consequently higher viscosity stress.

By comparing the curves of speed 5 mm/Sec. in, FIG. 21B and FIG. 22A, it can be seen that the highest force for DMS-T41 is 35 N while for DMS-T41-2 is 25 N. It can be concluded, first, that the elastic membrane force is the considerable portion of the stress generating in the mechanism i.e. the harder membrane causes higher stress. Secondly, it can be concluded that when the elastic membrane is harder the oscillation behavior decreases considerably. Finally, it can be seen that, in the viscoelastic mechanism of DMS-T41 that the membrane is harder, the difference between speed curves are distinguishable from speed of 0.4 mm/Sec. and higher. Contrary to that, in the mechanism of DMS-T41-2 of which membrane is softer, the difference between speed curves are distinguishable from 1 mm/Sec. and higher. This fact emphasizes on the interaction between hyperelastic element and viscous media in the viscoelastic mechanism.

Figure 24A:
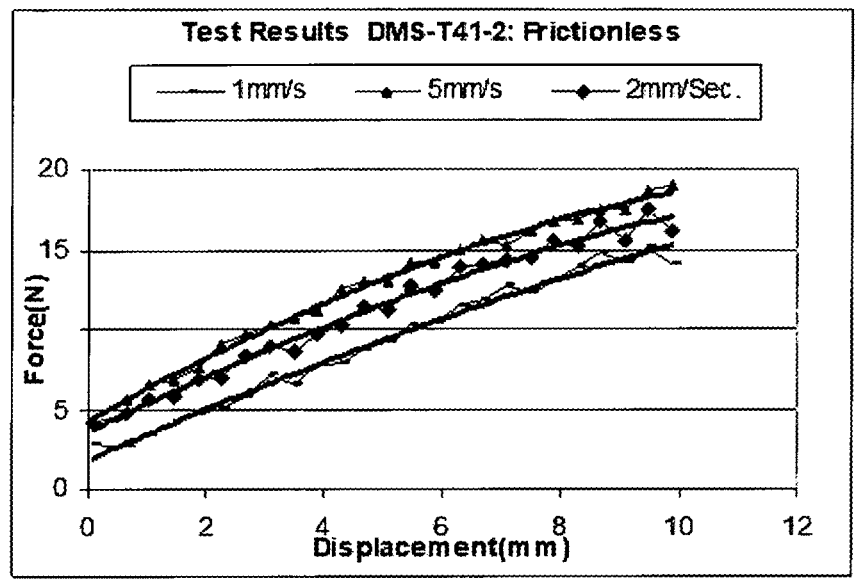
FIG. 24 illustrates test results of DMS-41-2 without friction load (24A) and test results of DMS-41-2 without friction and spring loads (24B)

Since the mechanism was changed by assembling new membrane and another viscous fluid, the results of the tests of different mechanism could not be compared. Therefore, one of the mechanisms, which was filled with the fluid with viscosity coefficient at the middle of the range, was analyzed numerically. For this purpose the result of DMS-T41-2 was selected and the friction loads were subtracted. The resulting curves are shown in FIG. 24A. In addition, only the test results of 1, 2 and 5 mm/Sec., which are identical from the others, were used for calculation. Furthermore, the trend curves are drawn to omit oscillation behavior.

Figure 24B:
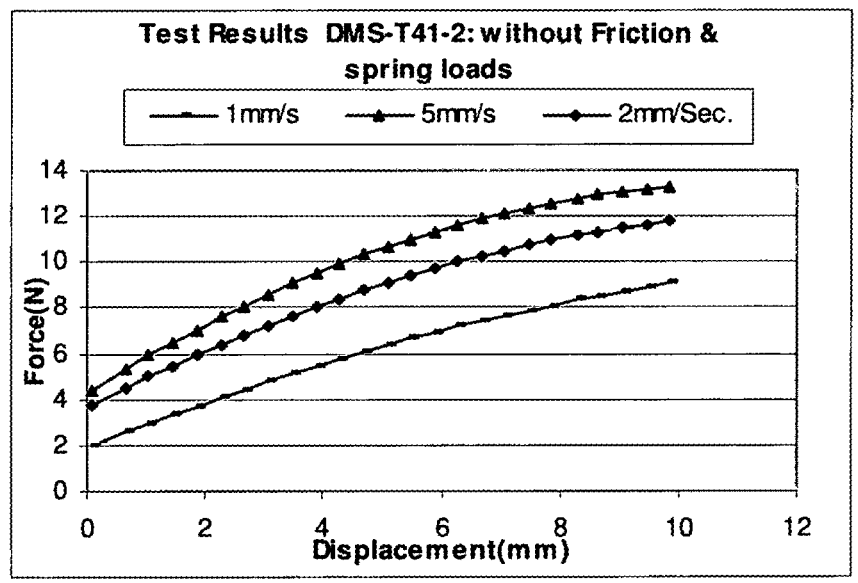

By subtracting the force of spring which was measured separately, it results in the curves which are shown in FIG. 24B.

Figure 25:
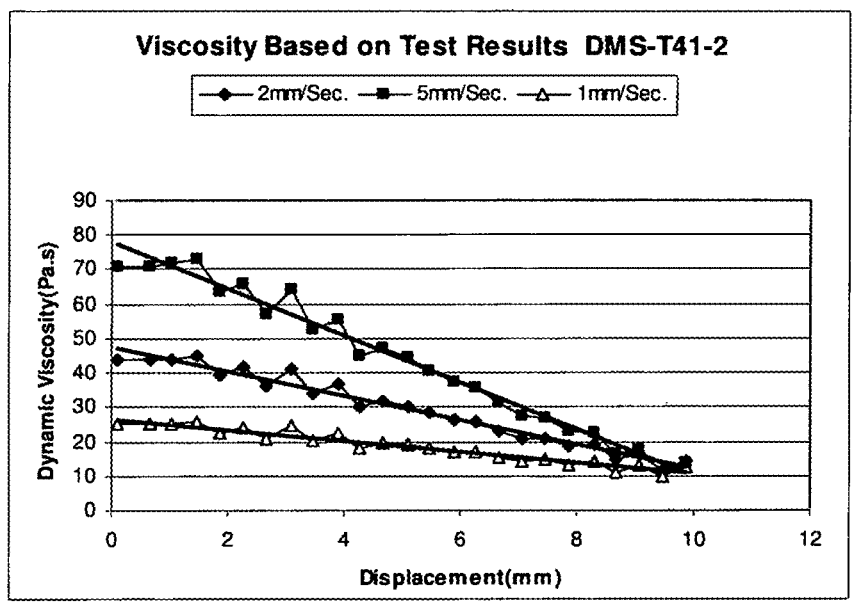
FIG. 25 illustrates dynamic viscosity coefficient based on test results of DMS-41-2
Figure 26A:
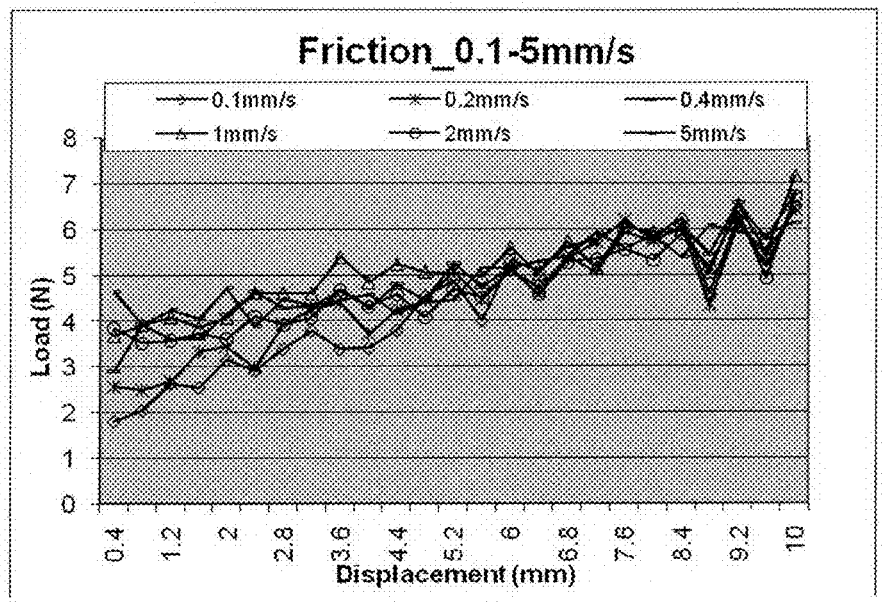
FIG. 26 illustrates the test results of friction of guides (26A) and spring of artificial object (26B).
Figure 26B:
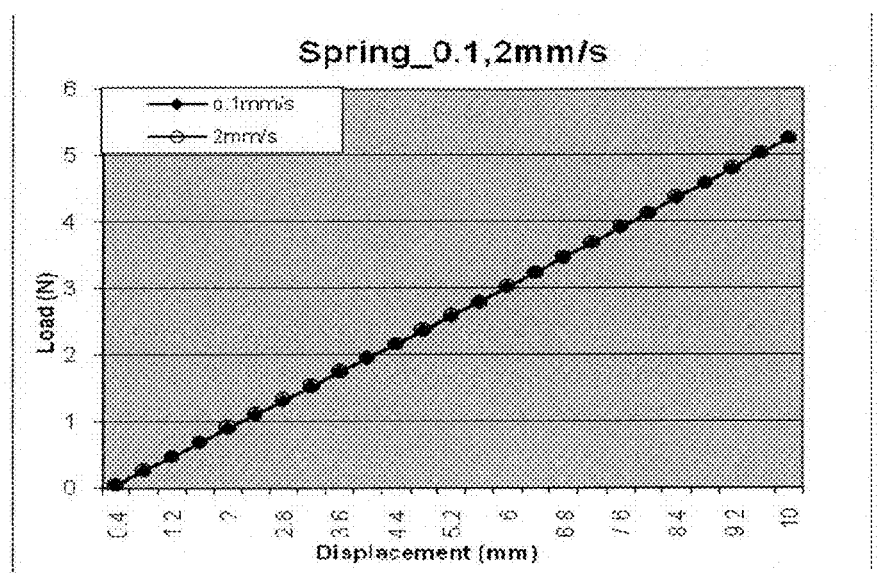
Figure 27A:
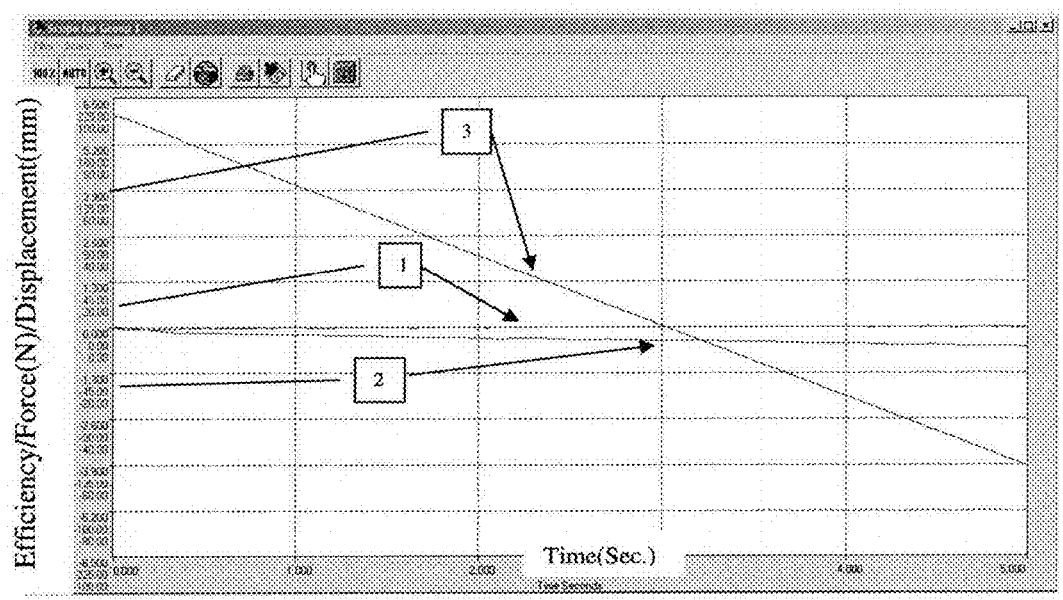
FIG. 27 illustrates the test curves of DMS-T31 with deformation speed: 2 mm/s (27A) and force-displacement curves of DMS-T31 with different deformation speeds (27B).
Figure 27B:
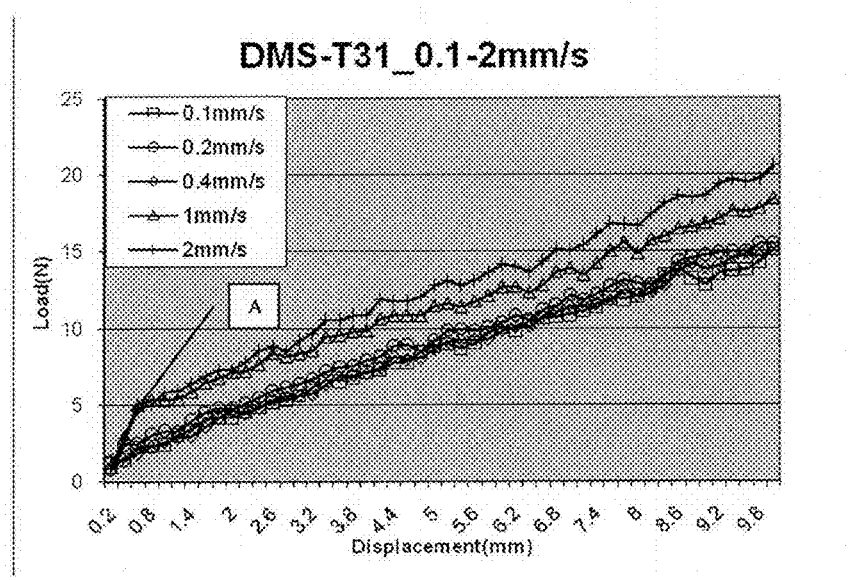
Figure 28A:
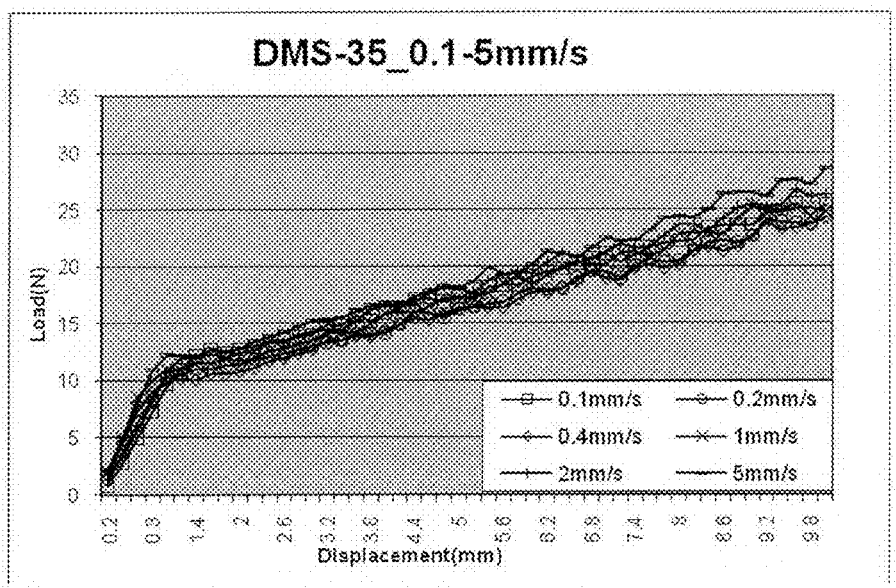
FIG. 28 illustrates the test force-displacement curves of DMS-T35 (28A) and force-displacement curves of DMS-T41 (28B).
Figure 28B:
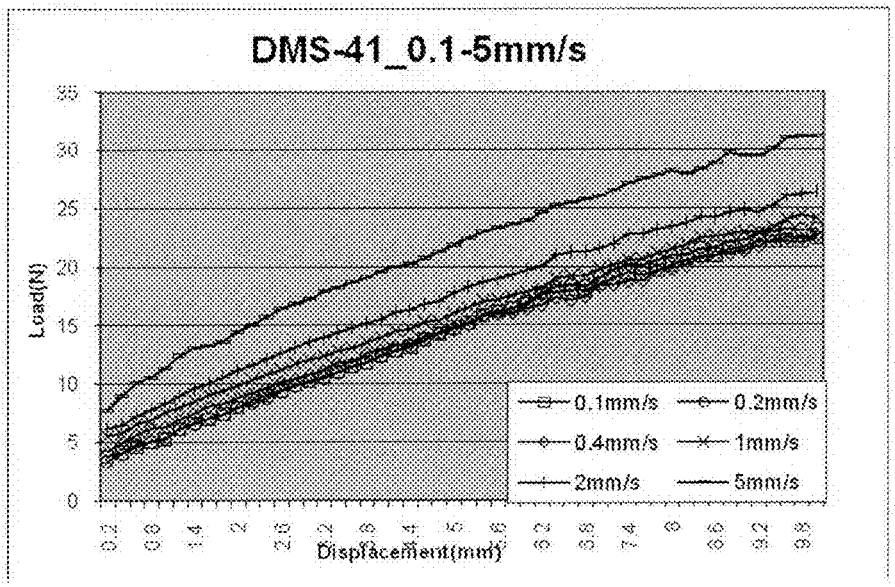
Figure 29A:
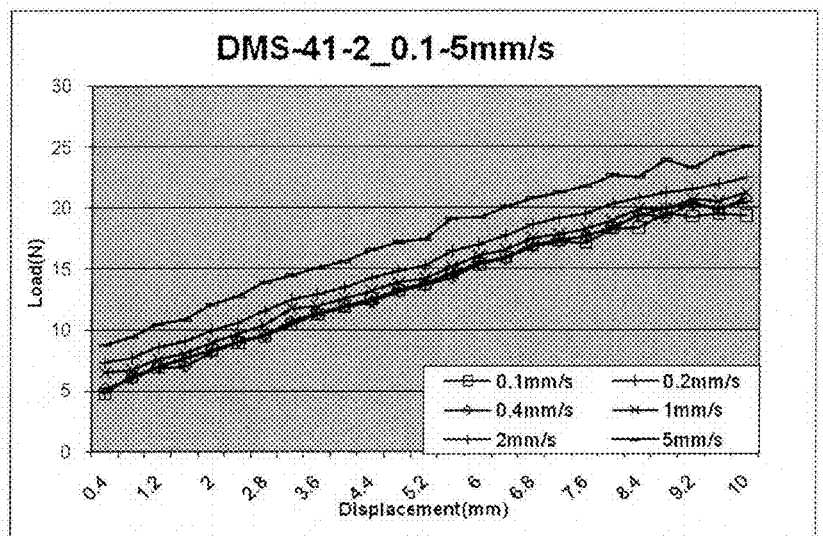
FIG. 29 illustrates the test force-displacement curves of DMS-T41-2 (29A) and test curves of DMS-T41-2 with speed of 5 mm/s including relaxation (29B).
Figure 29B:
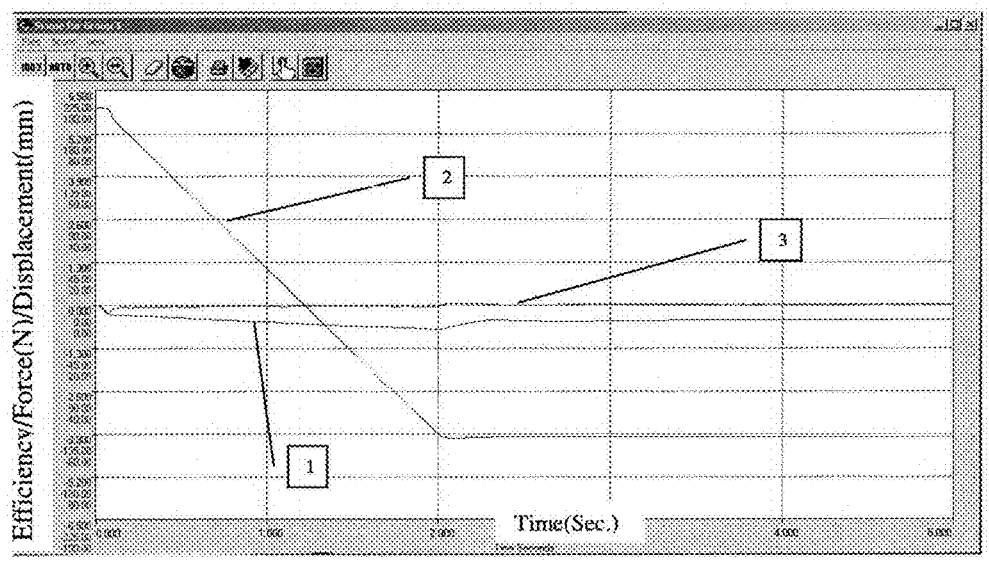
Figure 30A:
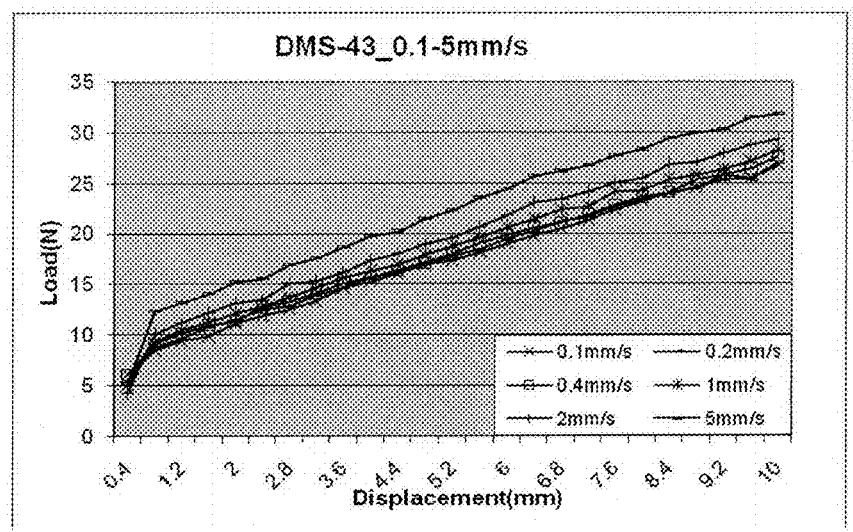
FIG. 30 illustrates the test force-displacement curves of DMS-T43 (30A) and test curves of DMS-T43 with deformation speed: 5 mm/s (30B).
Figure 30B:
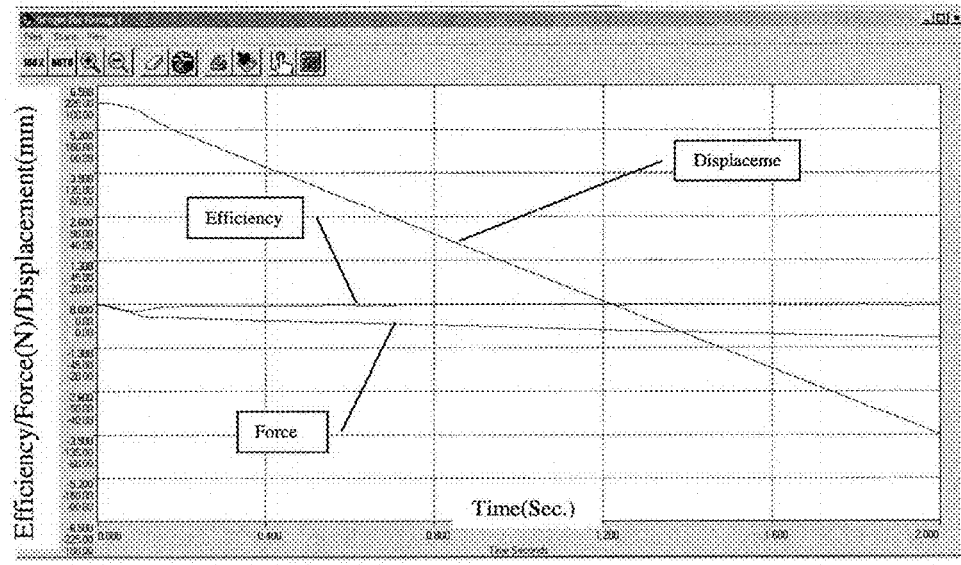

The resulting data were used to calculate the viscosity through nonlinear approach, though membrane force could not be excluded from it. The viscosity coefficients versus displacement curves for DMS-T41-2 are presented in FIG. 25.

It can be seen that the calculated viscosity coefficients differ completely from manufacturer's specification: 12.18 Pa·s, though, they all contain the same error of membrane effect. Hence, it can be concluded: 1) the interaction between hyperelastic element and viscous media is time dependent, 2) one dimensional velocity flow does not comply with the mechanism fluid flow, 3) higher displacement speeds result in higher error in dynamic viscosity coefficient calculation.

Conclusion

First of all, the nonlinear hyperelastic and nonlinear viscoelastic schemes were introduced. The FEM formulation also was presented for nonlinear approach in solids and one dimensional fluid flow. Finally a viscoelastic mechanism (model) was developed and the experiments were performed to show time dependency and consistency of the proposed model.

It was also shown that for low speed deformation rate the viscoelasticity decreases and time dependency may be neglected. Therefore, the material can be treated as a hyperelastic material. On the contrary, for high speed deformation rate viscous media should be taken into consideration without which the behavior of the material would be inaccurate.

Experimental Outcome

Having performed experimental, it is necessary to make a summery to finalize general solution strategy for characterization procedure: 1—Soft materials can be classified mainly as hyperelastic and/or viscoelastic materials. 2—The time dependency of viscoelastic materials is due to the presence of a liquid or semi liquid media which absorbs the energy by internal friction. 3—The viscoelastic material is subjected to a large deformation which requires the presence of a hyperelastic element in its structure. 4—Viscoelastic behavior is the result of interaction of two elements with characteristic of hyperelasticity and viscoelasticity in certain conditions. 5—For every viscoelastic material, there is a limit of deformation speed up to which time dependency behavior is insignificant.

Method

Based on the outcome of experimental, analytical concepts and finite element simulation results, the method for characterization of soft materials especially biological tissues in-situ and in-vivo is built. Since the analytical and simulation assumptions are idealistic which cannot be provided in real condition and the experimental subjects are real objects-though they are artificial—the solution is based on the experimental results. As it was mentioned that a viscoelastic material consists of two elements with different behavior characteristics, it is required that the object to be presented with two properties which are generally nonlinear. To this end, the behavior of the object is divided in two behaviors: time dependent and time independent. It should be taken into account that the elasticity modulus of a hyperelastic material can be only presented by a curve of stress-strain as a nonlinear property of a nonlinear behaving material. Therefore, a number as elasticity modulus cannot be valid unless the range of deformation could be considered in the linear range that is not the case of large deformation of hyperelastic material including biological tissues.

Figure 31A:
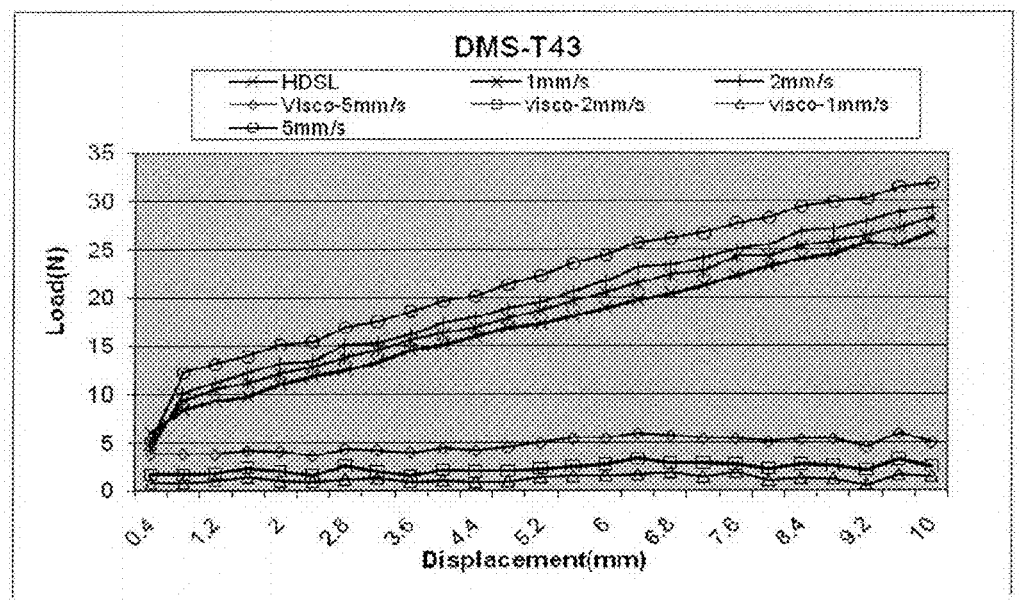
FIG. 31 illustrates the test curves of viscoelastic force, HDSL and viscosity force (31A) and the curves of viscosity force with trend lines (31B). of DMS-T43
Figure 31B:
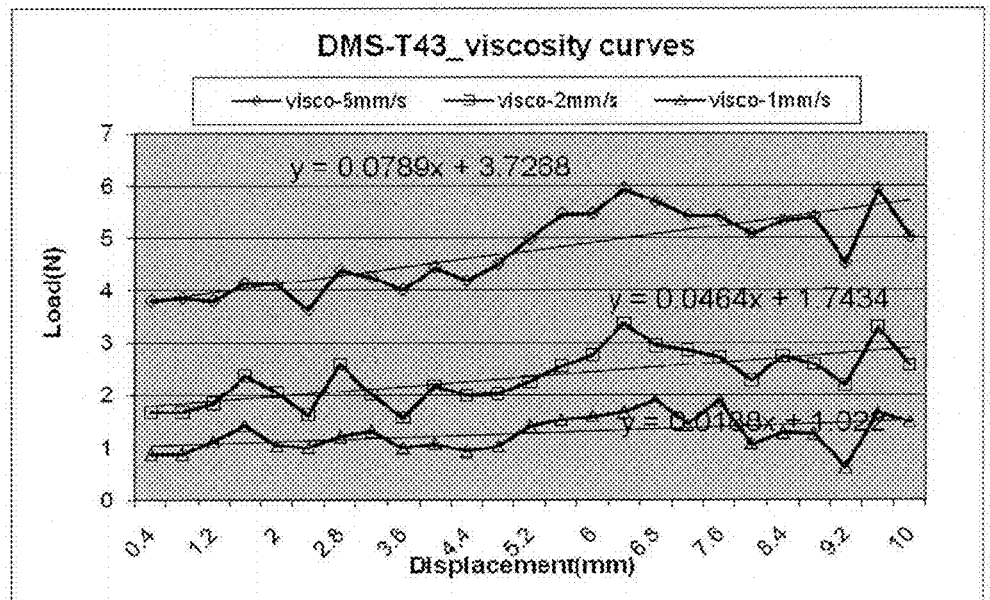
Figure 33A:
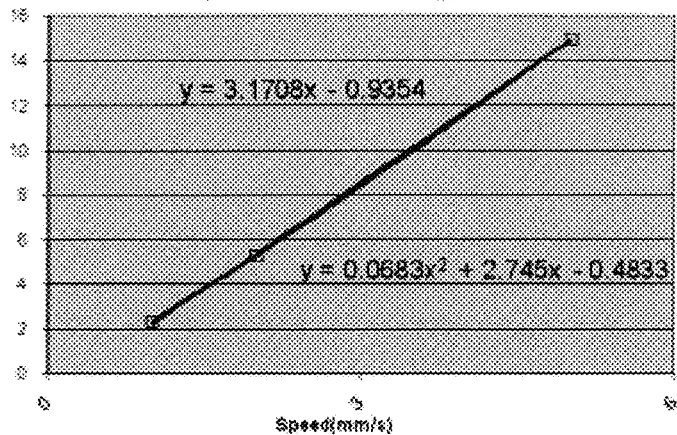
FIG. 33 illustrates the dissipation functions of DMS-T31 (33A) and DMS-T35 (33B) with respect to deformation speed.
Figure 33B:
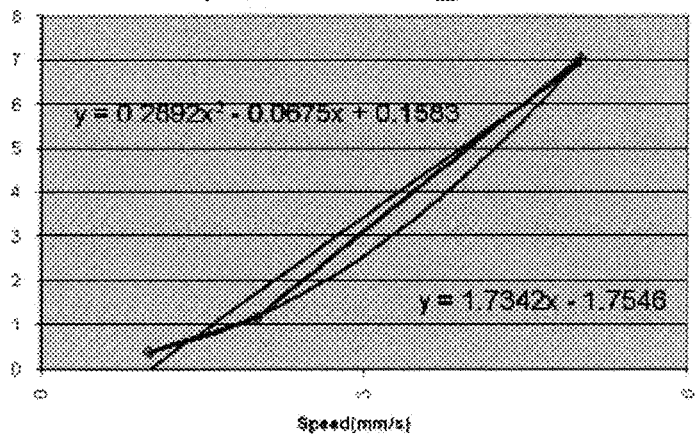
Figure 34A:
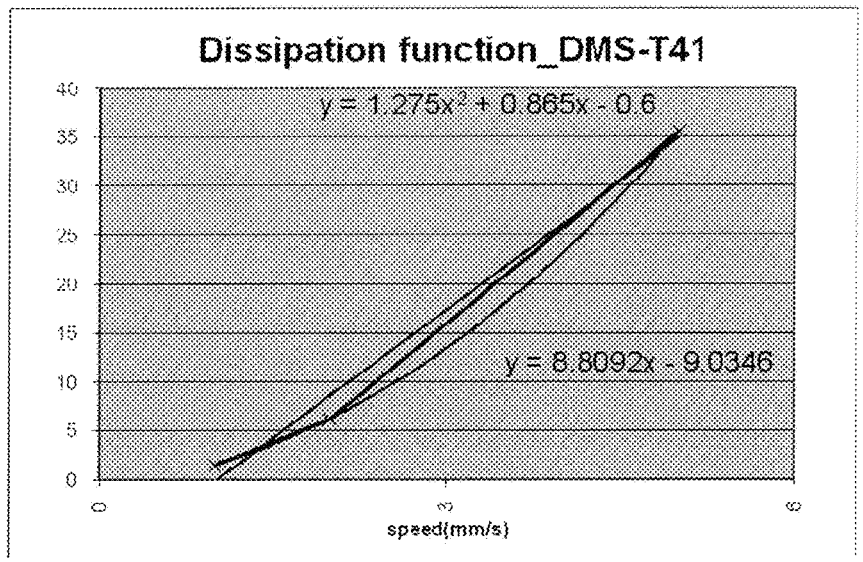
FIG. 34 illustrates the dissipations function of DMS-T41 (34A) and DMS-T41-2 (34B) with respect to deformation speed.
Figure 34B:
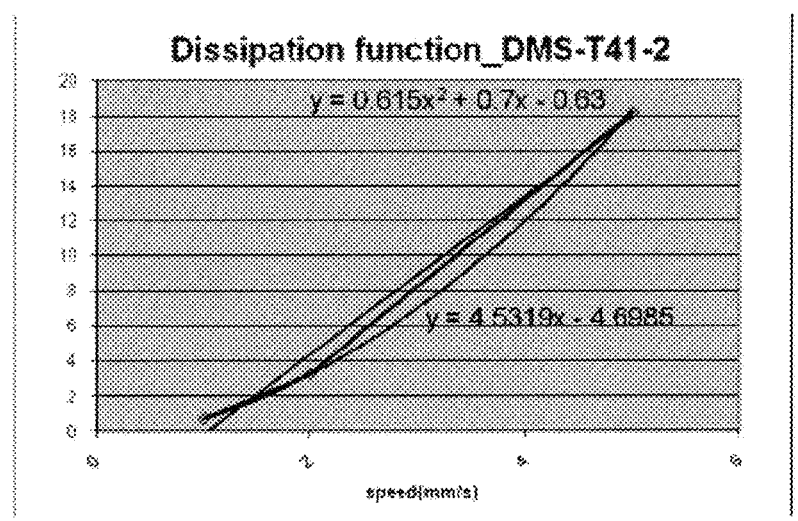

According to the curves of five tested objects, there is a limit of speed of deformation that the object behaves independent of time as a hyperelastic material, which is, whereas, called hyperelasticity deformation speed limit (HDSL). This speed deformation limit is 0.4 mm/s for DMS-T31, DMS-T41, DMS-T41-2, DMS-T43 and 1 mm/s for DMS-T35 (see FIG. 27B, FIG. 28A, FIG. 28B, FIG. 29A and FIG. 30A). Therefore, one curve in this range of deformation speed is used to calculate the nonlinear elastic modulus as it was discussed in nonlinear hyperelasticity. For viscoelasticity property, the relevant curve of force at the specific deformation speed which is in the range of time dependency; i.e. above the hyperelasticity speed limit is subtracted by the curve of hyperelasticity deformation speed limit (HDSL). The result is another curve which represents the force absorbed by the viscous media during deformation. FIG. 31A shows the curves of DMS-T43 including HDSL; viscoelastic curves of 1, 2 and 5 mm/s, and viscous force resulting from curves of 1, 2, 5 mm/s deformation speed. Consequently, the resulted curves are viscosity force curves, which are used for characterizing viscoelasticity property. In this regard the area under the curves of force-displacement is calculated which is the work or energy absorbed by viscous media. For simplicity of the calculation, the trend line of each curve is drawn and shown in FIG. 31B. By calculating the area enclosed between the trend line and horizontal axes, total energy absorbed by the viscous media during deformation is obtained. The average of dissipation of each deformation speed according to equation 43 is the result of the energy divided by time. The viscosity energy and average dissipation for five objects according to deformation speed are summarized in FIG. 32.

Figure 35A:
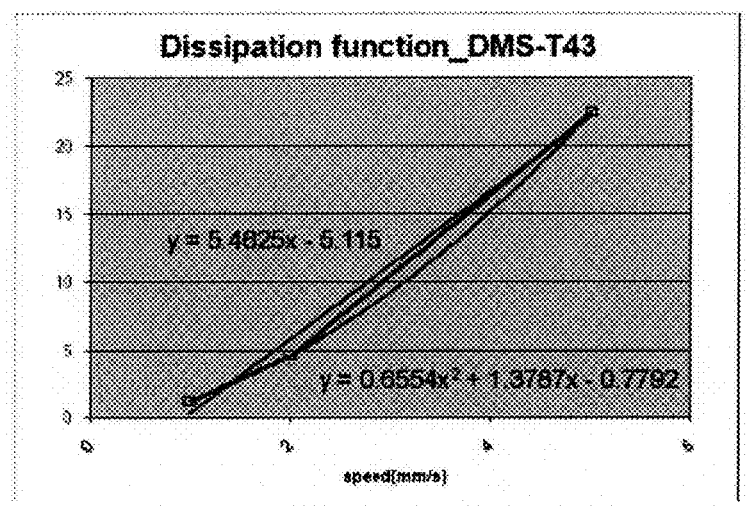
FIG. 35 illustrates the dissipation functions of DMS-T43 (35A) and dissipation functions of 5 experimental objects (35B) with respect to deformation speed.
Figure 35B:
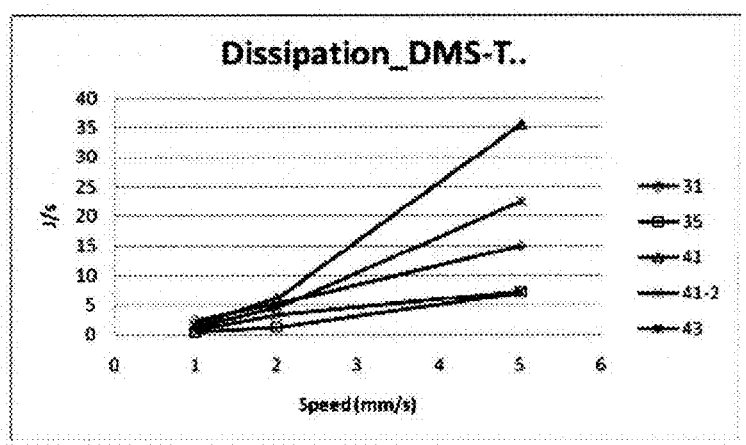

By drawing the curves of dissipation with respect to deformation speed, the viscoelastic behavior of each object can be characterized. The FIG. 33A, FIG. 33B, FIG. 34A, FIG. 34B and FIG. 35A show the dissipations of five objects with respect to deformation speed. Each curve is presented with trend line and polynomial trend curve for facilitating the study of viscoelastic behavior of the objects with respect to deformation speed. It can be seen that the curves of dissipations with respect to deformation speed is more likely comply with polynomial function with degree of two as it could be predicted according equation 35. Therefore, characterization of viscoelasticity of object requires at least three points on the curve of dissipation. FIG. 35B shows the dissipation of five objects together on one chart. It can be seen that the viscoelasticity of the objects decrease in descending manner DMS-T41, DMS-T43, DMS-T31, DMS-T41-2, DMS-T35 while the viscosity of the viscous media is 10000, 30000, 1000, 12500 and 5000 cStock, respectively. This confirms again that viscoelasticity is a property dependent on the interactive correlation of consisting elements of an object. Therefore, the general solution for characterizing a viscoelastic object is: 1—deforming the object and measuring the force and displacement with respect to time with four deformation speed; one as HDSL and three higher than HDSL, 2—calculating the hyperelasticity as a function of stress-strain, 3—calculating dissipation function with respect to deformation speed.

Figure 36:
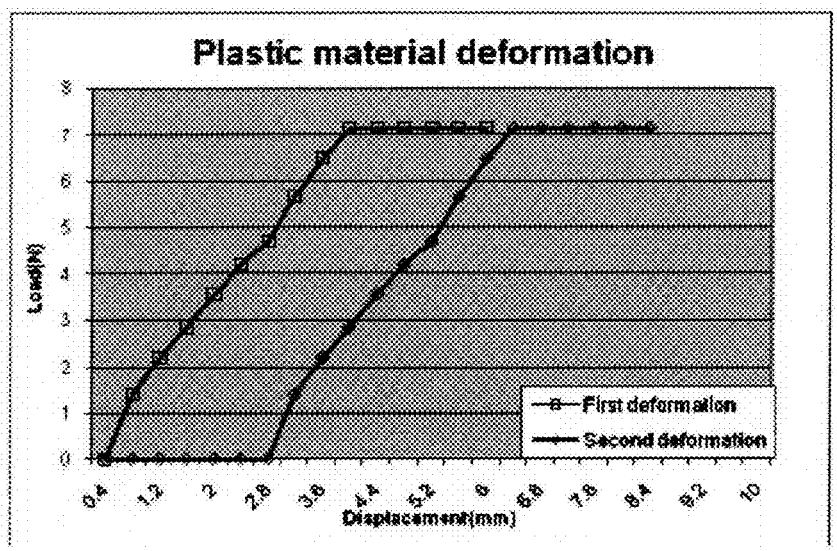
FIG. 36 illustrates the forces of first and second deformations of a plastic object.

Since elastic and hyperelastic materials are time independent, the second deformation curve with high speed coincides with the curve of low speed deformation. First and second deformations of viscoelastic materials were discussed in detail, therefore, the behavior of plastic material should be clarified. A plastic material behaves like an elastic material until certain limit and then yields and flows; therefore, the reaction is the resistance of semi-solid flowing. Consequently, the reaction force stays almost constant during deformation. FIG. 36 shows an example of behavior of a plastic material during first and second deformation with low and high speed deformation, respectively. In other words, plastic object can be treated like a viscoelastic object with the lack of a hyperelastic element. A plastic material also absorbs energy during deformation in the same manner of viscoelastic material but in viscoelastic material, part of the energy of deformation is stored by hyperelastic element which causes the return of the object to the first configuration in a certain period of time. Plastic material absorbs all the energy and waste it by the internal friction, therefore, it remains stable at the final configuration with the balance of total energy.

Having explained the characterization procedure for viscoelastic and plastic objects, it is essential to consider the circumstances on which characterization method is applied. The characterization system or any tactile sensing system has two duties to accomplish: characterizing soft materials qualitatively and quantitatively. The soft materials can be classified as: elastic materials, hyperelastic materials, viscoelastic materials, plastic materials and combinations of them. For performing the task of characterization qualitatively and quantitatively, at least two deformations with two different speeds are required. The first deformation with low speed in the range of HDSL results in characterization of material elasticity, hyperelasticity or plasticity quantitatively and second time deformation with high speed to: 1—confirm the quality of the object whether to be elastic or hyperelastic, 2—confirm the quality of the object whether to be plastic and characterize its plasticity quantitatively or 3—confirm the quality of the object whether to be viscoelastic and characterize its dissipation quantitatively at the deformation speed. In other words, first deformation with low speed characterizes the elastic or hyperelastic element of the object. Second deformation with high speed characterizes the other element of the object if it exists. In order to achieve a complete characterization of a viscoelastic object, dissipation function is required to be presented as a mathematical function with respect to deformation rate. Therefore two more point on the curve is required which means four deformations with different speeds are required, though second deformation is sufficient for most applications such as biological tissue.

Mechanisms

Having discussed the method and strategy of general solution which is performed by analyzer, the mechanisms are disclosed which performs the required deformations and measurements for any object in any configuration and any orientation including biological tissues in-situ and in-vivo. The specific procedure of each mechanism is also explained accordingly.

The characterization of materials is performed by deformation occurred by a compressive force and measuring the force and displacement with respect to time. In this regard, the target object is deformed by one of the mechanisms depending on the accessibility condition, contour of the object, concentration of stress, etc. Each mechanism uses its own specific control and analyzing method.

Figure 37:
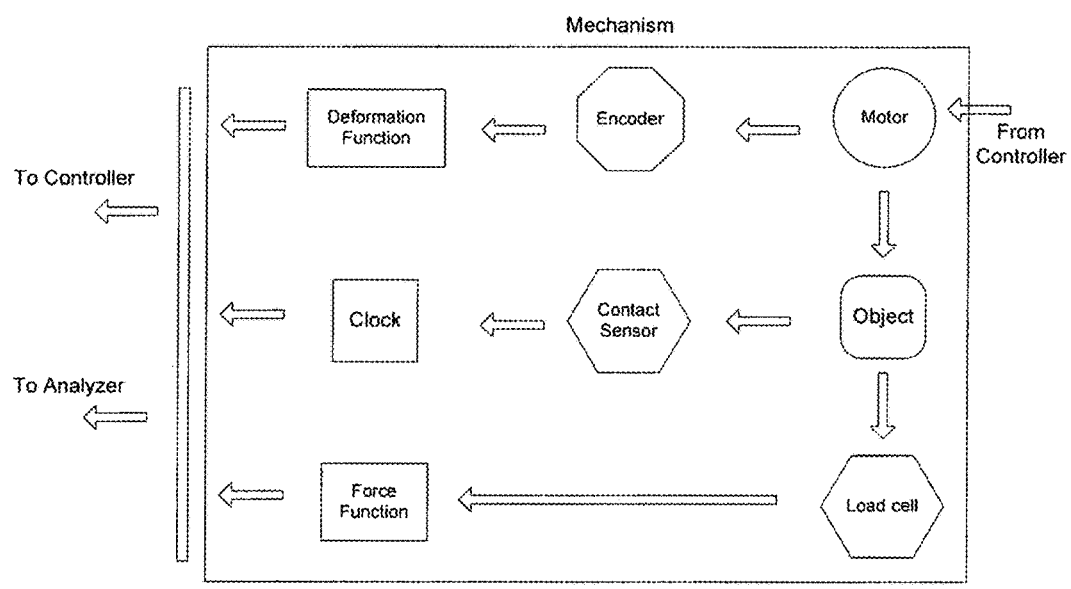
FIG. 37 illustrates the interrelations of parts of a general mechanism with object, controller and analyzer.

The diagram of a general mechanism of the system is shown in FIG. 37. The object is touched and deformed in one direction by means of a motor's shaft. The reaction force by the object is measured by the load cell. The displacement rate which is the result of the deformation of the target object is measured by an encoder. A contact sensor records the time of touch, force and displacement measurements. These measurements, which conform the functions of force and displacement with respect to time, are sent to analyzer.

The deformation rate is required to be in constant manner in order to allow the analyzer calculate the properties of the target object. Therefore, the controller regulates the speed of motor's shaft in order to maintain a constant displacement speed during deformation according to the behavior of the target object. For this purpose, the outputs of force and displacement sensors are sent to the controller, which regulates the speed and torque of the motor's shaft.

Standard Clamp Mechanism (SCM)

This mechanism grasps the object by means of two parallel clamping faces. Consequently, it is used for the objects with two parallel accessible surfaces. This mechanism is similar to typical test machines for elastic material characterization while the material behavior is within the linear range. SCM performs the characterization of the target object in the similar manner with several differences, e.g., nonlinear analyzing methods are applied to obtain nonlinear properties of the materials.

Figure 38:
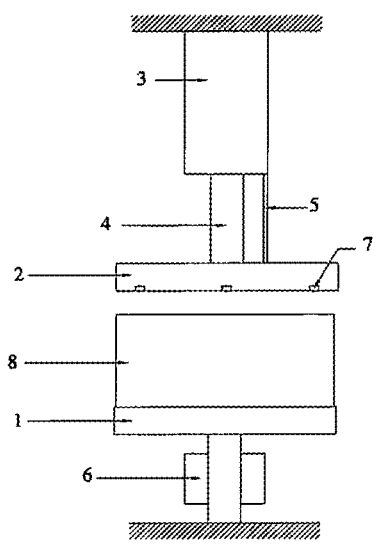
FIG. 38 illustrates the schematic of Standard clamping mechanism.

FIG. 38 shows the standard clamp mechanism (SCM). The mechanism applies the compressive force by two parallel clamping faces. One clamping face is fixed 1 and the other one 2 is driven by a DC motor 3. The driving shaft 4 of the motor is attached to a linear encoder 5 which measures the displacement of the shaft. The fixed clamping face is supported with a bar which is equipped with a load cell 6. The moving clamping face is equipped with a contact sensor 7. When the contact sensor touches the contour of the object 8, the time is set to zero. Eventually, the force and displacement sensors are synchronized for the zero level at the touch of the object. The result is the continuous functions of force and displacement with respect to time.

For characterizing the object by SCM, it is assumed that initial touched surfaces of the object remain unchanged during deformation. In another word, not only the deformation is taken place with reserving volume but also the contact surfaces are as well unchanged. Another assumption makes the necessity that the object to be isotropic; i.e. the properties of the material should be uniform and free of direction. The analyzer takes advantage of these assumptions in order to calculate the initial and final configuration in every time steps of the object to be used for determining its properties. Controller regulates the drivers torque in order to maintain constant deformation speeds.

Procedure of Analyzing for SCM

Since this mechanism is standard, the analyzing strategy can be considered a standard procedure. Therefore, for other mechanisms only the differences will be discussed.

The solution procedure for SCM is: 1—Setting first deformation speed and displacement limit, e.g. 0.2 mm/s and 5 mm. 2—Setting force limit for the object, e.g. 30N. 3—Starting deformation. 4—Recording the time and displacement at the touch point of the object by the contact sensor, e.g., 1.5 s and 1.2 mm. 5—Recording the force with respect to time and to displacement. 6—Retracting the moving clamp and wait for the object to return to the stand status. 7—Analyzing the results according analysis of non-linear hyperelasticity. 8—Monitoring the curves of force-displacement, stress-strain and elastic modulus-strain. 9—Setting second deformation speed, e.g., 3 mm/s. 10—Starting deformation. 11—Recording time and displacement of the touch point by the contact sensor. 12—Recording force with respect to time and displacement. 13—Retracting the moving clamp. 14—Analyzing the quality of the object, e.g., hyperelastic, plastic, etc. 15—Monitoring the curves of first and second deformation of force-displacement. 16—Concluding the quality of the object by comparing two curves of step 15. 17—Monitoring the properties of object whether it is elastic or hyperelastic, curves of stress-strain and modulus-strain; whether it is plastic, curve of stress-strain and dissipation at the deformation speed; whether it is viscoelastic, curve of stress-strain at the low speed and dissipation at the high deformation speed. 18—Calculating two other deformation speeds if complete characterization of the dissipation function of viscoelastic object, if exist, is required and repeating step 9 to 17.

General Clamp Mechanism (GCM)

Figure 39A:
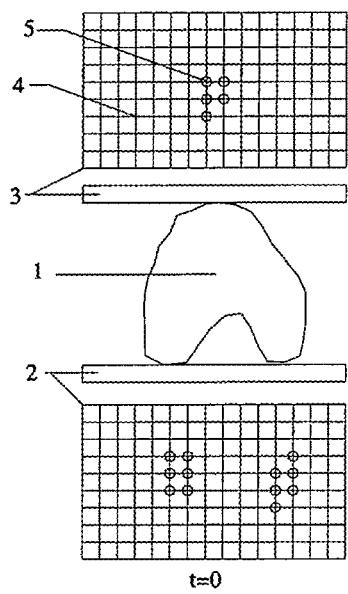
FIG. 39 illustrates the contact history of an arbitrary irregular object deformed by General clamp mechanism at time zero (4A) and $t=t_n$ (4B).
Figure 39B:
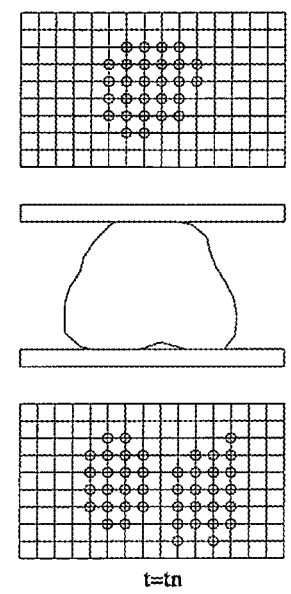

FIG. 39A shows the clamping faces and the object of General clamp mechanism; the other parts of the mechanism are similar to the parts of SCM. The object 1 is grasped by fixed clamping face 2 and moving clamping face 3. This mechanism is used when the target object has access from two opposite sides but does not have regular profile of surfaces to comply with clamping faces. As a result, one contact of the object does not provide enough geometry information to be used for evaluation of its volume, which is necessary for determining the properties of the object. Therefore, the clamping faces are equipped with arrays of contact sensors 4. When the faces touch the object respective points of touch trig the sensors 5 and map the profile of the object's surface at the time zero. Along with deformation, the changes of geometry bring other contact sensors in touch with the object. Thus, the deformation history and contact history of the object provide data for the analyzer to evaluate deformed volume with respect to time. In other words, the analyzer evaluate the geometry of the object with respect to time. time FIG. 19B shows the contact history of the irregular object deformed by GCM at time t=$t_n$. As it is shown, the irregular geometry of the object leads to irregular deformation considering that the deformation is assumed uniform. The analyzer uses these data to calculate the distribution of the deformation rate and force within the volume and nonlinear properties of the object.

Procedure of Analyzing for GCM

Figure 40A:
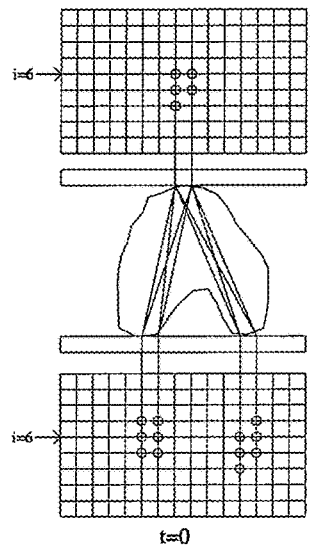
FIG. 40 illustrates the deformed planes evaluation by means of contact history by General clamp mechanism at time $t=0$ (40A and 40B) and $t=t_n$ (40C and 40D).
Figure 40B:
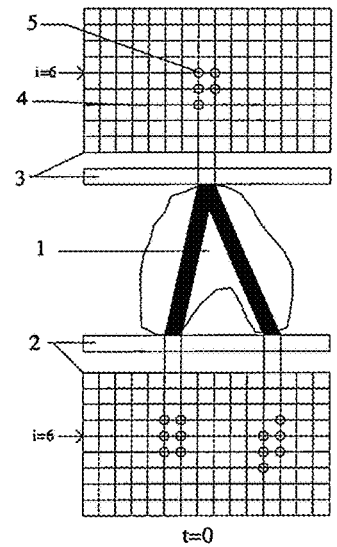
Figure 40C:
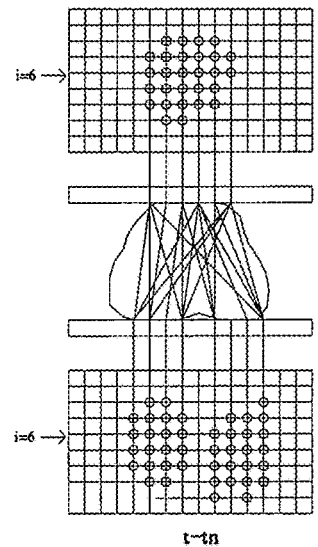
Figure 40D:
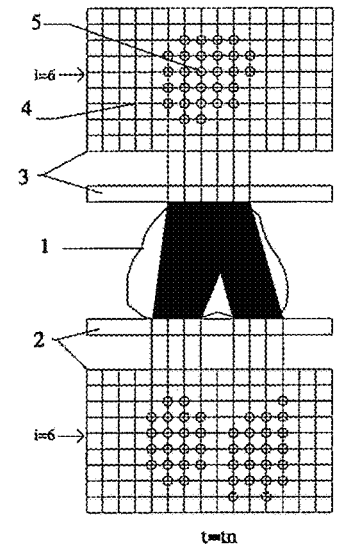

GCM solution strategy is similar to SCM with the exception that the geometry of the object is not known. Therefore, the volume of the object which is deformed due to the compressive force is unknown. In this regard the array of contact sensors are provided with the clamps to map the topography of the object during deformation. By dividing the volume of the object to planes and using relevant contact sensors for each time step, the topography of the object in plane and consequently in 3D is evaluated. FIG. 40A shows the procedure of evaluation of the volume in plane indicated with a flesh (j=6) at the time zero. FIG. 40B shows the evaluated volume by the analyzer at time zero. The object 1 is deformed by fixed clamping face 2 and moving clamping face 3. The untrigged contact sensors 4 are identified from trigged contact sensors 5 by analyzer. FIG. 40C and FIG. 40D show the evaluation procedure for the same object at the time step $t_n$. In other words, for each contact sensor at any time there is an output of zero or one which refers to intrigued and trigged status, respectively. Therefore, the status of each contact sensor is a function of position and time which returns zero or one, i.e., $f_m(i, j, t)=0$ or $f_f(i, j, t)=1$; where $f_m$ is the function relevant to moving clamp, $f_f$ is the function relevant to fixed clamp, i is the number of row, j is the number of column of the array and t is time. Consequently, the procedure of GCM has an extra step, i.e., 6a, after step 6 and before step 7 for calculating the geometry and volume of the object as functions of time involved in the deformation during time interval to be used for step 7.

Robust Clamp Mechanism (RCM)

When the shape of the target object provides non-uniform deformation due to sharp edges and concentrated stresses, GCM leads to certain errors. This is because that the distribution of force cannot be sensed by one single load cell. In this regard, robust clamp mechanism is designed which is shown in FIG. 41A and FIG. 41B. The mechanism is equipped with arrays of force sensors 1 on both fixed clamping face 2 and moving clamping face 3 in addition to contact sensors. When the object 4 is touched by the mechanism, the contrast of trigged contact sensors 5 and unrigged contact sensors 6 map the surface of the object with contact with the mechanism. Therefore, not only the geometry of the object is evaluated during deformation also the concentration of stress within the volume of the object is calculated by using distribution of force measured by force sensors. Characterization of such an object results in properties as functions of space status, i.e. geometry, material and load. The contact sensors are used provided that the threshold of force sensors are not appropriate for measuring contact history, otherwise, instead of contact sensors, force sensors are used to increase the resolution. The other parts of the mechanism are the same of SCM.

Procedure of Analyzing for RCM

Analyzing procedure of RCM is similar to GCM with the difference that the assumption of uniform distributed force on the clamp cannot be applied due to geometry of the object which creates the concentration of stress in some part of the object. In this regard, the array of force sensors within the clamps faces provides the information of distributed force on the faces quantitatively. Therefore, another function in addition to contact sensors function, is created by measuring the force of every single force sensor in every time step of analysis, i.e., $F_1(i, j, t)=f$ N. The analyzer uses the pattern of force sensors and contact sensors in order to calculate the deformation performed within the entire evaluated volume of the object. FIG. 41A and FIG. 41B show the function of force sensor array at time 1 and 3 of deformation for one of the objects. Consequently, the procedure of RCM is similar to GCM but the solution of the step 6a between step 6 and 7 of SCM is more complicated and the function of force array instead of load cell output is used for analyses.

Pre-Tailored Clamp Mechanism (PCM)

Figure 42A:
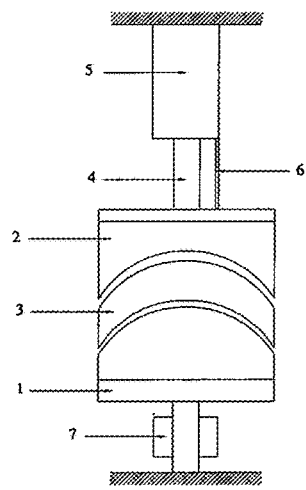
FIG. 42 illustrates the schematic of Pre-tailored clamp mechanism with changeable clamping faces with three different objects (42A, 42B and 42C), the array of force sensors installed on fixed clamping face (42D) and the array of contact sensors installed on pre-tailored clamping faces (42E).
Figure 42B:
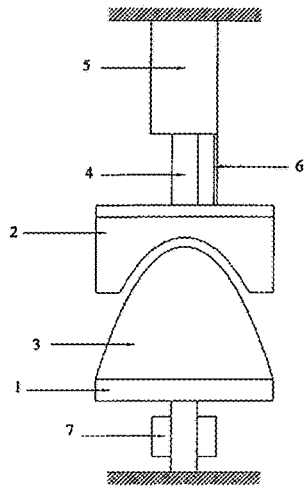
Figure 42C:
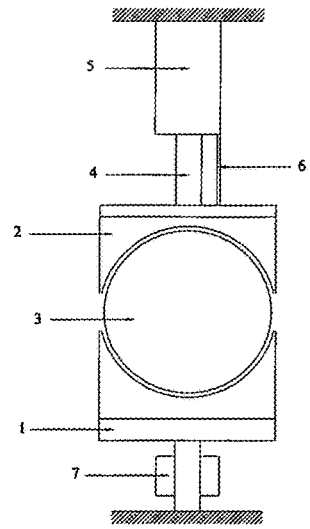

The FIG. 42A, FIG. 42B and FIG. 42C show Pre-tailored clamp mechanisms according the profile of different objects. This mechanism has the same characterization of GCM, except that the fixed clamping face 1 and moving clamping face 2 are changeable according to the contour of accessible surfaces of the target object 3. Deformation is performed by the driving shaft 4 of a DC motor 5 and displacement is measured by an encoder 6. The force is measured by both load cell 7 and the force sensors of the array installed within fixed clamping face.

Figure 42D:
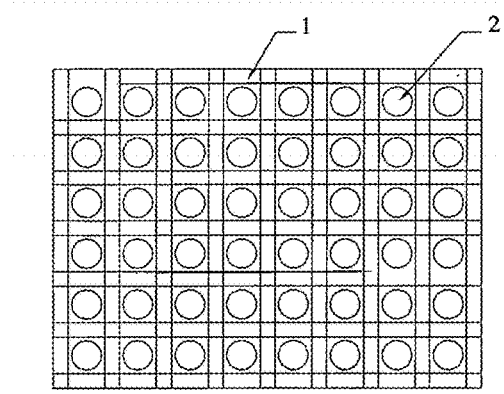

The array of fixed clamping face is shown in FIG. 42D. The fixed clamping face 1 is equipped with array of force contact 2.

Figure 42E:
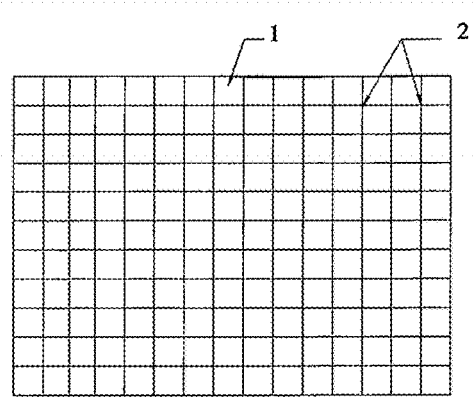

FIG. 42E shows the pre-tailored clamping faces 1 equipped with array of contact sensors 2. Consequently, each mechanism uses three array of sensors: one array of force sensors within fixed clamping faces under the lower pre-tailored clamping face and two array of contact sensors within two pre-tailored clamping faces touching the target object. The mechanism functions in the same manner that GCM does while the pre-tailored clamping faces allow the mechanism to obtain more precise data from the object during deformation. In addition, this mechanism provides the possibility for testing and characterizing objects with specific manners of loading and deformation. In other words, not only the properties of the object which is dependent on the materials disregarding its geometry, but also the behavior of any object, which is function of material, geometry and loading, can be determined by this mechanism. One of the advantages of this mechanism is the possibility of testing the objects which might be damaged by significant deformation. For overcoming the difficulty of defining the concentration of stress in the object, the fixed clamping face is equipped with an array of force sensors (gauges) to provide force distribution during deformation. Therefore, the behavior of the object, that may be non-uniform within the volume, can be characterized by the analyzer.

Procedure of Analyzing for PCM

The procedure for analyzing an object with PCM is completely similar to RCM but in this case the object geometry is known and volume of the object is not required to be calculated by preparing the pattern of contact and force sensors. Since the concentration of the stress can be evaluated by only one array of force sensors, the calculation of the step 6a is more similar to GCM rather than RCM. On the other hand, the hyperelasticity should be computed as RCM by taking into account the distribution of the force on the object surface. It should be taken into account that PCM is used for specific objects including biological organs; therefore, the deformation is more limited than other clamp mechanisms.

General Jaw Mechanism (GJM)

Figure 43A:
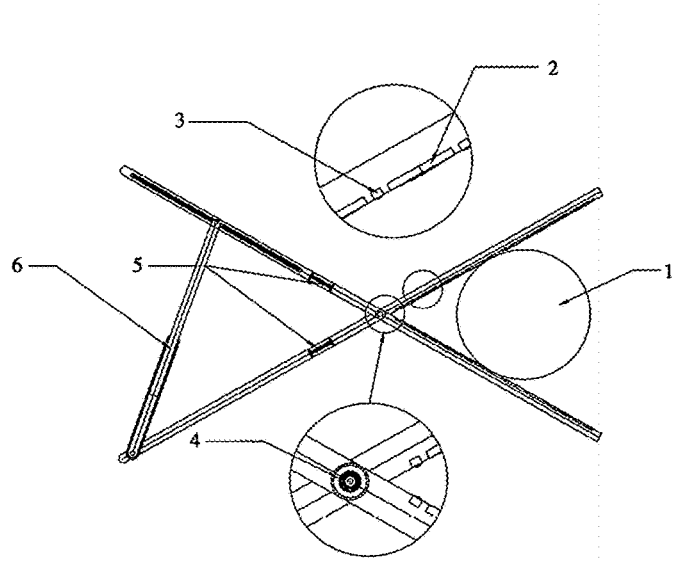
FIG. 43 illustrates the details of General jaw mechanism (43A) and the variation of the forces on an arbitrary object deformed by the faces of General jaw mechanism (43B and 43C).

The details of GJM are shown in FIG. 43A. This mechanism applies the compressive force to the target object 1 by means of two hinged faces which conform a jaw. The faces of the jaw are equipped with force sensors 2 and contact sensors 3. The mechanism uses an angular displacement sensor (encoder) 4 for measuring deformation. In addition to force sensors on the jaw faces, the mechanism uses another force sensor 5 on the driver levers. The torque and speed of the motor 6 which applies the force to the jaw is regulated by controller, though the jaw mechanisms may be driven manually provided that a device controls and provides different constant angular speed of deformation. In this case, the user should be aware of limit of applied force in order to prevent any possible damage to the object. in case of sensitive force sensors with low threshold, the contact sensors can be replaced with force sensors.

Figure 43B:
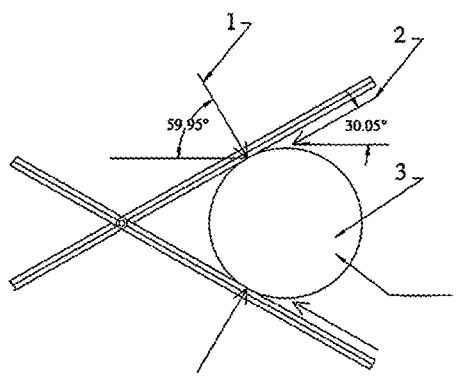
Figure 43C:
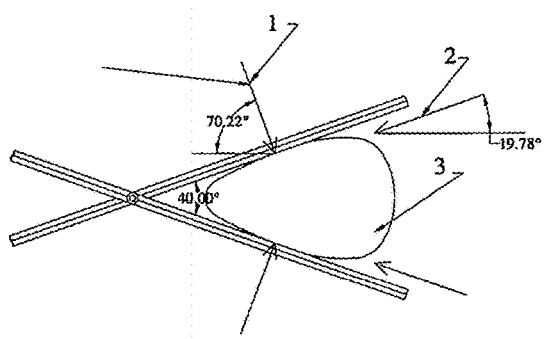

Thus, during deformation, force sensor of driver's shaft provides the data of total applied force and regulate the driver's torque within the limits range of force prescribed for the object. Since the deformation of the object in a jaw does not comply linearly with angular displacement, contact surface of the object is varying while the directions of the forces are continuously changing with respect to the axes of the object. Therefore, the force sensors embedded in the jaw's faces are required to synchronize the forces on the objects with the total sensed force by motor shaft's sensor. In other words, the contact force on the object of any point of contact is result of friction force which is applied along with face of jaw and reaction force which is perpendicular to the jaw's face. These forces are varying in magnitude and direction with respect to the last deformed configuration. FIG. 43B and FIG. 43C show the variation of the reaction forces 1 and friction forces 2 on an object 3 deformed by the faces of general jaw mechanism.

One of the most important advantages of this mechanism is the capability to be integrated with end effectors of robots and minimally invasive surgery tools.

Procedure of Analyzing for GJM

Analyzing procedure of GJM is the same as GCM with the exception of coordinate system for solving the equations. GCM analyzer uses Cartesian coordinates system and deformation is taking place in longitude while GJM analyzer uses cylindrical coordinate system and deformation is angular. Therefore, the deformation speed is considered as angular velocity and is measured in rad/s.

The arrays of force and contact sensors provide the information about object geometry during deformation as functions of time. Therefore, the mechanism can grasp any object provided that the faces of jaw apply considerable friction force to maintain the object between the jaws during deformation. To this end, the faces of jaws are equipped with tooth to hold the object in contact with mechanism. If any slip happens, the contact sensors are able to detect it. In case of occurrence of any slip, the grasping should be repeated.

Pre-Tailored Jaw Mechanism (PJM)

Figure 44A:
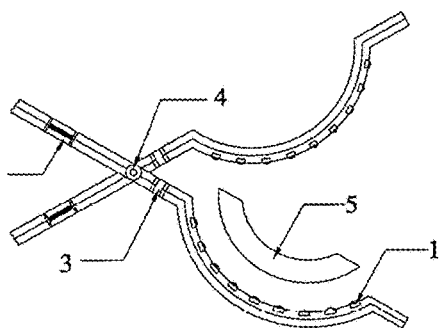
FIG. 44 illustrates two Pre-tailored jaw mechanisms with changeable jaw faces (44A and 44B).
Figure 44B:
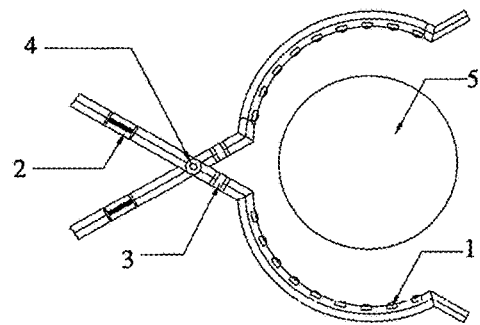

This mechanism functions in the same manner of GJM but the faces of the jaw are changeable with pre-tailored faces with regular curved cross sections. FIG. 44A and FIG. 44B show two PJM changeable jaws. The faces are equipped with contact sensors 1 to trace the deformation of the object during deformation. On each lever of jaw a force sensor 2 is installed to measure applied force. Each lever is provided with a connection 3 for fixing the changeable jaws. Similar to GJM an encoder 4 measures the angular displacement. This mechanism is used when the contour of the target object 5 is curved.

Procedure of Analyzing for PJM

PJM contrary to GJM is designed for characterizing the object with known geometry. Though these objects can be sensed precisely by GJM, it requires that the objects undergo certain deformation which might be out of their allowable range. Also prevent this mechanism concentrated deformation on the objects due to conformity of the jaw's profile with object's contour. Moreover, it provides deformation on the objects which have very thin and fragile skin and may fail to deform under GJM. Finally, it can deform the objects without friction required between the jaw's face and contour of object by using GJM. It should be mentioned that the profile of the jaw is not required to be at the same curvature of the object, because the contact sensors installed on the jaw's faces provide the information of the geometry of the object during deformation. Therefore, the procedure of the analyzer of this mechanism follows the procedure of analyzer of PCM with consideration of using cylindrical coordinate of GJM.

Rigid Probe Mechanism (RPM)

The characterization of an object with one access surface is impossible by using clamp or jaw mechanisms because these mechanisms require two access surfaces in order to touch and apply force to the object. In this regard, probe mechanism is designed to characterize the properties of the target object by applying compressive force on one access surface of the object with assumption that the opposite surface of the object is fixed.

Figure 45:
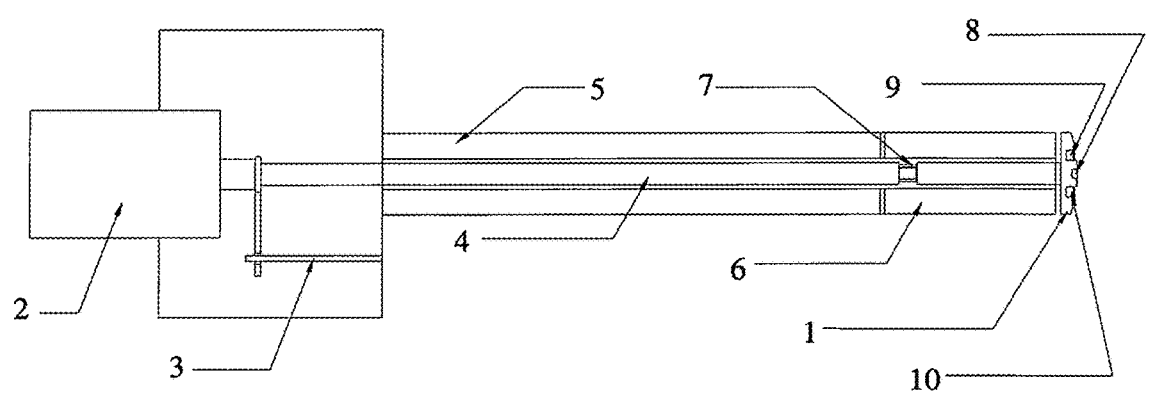
FIG. 45 illustrates the details of the Rigid probe mechanism.

FIG. 45 shows the RPM. The mechanism uses a probe 1 to deform the target object. The probe is pushed by a linear motor 2 of which the shaft is attached to a linear encoder 3. The force is transmitted by a rigid rod 4 which passes through a solid tube 5 and rigid guide 6. The probe is provided with a load cell 7 which measures applied force to the object. On the head of the probe, a contact sensor 8 is installed. At the time of touching the object by the probe, the contact sensor is trigged and records the time for which the functions of force and displacement are set to zero. Since during the characterization of the object by probe mechanism, the thickness of the object is unknown, an ultrasonic thickness meter is provided of which emitter 9 and receiver 10 are installed on the probe head. When the probe touches the object and is securely in contact of the surface of the object, the controller initiates the meter to measure the thickness of the object, which will be used by analyzer for calculating the properties of the object.

The deformation is taken place twice with low and high deformation speed, unless more deformation are required, in the same manner of other mechanisms. The controller regulates the deformation speed by adjusting the torque of the motor with respect to the behavior of the object.

The present mechanism is suitable to characterize the object in-situ and iv-vivo with limited access. They can be integrated with endoscope or being used with endoscope for minimally invasive surgery and with special robots used for robotic assisted surgery.

Flexible Probe Mechanism (FPM)

Figure 46A:
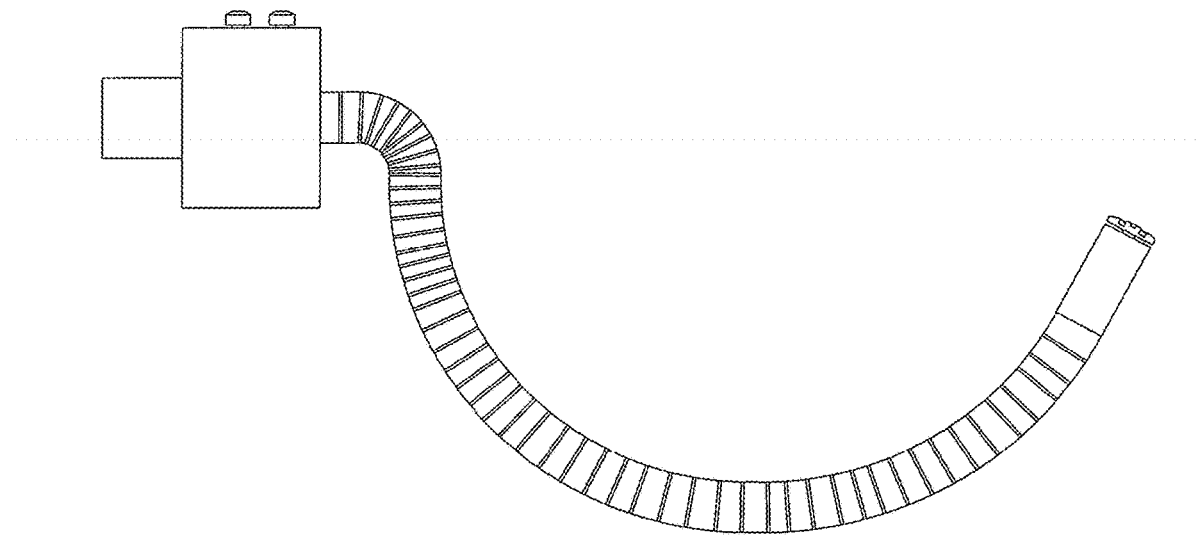
FIG. 46 illustrates the schematic of Flexible probe mechanism (46A) and its details (46B).
Figure 46B:
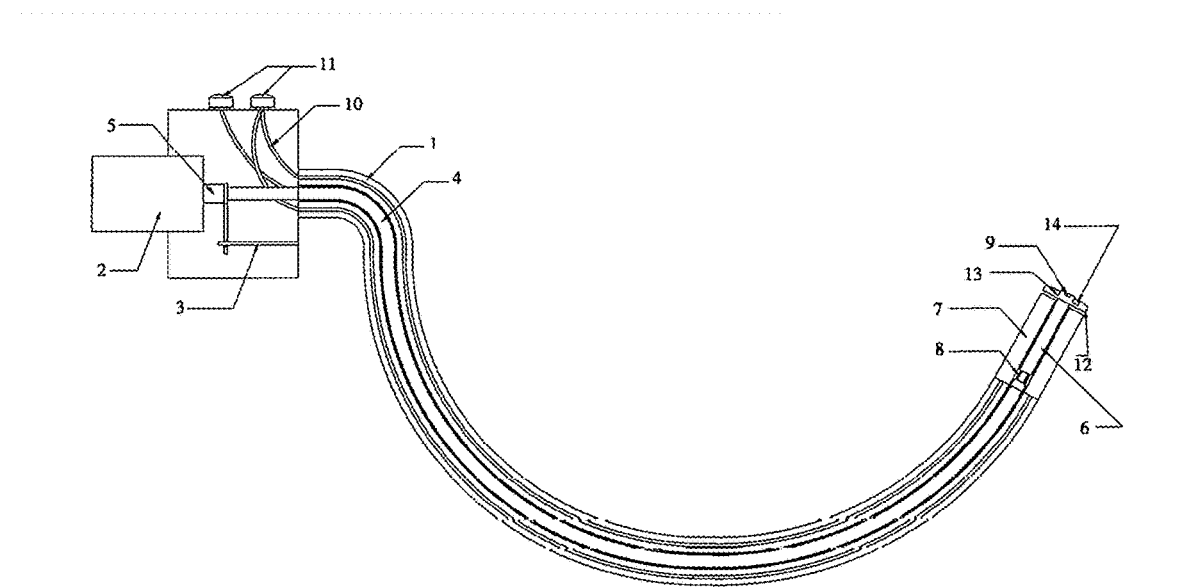

This mechanism functions in the same manner of RPM. In addition, the body of the mechanism is flexible to be used in narrow spaces. FIG. 46A shows the schematic of FPM. The details of FPM are shown in FIG. 46B. The probe mechanism consists of a flexible tube 1 which can be easily maneuvered to the target object's surface by passing through holes and narrow channels. At the fixed end of the tube a linear motor 2 equipped with linear encoder 3 is installed. A flexible rod 4 is passed through the flexible tube and is attached from one side to the shaft 5 of the linear motor, and from other side to the rigid piston 6. The surface of the rod is covered by graphite in order to minimize the friction between the rod and the tube. At the free end of the tube, a rigid shallow cylinder is installed in a manner that provides a rigid guide 7 for the rigid piston to slide freely without deviation from longitude axis. A load cell 8 is attached to the free end of the piston. A cap is installed on the head of the piston which is equipped with a contact sensor 9.

The flexible tube is provided with eight longitude holes in its wall. Four of the holes are the guides for steering wires 10 which are used to steer the tube to the desired position perpendicular to the object surface with minimum gap in order to maximize the deformation range by means of steering levers 11. The other four holes are equipped with four longitude resistive sensors. These sensors are sensitive to longitude deformation. When the tube is curved upward, upper sensor is compressed and its resistance is decreased and the sensor in below is stretched and its resistance is increased. The holes of resistive sensors are arranged on the quadrants of a cycle. Therefore, the final position of the free end of the tube can be obtained during deformation by the difference of sensors outputs.

The tube is driven by the steering levers and is locked to the desired position at the target object. The motor shaft pushes the piston perpendicular to the object's surface and pulls it back when the deformation is achieved. The object is deformed by the probe's head 12 while the linear encoder measures the displacement and load cell measures applied force to the object with respect to time of which reference is set by contact sensor.

Figure 47A:
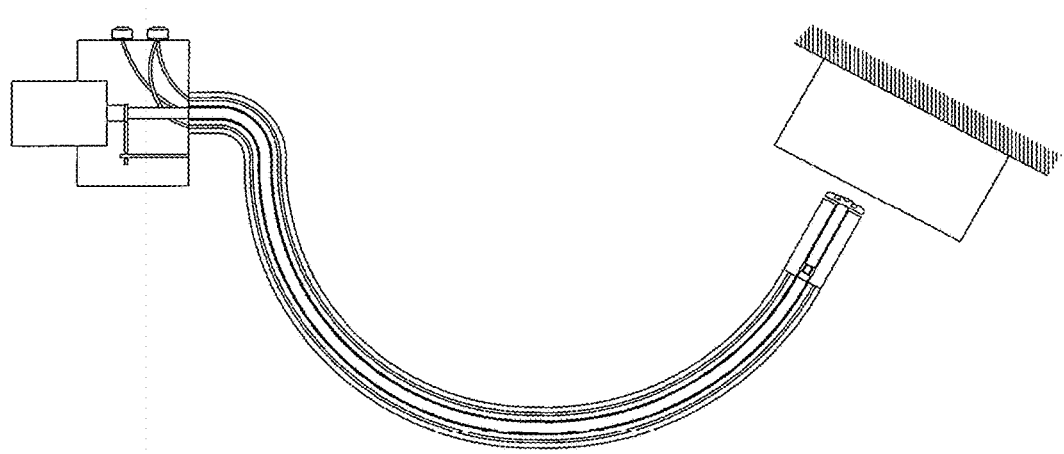
FIG. 47 illustrates Flexible probe mechanism orientation with respect to the target object before (47A) and after deformation (47B).
Figure 47B:
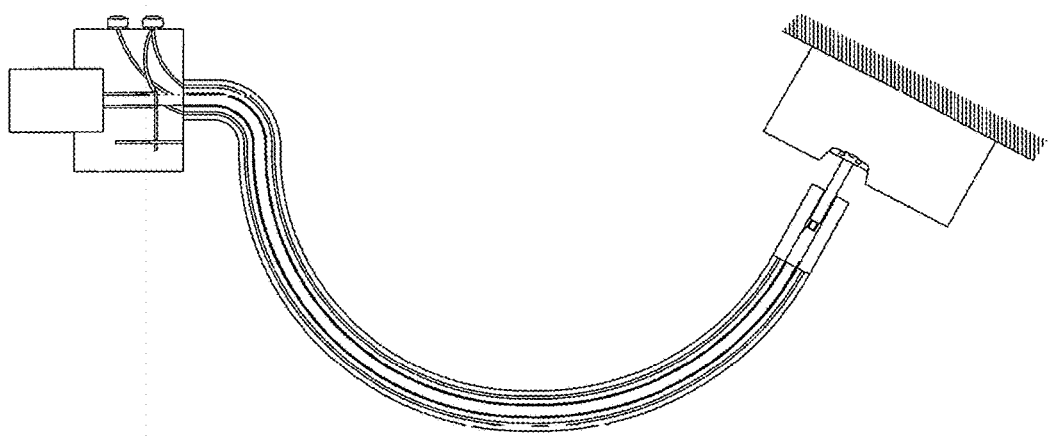

The deformation of the locked tube during the deformation of the object is calculated by the longitude resistive sensors. More precisely, the change of head position of the mechanism during deformation due to the reaction of applied force is measured by resistive sensors. In this manner, the real deformation of the object with respect to time can be calculated at any time. Similar to other mechanisms, the displacement and force functions with respect to time are provided for analyzer to calculate and display the properties of the object. The orientations of the probe relative to the object before and after deformation are shown in FIG. 47A and FIG. 47B, respectively.

Since during the characterization of the object by probe mechanism, the thickness of the object is unknown, an ultrasonic thickness meter is provided of which emitter 13 and receiver 14 are installed on the probe head. When the probe touches the object and is securely in contact of the surface of the object, the controller initiates the meter to measure the thickness of the object, which will be used by analyzer for calculating the properties of the object.

The deformation is taken place twice with low and high deformation speed, in the same manner of other mechanisms. The controller regulates the deformation speed by adjusting the torque of the motor with respect to the behavior of the object.

The present mechanism is not only suitable for being integrated with endoscopic apparatus but also can be used to diagnose the internal tissues of which mechanical properties are changed under effect of tumor, cancer, infection, etc. The mechanism can be used for robotic assisted surgery and tele-surgery as well as for special robots. The mechanism can be also used to diagnostics of disorders such as: 77fibrium, miium, ectopic pregnancy and retained placenta.

Jaw-Probe Mechanism (JPM)

Figure 48A:
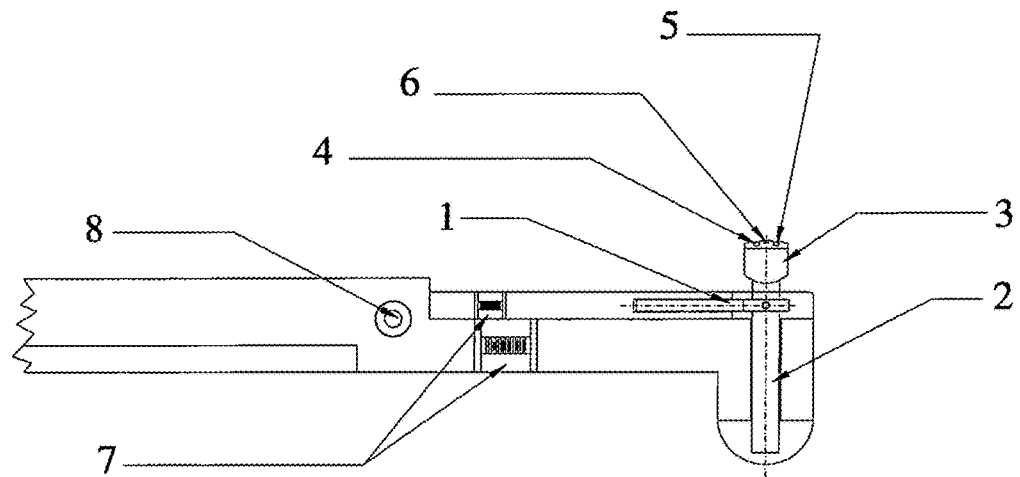
FIG. 48 illustrates the details of Probe-jaw mechanism at displacement zero (48A) and the mechanism after achieving certain deformation (48B).
Figure 48B:
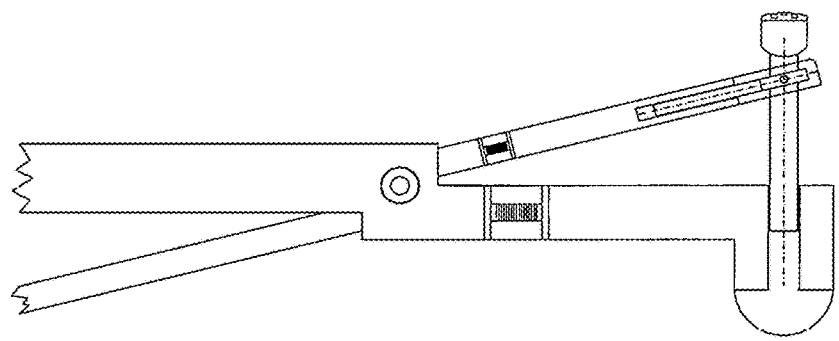

Jaw-probe mechanism is a combination of jaw and probe mechanisms. Since in some circumstances, like inside pipes, narrow channels, stomach, etc., the probe mechanism cannot be appropriately maneuvered, the JPM is designed to overcome the difficulty of accessibility through narrow spaces. FIG. 48A shows the details of JPM. The mechanism uses a piston-cylinder 1 for transmitting the force from jaw to the probe and another piston-cylinder 2 for maintaining the vertical alignment of the probe 3. As other probe mechanism, PJM uses an ultrasonic thickness meter to measure the thickness of the object. The emitter 4 and receiver 5 are installed on the surface of the probe besides a contact sensor 6. The force sensors 7, on this mechanism, are installed on both jaw levers: on the driving lever for measuring the applied force and on the base lever for controlling smoothness of the movement of the probe. An encoder 8 measures the angular displacement which is converted to linear displacement by the analyzer. FIG. 48B illustrates the mechanism after having achieved a certain deformation.

Procedure of Analyzing for RPM, FPM and PJM

The procedure which the analyzer of RPM uses is the exact procedure of SCM. The only difference is that the analyzer uses the output of ultrasonic thickness meter for complete the data of geometry of the object before starting any analysis. All probe mechanisms function in the same manner and their difference is the condition of accessibility of the object. For this reason the probe mechanisms are appropriate mechanism for using on biological tissue by minimally invasive and robotic assisted surgery. all probe mechanism are equipped with four more contact sensors on the quadrant of a cycle to record the touch time for controlling the perpendicularity of the probe with the surface of the object. Thus simultaneous touch time of four contact sensors means that the probe is perpendicular to the object; otherwise the deviation is measured with the difference of touch time of the sensors at the other side of the probe.

Pre-Tailored Probe Mechanism (PPM)

PPM is a combination of PCM and RPM. The structure of PPM is the structure of RPM but the probe is replaced with pre-tailored face on which several probes are installed and function in the same manner of a single probe. In other words, the PPM is combination of several RPM which are arranged according to contour of objects surface. The pre-tailored clamp consisting probes is driven by one single motor and displacement is measured by one linear encoder. This mechanism is appropriate for lump and tumor detection. Each probe is equipped with an independent ultrasonic thickness meter. the mechanism Self-Tailored Probe Mechanism (SPM)

SPM is a combination of GCM and RPM. The RPM are arranged on a 2D array. At the adjacent of the target object, perpendicular to the surface of the object, the mechanism initiate the motor of each individual probe with low speed until each one touches the surface of the object where the motor is stopped and the position of the probe and consequently the geometry of the object relative to the position of the individual probe on the array is recorded. When all individual probes touched the surface of the target object, the mechanism initiate the procedure of characterizing the object by performing the deformation by all probes synchronized with the same speed. Each probe is equipped with an independent ultrasonic thickness meter. In other words, the mechanism is the combination of several RPMs which are arranged in a 2D array.

The analyzer combines the results of all probes and provides a complete characterization of the object including the undeformed geometry of the object.

Procedure of Analyzing for PPM and SPM

The procedure of PPM and SPM is similar to RPM with few differences. Any individual probe of these two mechanisms is analyzed according to the procedure of RPM but their results are combined by analyzer for the complete characterization.

Controller

Controller plays a very important role in the performance of the system. The major duties of the controller are: 1—Regulating the torque and speed of the motor shaft according the behavior of the object and preset parameters such as deformation speed via the motor's driver. 2—Control the torque and displacement of the shaft within the limits of the allowable range preset by user according the target object such as limit of applied force and displacement. 3—Regulating the speed of the motor shaft before the contact of the mechanism with the object in order to prevent any effect of impact. 4—Apply appropriate procedure of deformation and analyzing method according to each mechanism. 5—Providing the facility for user to interact with the system. 6—Performing the self test and control the performance of the system regarding the procedure and support the user with appropriate feedbacks.

Since the deformation is required to be performed with preset deformation speed, the torque of the motor should be regulates according the resistance of the object against the deforming force. To this end, the controller uses the output of the encoder and calculates the speed of deformation, then compares it with the desired one. Consequently, the controller performs the compensation the error by increasing or decreasing the power of the motor in order to maintain the speed of deformation constant. For this purpose, the controller uses PID method for the first deformation. For the second deformation, the controller takes advantage the pattern of the first deformation to regulate the motor's torque with less error and more precision.

Soft materials, especially biological tissues may be damaged due to extra load or deformation. Therefore, the limit of force and displacement of the motor shaft is preset by the user within the secure range. The controller applies a safe margin to stop the motor before reaching to the secure limit of load or displacement.

An impact of the mechanism of the system with the object with speed more than a certain limit may cause damage to both, the mechanism and object. The controller drives the motor shaft very slowly during the first deformation and records the position at which the contact has occurred. For the next deformation, the controller regulates the speed of the shaft very slowly until the touch point and then start to drive it at the preset speed.

Depending on geometry, accessible surface and certain conditions, the sensing and characterization of objects should be performed by appropriate mechanism. The procedure of deformation for each mechanism is conducted and followed by controller.

For initiating the sensing and characterization process, the parameters of the system function should be set. This task is achieved by controller by providing human-machine interface. In addition, the controller records the data in a certain manner so they can be accessible any time. Moreover, the output and results of analyses are monitored by means of appropriate display. Finally, user may interrupt or reset the system via controller.

Before initiation of any task, the controller performs self test procedure to verify the proper functionality of all parts of the system including, motors, drivers, electronic circuits, power supply, processors, etc. Furthermore, controller checks the system during performance for possible fault and sends warning message to the user. As an example, if user set the limit of displacement 3 mm and set the speed of deformation 20 mm/s, the controller send a message for requesting reconfirmation of the parameters. Moreover, the controller checks the performance of the system during task and stops the mechanism in case of inappropriate consequences. For example, the first deformation speed is set 4 mm/s while the quality of the object is still unknown and no deformation has occurred after applying the force up to half of the limit range, the controller would stop the procedure and send user a message of error.

What is claimed is:

1. A method of real time in-vivo in-situ characterization of soft materials and biological tissues based on a model of viscoelastic material consisting of interactive hyperelastic element and viscous element which is comprising of viscous media within the structure of an object during constant speed rate of deformation under compressing force, in terms of nonlinear properties of elastic modulus as a function of strain and viscosity coefficient as a function of strain and strain rate comprising:

a—compressing a target object to be characterized at low speed for a first deformation by means of a mechanism including touching surfaces, actuators, motors, encoders, touch and force sensors and accessories through following steps:

I. moving the touching surfaces of the mechanism attached to a device selected from the group of a minimally invasive surgery tool, a robot end effector or a manually powered apparatus; wherein the device is built with the approximate shape and contour of the object accessible surfaces in order to reduce distortion of the object during deformation; wherein the touch and force sensors are distributed on the touching surfaces and spaced a distance with respect to each other, wherein the step of moving the touching surfaces occurs until one touch sensor is triggered at an initial position;

II. recording time and coordinates of touch points of triggered touch sensors and the object's contour by means of the encoders, and an analyzer; wherein the analyzer consists of a computer or processing unit, software, and interfaces; compressing the object by the motor or actuator regulated by a controller, by applying compressive force at a constant speed within the rate of Hyperelasticity Deformation Speed Limit (HDSL) of the target object wherein said rate is the limit of deformation speed that a viscoelastic object behaves as a hyperelastic material;

III. continuing compressing the object, reading and recording the three dimensional (3D) coordinates of the touch sensors, force sensors and a deformation of the object with respect to time; wherein the 3D coordinates of the touch and force sensors are determined with respect to one touch and one force sensors as the references of coordination system;

IV. stopping the compressing of the object according to a preset force limit regulated by the controller;

V. retracting the touching surfaces of the mechanism to the initial position of the first touch waiting for the object to return to an initial undeformed status under object's elastic behavior;

VI. calculating a shape, volume and displacement of the object at the initial undeformed status and at a plurality of incremental time periods based on data collected by the touch sensors, force sensors and the encoders during deformation by means of the computer through interpolation, extrapolation and numerical method of data over the object boundaries;

VII. integrating of elastic energy over the object volume based on the energy consumed by the actuator or motor and calculating a nonlinear elasticity modulus of the object during deformation at plurality of incremental time periods by means of the computer;

VIII. preparing a force, displacement and nonlinear elasticity modulus map of the object per individual sensor and the object for every incremental step of time by means of the computer;

IX. monitoring the results of nonlinear elasticity modulus calculations by means of tables, graphs, and models on a computer display in order to show the object structural elasticity and structural inconsistency including lumps, and various tissue combinations;

b—deforming the target object to be characterized second time through following steps:

i. setting a constant viscoelastic deformation speed of a second deformation of the object above the HDSL and within the Viscoelastic Deformation Speed Limits (VDSL), within which object behaves as a time dependent material and beyond which the object behaves as a semi-solid object, regulated by the controller based on the data collected and analyzed during first deformation;

ii. starting touching the object with the mechanism touching surfaces until one touch sensor is triggered; the touching surfaces including a clamp, jaw, indenter, plate, probe or rod;

iii. applying the compressive force with the constant viscoelastic deformation speed by the mechanism actuator or motor to deform the object to the pre-set limit of force regulated by the controller;

iv. recording the data of the touch and force sensors, and the encoder for each individual sensor with respect to time by means of the computer at a second plurality of incremental steps of time;

v. stopping the deformation of the object by the mechanism regulated by the controller;

vi. pulling back the mechanism touching surfaces to the initial position;

vii. calculating a velocity gradient of the viscous media of the object based on a boundary deformation of the object for each of the second plurality of incremental steps of time by using the recorded data of the touch and force sensors and the encoders; viii. integrating the viscous media velocity gradient of the object for the second plurality of incremental steps of time;

ix. calculating the energy consumed by motor or actuator for each of the second plurality of incremental steps by means of the mechanism force sensors and encoders and integration of the energy consumed by object using the force and touch sensors and encoders' readings during deformation for each incremental step of time;

x. calculating the elasticity energy for the first plurality of steps of time using the readings of the first deformation within HSDL;

xi. calculating the energy dissipation of viscoelasticity of the object during the compression of step iii of part b by applying the equation of total energy consumed equal to summation of elasticity energy and dissipated viscosity energy during applying compressive force for the second plurality of incremental steps of time;

xii. calculating viscosity coefficient of the object for the second plurality of incremental steps of time by using calculated energy dissipation and integrated viscosity gradient;

xiii. preparing a map of nonlinear viscosity coefficient of the object for each individual force sensor and entire object;

c—deforming repeatedly the object to be characterized through the second deformation steps with different deformation speeds within VDSL for calculating more viscosity coefficients at different strain rates;

d—monitoring the properties of the object based on nonlinear elastic modulus as a function of strain and nonlinear viscosity coefficients as a functions of strain and strain rate;

e—monitoring the structure of the object in terms of structural elasticity and viscous media configuration and viscosity coefficients within object boundary by means of table, graph, model and haptic system.

2. The method of claim 1, wherein said soft material and biological tissue behaves as a viscoelastic material, as a hyperelastic material or as a plastic material or behaves as any combination of these materials.

3. The method of claim 1, wherein the results of one deformation within HDSL and one deformation at VSDL are adequate for characterization of the soft material in most medical and biological applications and the results of more deformations at different viscoelastic deformation speeds within VSDL provides more data in order to generate more precise curves of nonlinear viscoelastic materials.

4. The method of claim 1, wherein said environmental factors including temperature and gravity which affect the quality of viscous media and elastic elements of the object are considered during characterization of the object.

5. The method of claim 1, comprising integrating the mechanisms, analyzer and controller in robotic manipulators or minimally invasive surgery apparatus in order to characterize soft materials and/or biological tissue providing required information for proper manipulation of the object.

6. The method of claim 1, comprising integrating the mechanisms, analyzer and controller in robotic manipulators or minimally invasive surgery apparatus in order to characterize soft materials and/or biological tissue to perform disorders diagnosis of biological tissues by comparing provided properties and structure of biological tissues.

7. The method of claim 1, comprising integrating the mechanisms, analyzer and controller in robotic manipulators, machines or apparatus for characterization of soft materials and biological tissues to provide tactile feedback in a medical procedure.

8. The method of claim 1, comprising integrating the mechanisms, analyzer and controller in a machine of material testing in order to provide properties of soft materials.

* * * * *